US012117429B2

(12) United States Patent
Morgan et al.

(10) Patent No.: US 12,117,429 B2
(45) Date of Patent: Oct. 15, 2024

(54) MINI POINT OF CARE GAS CHROMATOGRAPHIC TEST STRIP AND METHOD TO MEASURE ANALYTES

(71) Applicant: Biometry Inc., Boston, MA (US)

(72) Inventors: Thomas T. Morgan, Stow, MA (US); David L. Carnahan, Needham, MA (US); Bryan Nolan, Brookline, MA (US)

(73) Assignee: Biometry Inc., Boston, MA (US)

( * ) Notice: Subject to any disclaimer, the term of this patent is extended or adjusted under 35 U.S.C. 154(b) by 0 days.

(21) Appl. No.: 17/236,586

(22) Filed: Apr. 21, 2021

(65) Prior Publication Data

US 2021/0239665 A1    Aug. 5, 2021

Related U.S. Application Data

(63) Continuation of application No. 15/538,111, filed as application No. PCT/US2015/000180 on Dec. 23, (Continued)

(51) Int. Cl.
   *G01N 30/95*      (2006.01)
   *G01N 27/12*      (2006.01)
   (Continued)

(52) U.S. Cl.
   CPC ............. *G01N 30/95* (2013.01); *G01N 27/12* (2013.01); *G01N 30/92* (2013.01); *G01N 33/497* (2013.01)

(58) Field of Classification Search
   CPC ........ G01N 30/95; G01N 27/12; G01N 30/92; G01N 33/497
   See application file for complete search history.

(56) References Cited

U.S. PATENT DOCUMENTS

| 4,802,487 A | 2/1989 | Martin et al. |
| 5,169,512 A | 12/1992 | Wiedenmann et al. |

(Continued)

FOREIGN PATENT DOCUMENTS

| CA | 2849868 A1 | 5/2013 |
| CA | 2849872 A1 | 5/2013 |

(Continued)

OTHER PUBLICATIONS

English machine translation for document JPH06288974.*

(Continued)

*Primary Examiner* — Peter J Macchiarolo
*Assistant Examiner* — Anthony W Megna Fuentes
(74) *Attorney, Agent, or Firm* — Wilmer Cutler Pickering Hale and Dorr LLP

(57) ABSTRACT

A mini point of care gas chromatographic test strip and method to measure analytes is disclosed. A system for determining the concentration of at least one analyte in a fluid sample having a plurality of analytes includes a base substrate, a first electrode pair disposed over the base substrate, and a first sensing chemistry responsive to at least one analyte in the sample. The first sensing chemistry is in electrical communication with the first electrode pair, and a first chromatographic layer is disposed over the at least one sensing chemistry. At least one analyte of the plurality of analytes moves through the first chromatographic layer at a different rate relative to the movement of other analytes of the plurality of analytes.

14 Claims, 48 Drawing Sheets

Related U.S. Application Data 2015, now Pat. No. 11,175,268, which is a continuation of application No. PCT/US2015/034869, filed on Jun. 9, 2015.

(60) Provisional application No. 62/146,847, filed on Apr. 13, 2015, provisional application No. 62/146,824, filed on Apr. 13, 2015, provisional application No. 62/096,674, filed on Dec. 24, 2014, provisional application No. 62/013,233, filed on Jun. 17, 2014, provisional application No. 62/009,531, filed on Jun. 9, 2014.

(51) Int. Cl.
  *G01N 30/92* (2006.01)
  *G01N 33/497* (2006.01)

(56) References Cited

U.S. PATENT DOCUMENTS

| | | | |
|---|---|---|---|
| 5,239,483 | A | 8/1993 | Weir |
| 5,698,083 | A | 12/1997 | Glass |
| 6,200,444 | B1 | 3/2001 | Ahlers et al. |
| 6,612,306 | B1 | 9/2003 | Mault |
| 7,179,421 | B1 | 2/2007 | Ho |
| 7,189,360 | B1 | 3/2007 | Ho |
| 7,956,525 | B2 | 6/2011 | Armitage et al. |
| 9,170,248 | B2 | 10/2015 | Fleischer et al. |
| 9,315,463 | B2 | 4/2016 | Prat Quinones et al. |
| 9,329,161 | B2 | 5/2016 | Fleischer et al. |
| 2003/0057109 | A1 | 3/2003 | Wang et al. |
| 2003/0175161 | A1 | 9/2003 | Gabriel et al. |
| 2004/0133116 | A1 | 7/2004 | Abraham-Fuchs et al. |
| 2007/0048180 | A1 | 3/2007 | Gabriel et al. |
| 2007/0114130 | A1 | 5/2007 | Lankheet et al. |
| 2007/0114138 | A1 | 5/2007 | Krasteva et al. |
| 2007/0281288 | A1 | 12/2007 | Belkin et al. |
| 2008/0026473 | A1 | 1/2008 | Wang et al. |
| 2008/0214917 | A1 | 9/2008 | Boecker |
| 2009/0320560 | A1 | 12/2009 | Ross |
| 2010/0106039 | A1 | 4/2010 | Abraham-Fuchs et al. |
| 2010/0176006 | A1 | 7/2010 | Bickford et al. |
| 2010/0183620 | A1 | 7/2010 | Bhawe et al. |
| 2010/0282245 | A1 | 11/2010 | Star et al. |
| 2011/0070634 | A1 | 3/2011 | Takahashi et al. |
| 2011/0077544 | A1 | 3/2011 | Abraham-Fuchs et al. |
| 2011/0098591 | A1 | 4/2011 | Haick et al. |
| 2011/0138904 | A1 | 6/2011 | Nakaso |
| 2012/0006102 | A1 | 1/2012 | Bryant et al. |
| 2012/0065535 | A1 | 3/2012 | Abraham-Fuchs et al. |
| 2012/0148634 | A1 | 6/2012 | Dodd et al. |
| 2012/0263760 | A1 | 10/2012 | Dodd et al. |
| 2013/0062211 | A1 | 3/2013 | Deshusses et al. |
| 2013/0274574 | A1 | 10/2013 | Say et al. |
| 2014/0042025 | A1 | 2/2014 | Furuta |
| 2014/0065219 | A1 | 3/2014 | Bosch et al. |
| 2014/0130574 | A1 | 5/2014 | Happ et al. |
| 2015/0112221 | A1 | 4/2015 | von Sicard et al. |
| 2016/0081589 | A1 | 3/2016 | Reisinger et al. |

FOREIGN PATENT DOCUMENTS

| | | | |
|---|---|---|---|
| CA | 2892931 | A1 | 6/2014 |
| CN | 101742964 | A | 6/2010 |
| CN | 102023178 | A | 4/2011 |
| CN | 102253105 | A | 11/2011 |
| CN | 102368953 | A | 3/2012 |
| CN | 102596030 | A | 7/2012 |
| CN | 104883971 | A | 9/2015 |
| CN | 105050501 | A | 11/2015 |
| CN | 106687035 | A | 5/2017 |
| DE | 102007049715 | A1 | 7/2008 |
| DE | 102014210574 | A1 | 12/2015 |
| DE | 102014219132 | A1 | 3/2016 |
| GB | 2469803 | A | 11/2010 |
| JP | H06-229967 | A | 8/1994 |
| JP | H06-265499 | A | 9/1994 |
| JP | H06-288974 | A | 10/1994 |
| JP | 2002-357589 | A | 12/2002 |
| JP | 2007/192805 | A | 8/2007 |
| JP | 2008-180529 | A | 8/2008 |
| JP | 2009-537219 | A | 10/2009 |
| JP | 2010/025721 | A | 2/2010 |
| JP | 2010-025728 | A | 2/2010 |
| JP | 2010-048580 | A | 3/2010 |
| JP | 2010-507073 | A | 3/2010 |
| JP | 2014-522973 | A | 9/2014 |
| JP | 2016-136152 | A | 7/2016 |
| KR | 2008-0038541 | A | 5/2008 |
| KR | 10-1786803 | B1 | 11/2017 |
| WO | WO-03067241 | A2 * | 8/2003 | ............ G01N 27/12 |
| WO | WO-2005/082934 | A2 | 9/2005 |
| WO | WO-2006/012451 | | 2/2006 |
| WO | WO-2007/006926 | | 1/2007 |
| WO | WO-2007/039297 | | 4/2007 |
| WO | WO-2007/064912 | | 6/2007 |
| WO | WO-2007/136523 | A2 | 11/2007 |
| WO | WO-2007/141510 | A1 | 12/2007 |
| WO | WO-2008/039165 | A2 | 4/2008 |
| WO | WO-2008/099072 | | 8/2008 |
| WO | WO-2010/106898 | | 9/2010 |
| WO | WO-2010/121321 | | 10/2010 |
| WO | WO-2011/015620 | | 2/2011 |
| WO | WO-2011/057757 | | 5/2011 |
| WO | WO-2011/141180 | | 11/2011 |
| WO | WO-2014/045584 | A1 | 3/2014 |
| WO | WO-2015/191558 | A1 | 12/2015 |
| WO | WO-2016/105464 | A2 | 6/2016 |
| WO | WO-2018/017699 | A1 | 1/2018 |

OTHER PUBLICATIONS

Binions et al., "Discrimination Effects in Zeolite Modified Metal Oxide Semiconductor Gas Sensors", IEEE Sensors Journal, vol. 11, No. 5, May 1, 2011, pp. 1145-1151.

Binions et al., "Discrimination Effects in Zeolite Modified Metal Oxide Semiconductor Gas Sensors," IEEE Sensors 2009 Conference, Christchurch, New Zealand Oct. 25-28, 2009 pp. 1090-1095.

Definition of "Nanostructure", from Oxford English Dictionary, reviewed on Apr. 7, 2020, 1 page.

Definition of "Polymer", from Oxford English Dictionary, reviewed on Apr. 7, 2020, 2 pages.

English machine translation of JPH06288974, which published on Oct. 18, 1994. 7 pages.

European Search Report mailed Nov. 15, 2017, in European Application No. 15806563.1, 8 pages.

European Search Report mailed Nov. 7, 2017, in European Application No. 15873758.5, 9 pages.

European Search Report mailed Oct. 15, 2019, in the European Patent Application 17831778.0, 15 pages.

International Search Report and Written Opinion mailed Feb. 23, 2016, in the International Application No. PCT/US2015/00180, 18 pages.

International Search Report and Written Opinion mailed Sep. 1, 2015, in the International Application No. PCT/US2015/034869, 21 pages.

International Search Report and Written Opinion mailed Sep. 29, 2017, in the International Application No. PCT/US2017/042830, 14 pages.

Lange et al., "Chemiresistors based on conducting polymers: A review on measurement techniques", Analytica Chimica Acta, (2011) vol. 687, No. 2, published online Nov. 19, 2010, pp. 105-113.

Seesaard et al., "Health Status Monitoring by Discrimination of Exhaled Breath with an Electronic Nose", The 2012 Biomedical Engineering International Conference (BMEiCON), IEEE, Dec. 5, 2012, pp. 1-5.

(56) References Cited

OTHER PUBLICATIONS

Yu et al., "On-line monitoring of breath by membrane extraction with sorbent interface coupled with CO2 sensor," Journal of Chromatography, Nov. 12, 2004, vol. 1056(1-2), pp. 35-41.

* cited by examiner

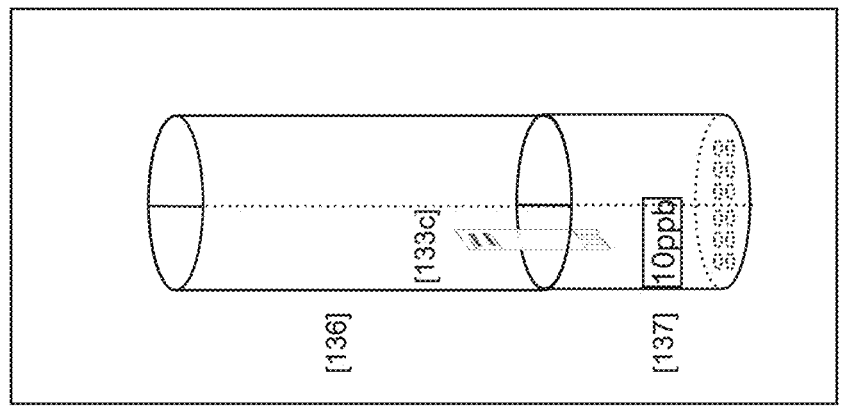
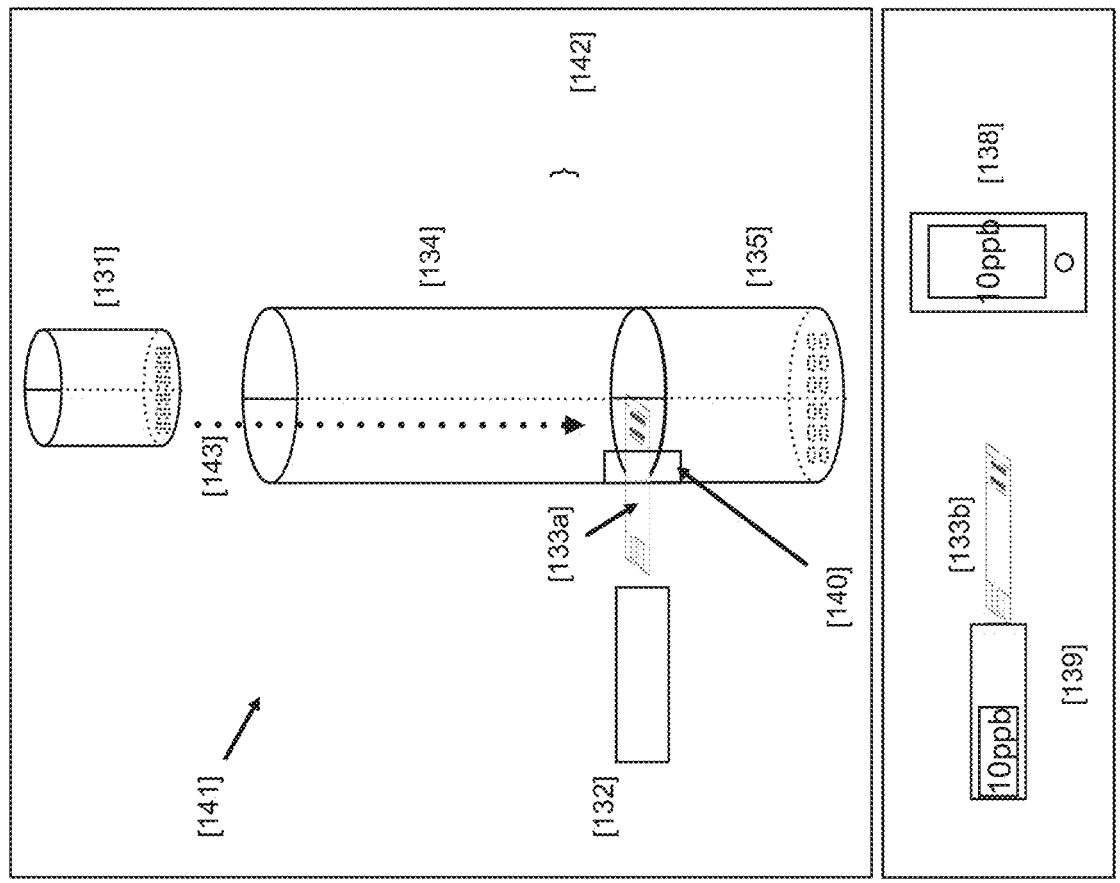
FIG. 1a

| Substance | Expected concentrations in exhaled breath of healthy subjects |
|---|---|
| $CO_2$ | < 4-5 % |
| Ethanol | 13 - 1000 ppb |
| $NH_3$ | 50 - 500 ppb |
| CO | 0.5 - 15 ppm |
| Isoprene | 5 - 380 ppb |
| $H_2O_2$ | < 1 ppb |
| $O_2$ | 17 % |
| $H_2$ | < 20 ppm |
| $H_2S$ | 300 - 500 ppb |
| Acetone | 12 - 1880 ppb |
| Acetonitrile | < 100 ppb |
| Acetaldehyd | < 50 ppb |
| $NO_2$ | Below detectable level |
| Other | |

FIG. 3

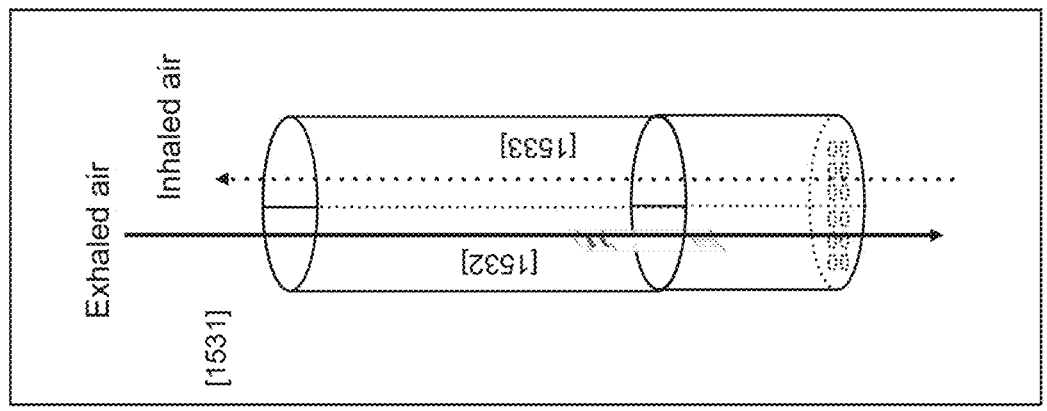
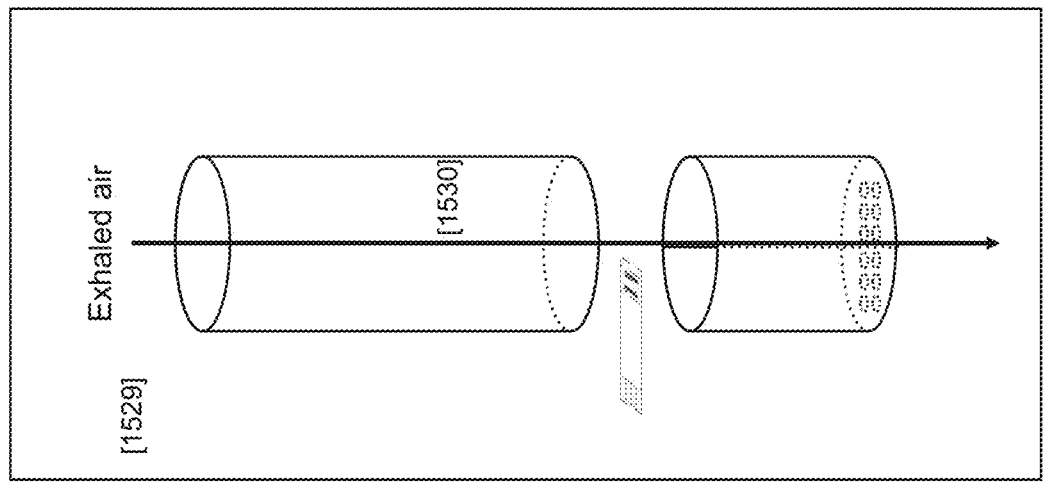
FIG. 15b

Sensing Chemistry Additives

| | |
|---|---|
| Water | Polyurethanes |
| Organic solvents | Cellulosics |
| Polyvinyl butyral | Clays |
| Glycerol | Silicones |
| Ethylene glycol | Stearic acid |
| Polysaccharides | Anionic surfactants |
| Proteins | Cationic surfactants |
| Silica | Nonionic surfactants |
| Polyacrylic acid | Zwitterionic surfactants |
| Sodium dodecyl sulfate | Fluorosurfactants |
| Polyoxyethylene nonylphenyl ether | Alkyltrimethylamminum salts |

FIG. 20

Fully Assemble Test Strip Example
[2201]
Foil barrier for puncture with device
[2202]
Foil barrier with manual removal tab
[2203]
Electrodes in Measuring Unit (Not Directly on Test Strip)
[2204]
FIG. 22

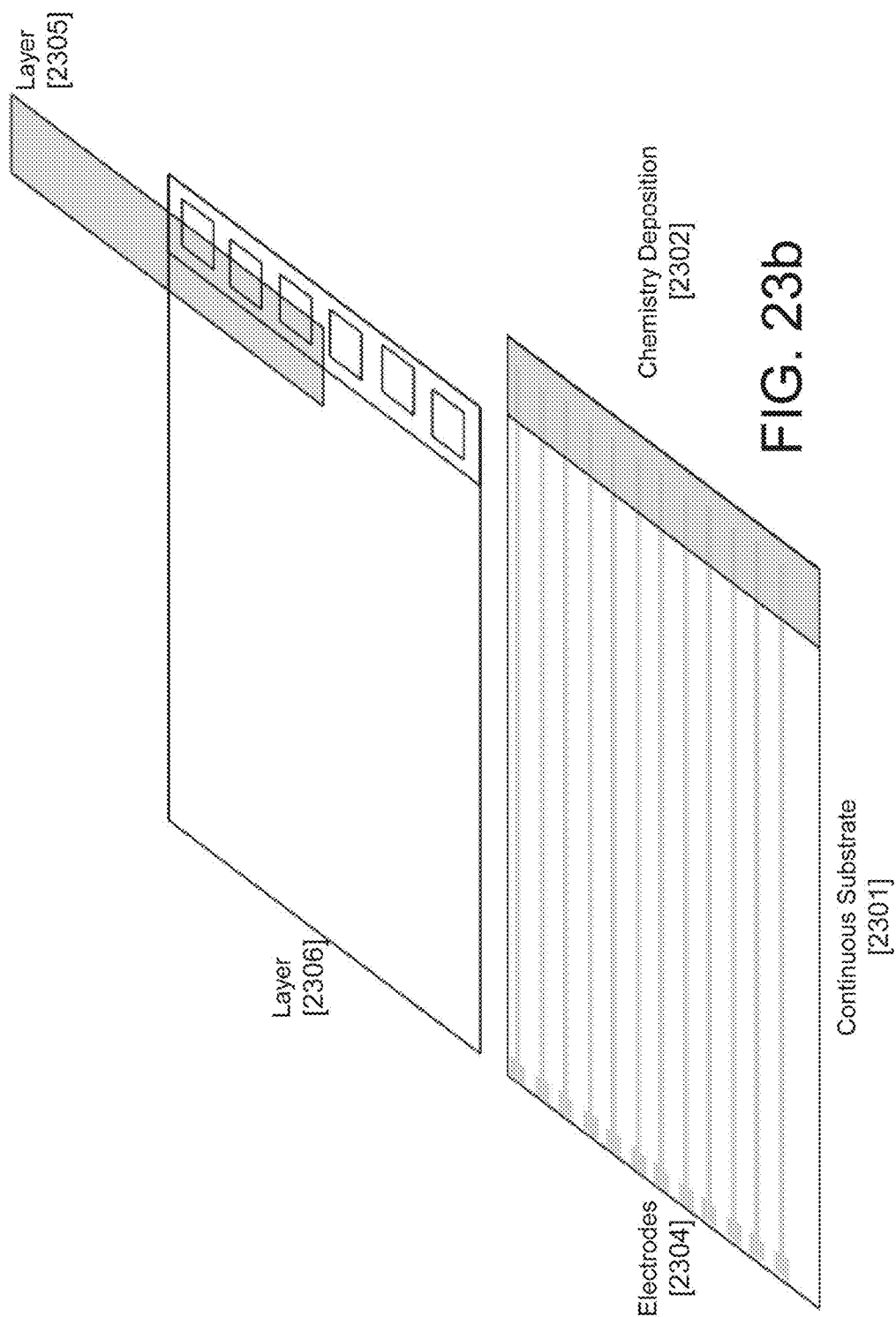

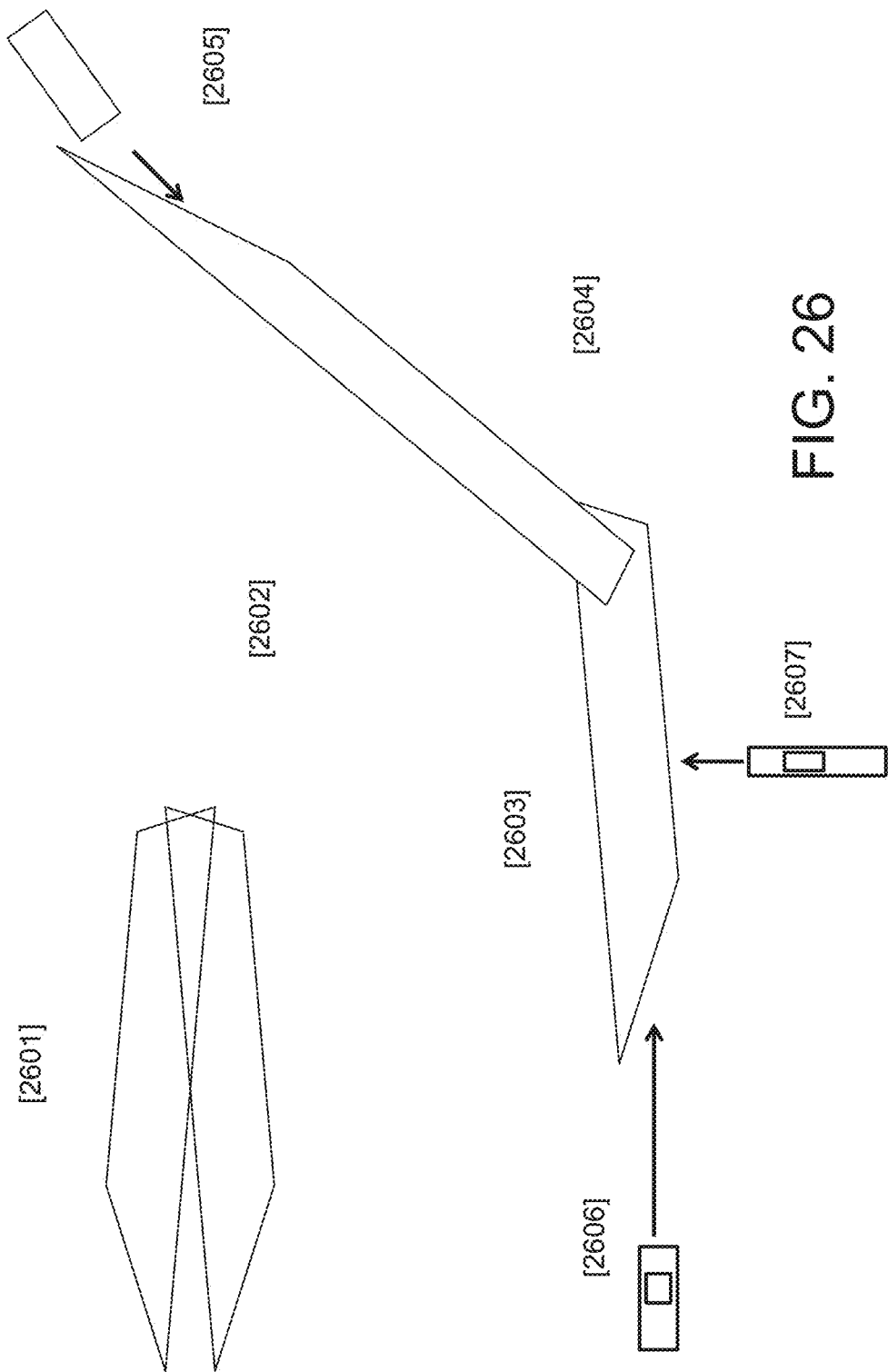

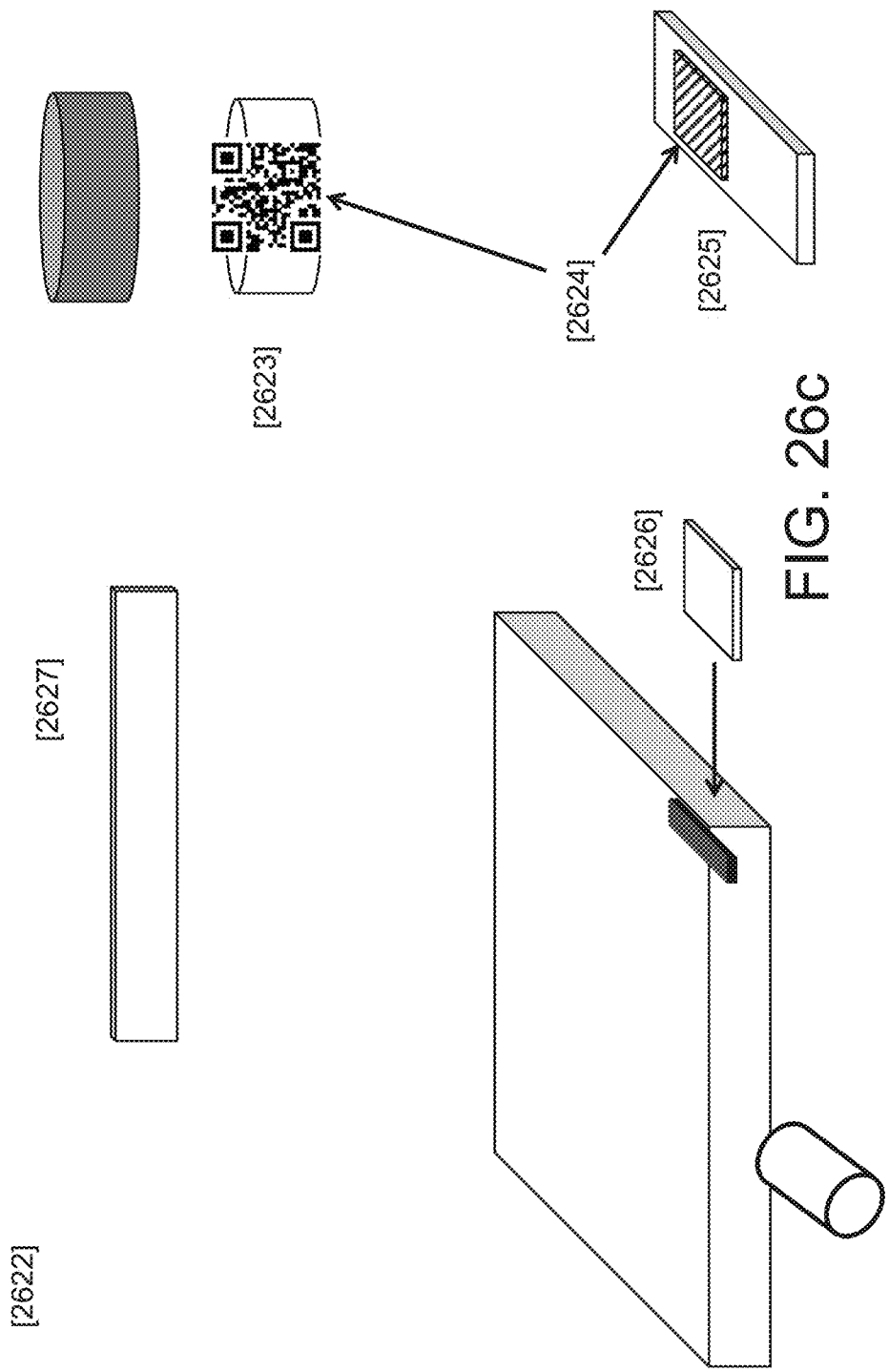

MINI POINT OF CARE GAS CHROMATOGRAPHIC TEST STRIP AND METHOD TO MEASURE ANALYTES

CROSS-REFERENCES TO RELATED APPLICATIONS

This application is a Continuation Application of U.S. Non-Provisional patent application Ser. No. 15/538,111 entitled Mini Point of Care Gas Chromatographic Test Strip and Method to Measure Analytes, filed Jun. 20, 2017, which is a National Stage Entry of PCT International Application Number PCT/US2015/000180, entitled Mini Point of Care Gas Chromatographic Test Strip and Method to Measure Analytes, filed Dec. 23, 2015, which claims the benefit under 35 U.S.C. § 119(e) to U.S. Provisional Patent Application No. 62/096,674, entitled Mini Point of Care Gas Chromatographic Test Strip and Method to Measure Analytes, filed Dec. 24, 2014, U.S. Provisional Patent Application No. 62/146,847, entitled Low Cost Test Strip and Method to Measure Analyte, filed Apr. 13, 2015, and PCT/US15/34869, entitled Low Cost Test Strip and Method to Measure Analyte, filed Jun. 9, 2015, which claims priority to U.S. Provisional Patent Application No. 62/146,824, entitled Low Cost Test Strip and Method to Measure Analyte, filed Apr. 13, 2015, U.S. Provisional Patent Application No. 62/013,233, entitled Method for Collecting and Analyzing Data to Monitor and Manage Patients with Chronic Respiratory Disease, filed Jun. 17, 2014, and U.S. Provisional Patent Application No. 62/009,531, entitled Low Cost Test Strip And Method to Measure Analyte, filed Jun. 9, 2014, which are hereby incorporated by reference in their entirety.

BACKGROUND

Field of Invention

This invention is generally related to detecting environmental changes. More specifically, the invention relates to a method for gas or vapor separation and measurement that includes a multilayered, low-cost limited-use test.

Description of Related Art

There are many different types of sensors and technologies available for gas and analyte detection known in the art. In the human medical industry, gas sensors are used in many areas including anesthesia and respiratory care. The sensors are typically configured to monitor inhaled anesthetic agents, $O_2$, $CO_2$, and $N_2O$. Another example includes hydrogen and methane used to diagnose digestive disorders. Other examples include, measuring nitric oxide (NO) in exhaled breath, which has recently gained traction to diagnosis and monitor airway inflammation in patients with chronic respiratory diseases. Several point of care technologies are commercially available the detection of gas such as electrochemical sensors and Metal Oxide Semiconductor (referred hereafter as MOS). The mechanics and detection methods of these sensors electrochemical sensing are known in the art.

Both MOS and electrochemical sensors have the disadvantage of being cross sensitive to interfering gases and are typically sensitized to one specific analyte. These characteristics put the technology at a disadvantage of detecting a single analyte or multiple analytes in a stream of mixed or multiple gases.

Another method of gas analysis is through Gas Chromatography. Gas chromatography is a mechanism through which a complex mixture of gasses can be temporally separated. Gas chromatography is typically coupled to some method of detection or sensor for a particular analyte or set of analytes. Typically, gas chromatography uses a flow-through narrow bore tube coated with a particular agent to affect gas-surface interactions, known as the column, through which a complex mixture of gasses is passed, but may include a packed bed of similarly functionalized particulates. Individual gasses of the gas stream (mobile phase) have different affinities for the side-wall of the column (the stationary phase). As a result, different gasses pass through the column at different rates depending on their various chemical and physical properties and their interaction with the specific column filling. As the chemicals exit the end of the column, they are detected and identified in a variety of common means, known to those skilled in the art. The function of the stationary phase in the column is to separate different components, causing each component to exit the column at a different time (retention time). Other parameters that can be used to alter the order or time of retention are the carrier gas flow rate, column length, and the temperature.

Gas chromatographs have the disadvantage of being too complicated, bulky and expensive to be used suitably in a point of care environment (such as a doctor's office or home) or in the field (such as in military, police, oil and gas, aerospace, agricultural industries, etc.)

BRIEF SUMMARY OF THE INVENTION

An embodiment of the invention includes a test strip that may be configured in a variety of ways based on the gas of interest and environment in which the test strip is placed. At the most basic level, the test strip comprises a substrate and a sensing chemistry. In some embodiments, the test strip is generally comprised of a substrate, at least one electrical connection, at least one sensing chemistry and at least one additional layer. The layer, or layers, may serve a single purpose, or multiple purposes, for example, to protect the sensing chemistry from interfering substances, in addition to providing, for example, a spacer between layers. A single layer or the combination of layers provides selective permeation or diffusion of gases to the sensing chemistry allowing for time separation and sensing of one or multiple gases in a gas stream. The test strip may provide a quantitative and/or a qualitative read out. The test strip may stand alone or be combined with other devices. Examples of these devices include, but are not limited to, mechanisms to control the gas flow, electronic means to power the device and provide a read out, temperature measurement and control, and/or mechanisms to filter or condition the gas prior to readout.

One embodiment of the invention is for use in the medical industry. It comprises a test strip and device(s) configured to measure exhaled nitric oxide in human breath. The information from the test strip and device may be part of a larger monitoring system for patient health. The test strip consists of a substrate, zero or more electrodes, at least one sensing chemistry, and at least one layer. The test strip may be in communication with a device to provide a signal and read-out. It may also be in communication with a device to control the flow of gas to the sensor.

Another embodiment of the invention is for use in the medical industry. It comprises a test strip and device(s) configured to measure exhaled nitric oxide in human breath. The information from the test strip and device may be part of a larger monitoring system for patient health. The test strip consists of a substrate, zero or more electrodes, at least one sensing chemistry, and at least one layer to provide time based separation of gases in a gas stream. The test strip may be in communication with a device to provide a signal and readout. It may also be in communication with a device to control the flow of gas to the sensor. Another embodiment of the invention is for use in the medical industry. It comprises a test strip and device(s) configured to measure exhaled nitric oxide in human breath. The information from the test strip and device may be part of a larger monitoring system for patient health. The test strip consists of a substrate, three electrodes, at least one sensing chemistry spanning two electrodes, at least one reference chemistry spanning two electrodes where one of the electrodes is shared with the sensing chemistry, and at least one layer to provide time-based separation of gases in a gas stream. In one embodiment, the reference chemistry is covered. The test strip may be in communication with a device to provide a signal and readout. It may also be in communication with a device to control the flow of gas to the sensor.

Other embodiments of the invention are configured to detect hydrogen and/or methane, or acetone.

Other electrode configurations are possible without deviating from the spirit of the invention.

Other embodiments of the invention are configured to detect one or more compounds in breath related to disease.

Other embodiments of the invention are configured to detect one or more gases relevant to the industrial, automotive, environmental, military, aerospace, agricultural, and veterinary industries.

Other embodiments of the invention are configured to detect one or more biological or non-biological fluids and gases present in such fluids.

An aspect of the invention provides a system for determining the concentration of at least one analyte in a fluid sample having a plurality of analytes, the system comprising, a base substrate, a first electrode pair disposed over the base substrate, a first sensing chemistry responsive to at least one analyte in the sample, wherein the first sensing chemistry is in electrical communication with the first electrode pair, and a first chromatographic layer disposed over the at least one sensing chemistry, wherein at least one analyte of the plurality of analytes moves through the first chromatographic layer at a different rate relative to the movement of other analytes of the plurality of analytes.

In one embodiment the system comprises a second electrode pair disposed over the substrate and a second sensing chemistry responsive to at least one analyte in the sample, wherein the second sensing chemistry is in electrical communication with the second electrode pair.

In another embodiment the system of further comprises at least one of a blocking layer and a second chromatographic layer disposed over the second sensing chemistry, wherein the blocking layer inhibits contact between the second sensing chemistry and at least one analyte in the fluid sample, and wherein at least one analyte of the plurality of analytes moves through the second chromatographic layer at a different rate relative to the movement of other analytes of the plurality of analytes.

In another embodiment of the system at least one of a physical, optical, and electrical property of the first sensing chemistry changes when exposed to at least one analyte of the plurality of analytes to a different degree relative to a change in a same physical, optical, or electrical property of the second sensing chemistry when exposed to said analyte.

In another embodiment the system further comprises a bridge circuit, the bridge circuit coupled to the first sensing chemistry and the second sensing chemistry, wherein the bridge circuit provides information indicative of a change in at least one of a physical, optical, and electrical property in the first sensing chemistry and the second sensing chemistry when both are exposed to at least one analyte.

In one embodiment the system further comprises an inlet capable of receiving the fluid sample; and a flow controller in fluid communication with the inlet and the first sensing chemistry, wherein the flow controller is capable of providing at least a portion of the fluid sample to the first sensing chemistry.

In another embodiment the system further comprises a first inlet capable of receiving the fluid sample, a removable fluid sample vessel in fluid communication with the first inlet, and a second inlet spaced apart from the first inlet, the second inlet being in fluid communication with the first sensing chemistry, wherein the removable fluid sample vessel is capable of transporting the fluid sample to the first sensing chemistry via the second inlet.

One aspect of the invention provides a method for determining the concentration of at least one analyte in a fluid sample, the method comprising, providing a system comprising, a base substrate, a first electrode pair disposed over the base substrate, a first sensing chemistry responsive to at least one analyte in the sample, wherein the first sensing chemistry is in electrical communication with the first electrode pair, and a first chromatographic layer disposed over the at least one sensing chemistry, wherein at least one analyte of the plurality of analytes moves through the first chromatographic layer at a different rate relative to the movement of other analytes of the plurality of analytes, and measuring at least one of a voltage across the first electrode pair, a resistance across the first electrode pair, and a current flow across the first electrode pair.

In one embodiment of the method the system further comprises, a second sensing chemistry, the second sensing chemistry being responsive to at least one analyte in the sample, a second electrode pair, the second sensing chemistry being in electrical communication with the second electrode pair, and the method further comprises measuring at least one of a voltage across the second electrode pair, a resistance across the second electrode pair, and a current flow across the second electrode pair.

In another embodiment the method further comprises providing data correlating known concentrations of the at least one analyte with at least one of voltage values, resistance values, and current flow values, and determining information about the concentration of the at least one analyte based on the provided data and the measurement of first electrode pair.

In another embodiment of the method the measuring comprises determining at least one of (1) a change in the measurement of the first electrode pair over time, (2) a change in a rate of change in the measurement of the first electrode pair over time, (3) whether the measurement of the first electrode pair exceeds a first threshold value, and (4) whether the measurement of the first electrode pair is less than a second threshold value.

Any of the aspects or embodiments of the invention described above can be combined with any of the other aspects and embodiments set forth herein.

BRIEF DESCRIPTION OF THE DRAWINGS

In the drawings:

FIG. 1a is demonstrates variations of the assembled device and test strip.

FIG. 3 is an example of gases found in exhaled human breath.

FIG. 15, FIG. 15a, and FIG. 15b demonstrate examples of variations of the mechanisms to control the flow of gas to the test strip and methods of filtering the gas stream.

FIG. 20 is an example of the sensing chemistry additives.

FIG. 22 shows examples of fully assembled test strips.

FIG. 23a, FIG. 23b and FIG. 23c demonstrate an example of the test strips in mass production.

FIG. 26 demonstrates an embodiment of the device that folds.

FIG. 26a demonstrates an embodiment of a device that folds and incorporates the design described in FIGS. 15, 15a, 15b, 16, and/or FIG. 16a.

FIG. 26c demonstrates an embodiment of the invention wherein the output of the device is selected from a plurality of endpoints.

DETAILED DESCRIPTION

Embodiments of the invention use materials and manufacturing techniques to produce test strips in high volume at low-cost for the measurement of gas in various industries and environments. The test strip may measure a single gas or multiple gases. At its most basic level, the test strip is comprised of a substrate/base and sensing chemistry. Embodiments of the test strip include a substrate, a means of establishing an electrical connection (i.e. electrode), at least one sensing chemistry and at least one additional layer. The configuration and design may be modified based on the gas of interest and environment in which the test strip will be placed. The sensing chemistry is selected based on the gas of interest, and the electrodes are configured to measure the chemical reaction that occurs. The layer, or layers, may serve multiple purposes including, but not limited to, masking for chemistry deposition, adhesion between layers, protection from interfering substances, enhancing the selectivity and/or sensitivity of the test strip and spacing. Details regarding the electrode, the chemistry, and the layers are described below.

Embodiments of the invention may apply different sensing chemistries, configurations and layers to the test strip based on the gas of interest, and the environment in which the test strip will be placed. The tests strips may be configured to provide qualitative and/or quantitative analysis of a gas, or gases. The test strip may be combined with other devices, or stand alone. Other devices may be used control the delivery of the gas of interest to the test strip, or to process a signal from the test strip. Control may include, but is not limited to, flow, filtration, pre-treatment, etc.

Figure 13:
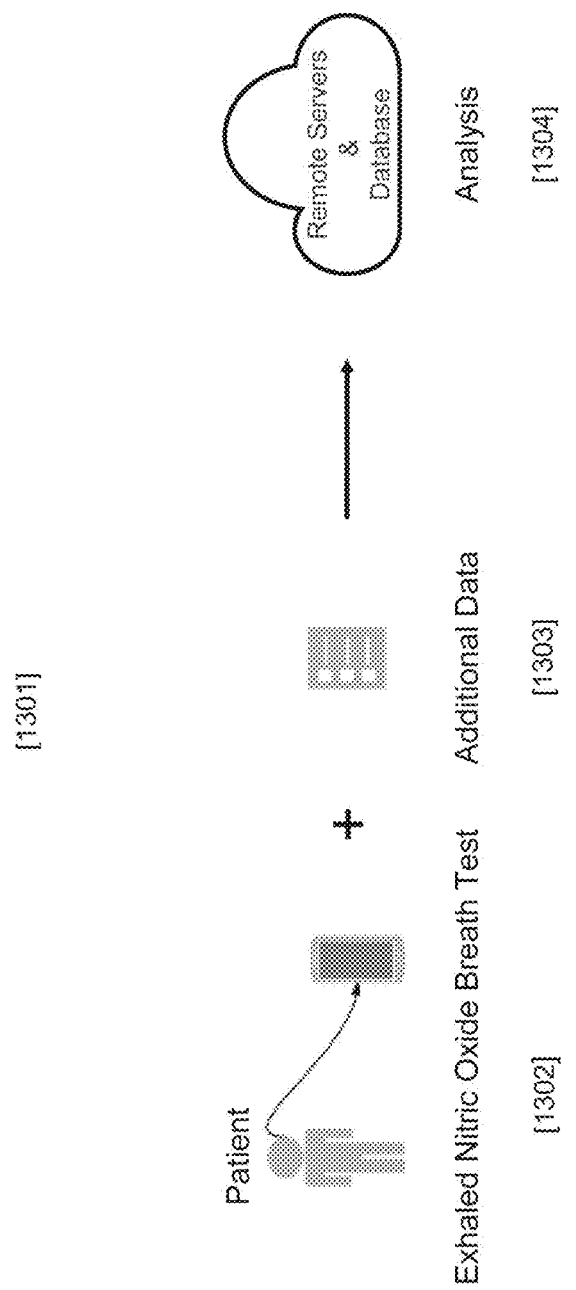
FIG. 13 is an example of one embodiment of the invention in a larger system for monitoring patients.

One embodiment of the invention is a test strip for use in the medical industry to measure exhaled nitric oxide in human breath. Other embodiments may be used to detect other gases in breath such as hydrogen, methane, ethanol or acetone. The test strip and accompanying devices may be single patient, or multiple patient uses. The devices, device components and test strip may be disposable, reusable or any combination. The data gathered from the result of using the test strip, in this example, exhaled nitric oxide breath test, may be part of a larger patient monitoring system or may stand alone. FIG. 13 provides an example of a patient monitoring system [1301] whereby the patient performs a nitric oxide breath test [1302] by inhaling and exhaling through one embodiment of the invention. The information is combined with additional data from the patient, [1303] and that data is stored remotely The stored data may be combined with information from multiple patients for analysis.

Other embodiments are for the detection of biological or non-biological fluids.

Other embodiments of the system and sensing method as well as additional elements for use with embodiments described herein.

Figure 1:
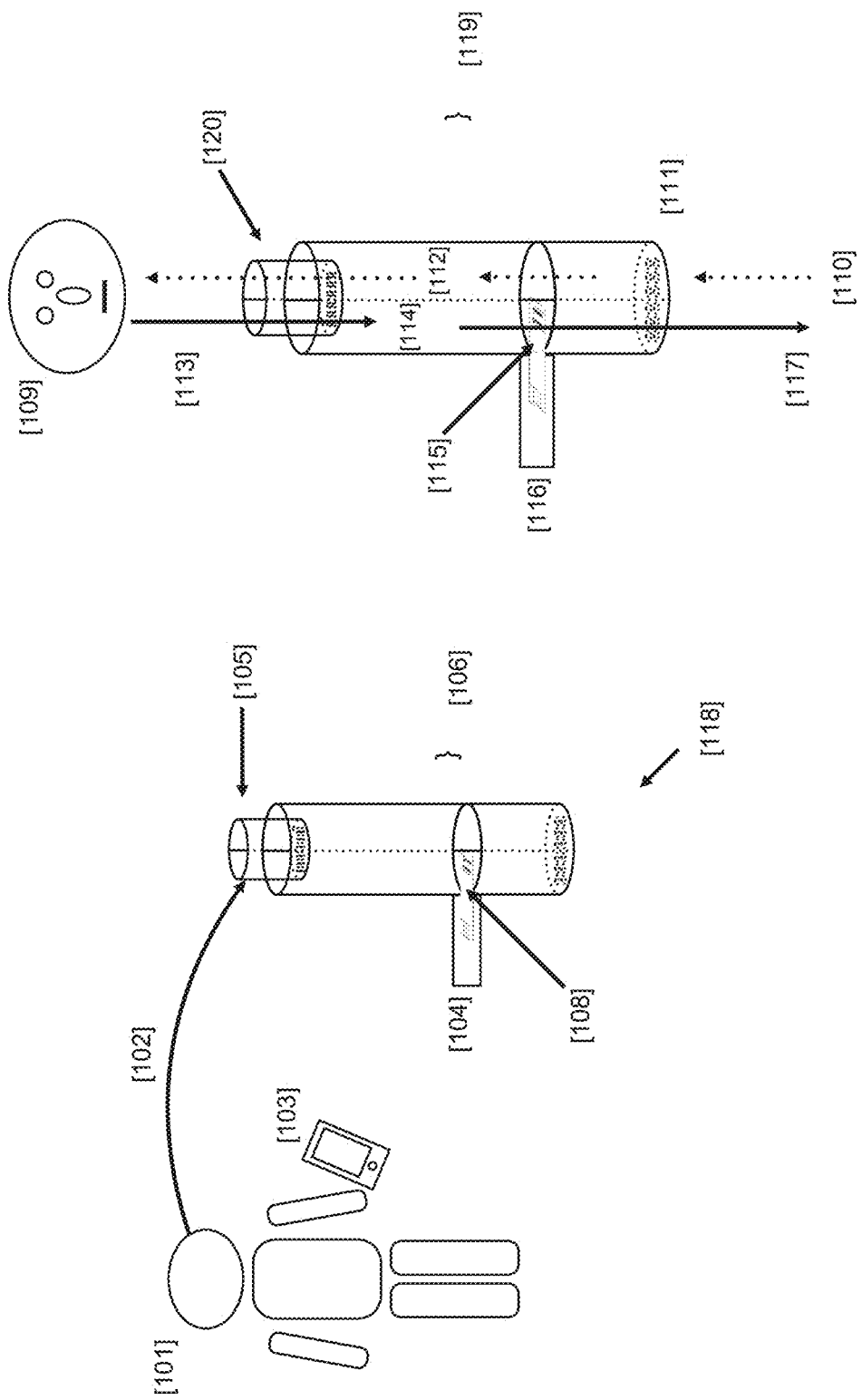
FIG. 1 is an example of the assembled device and test strip ready for use by a patient.

Embodiments of the invention may be configured in numerous ways without deviating from the spirit of the invention. Configurations may vary to optimize sensitivity and selectivity to the gas of interest, improve separation characteristics of the gases in the gas mixture, or improve patient experience and ease of use. FIG. 1 is an example of one configuration. The patient [101] inhales and exhales through the top of the device [102], and a signal is captured by an electronic device [103] in communication with the testing system [118]. The testing system [118] may be comprised of an optional, removable and/or disposable mouthpiece [105], a means of controlling and conditioning the gas flow [106], one or more test strips [108] placed inside the device, and an electronic device for interpreting the signal from the test strip [104]. The electronic device [104] may be in communication with another electronic device(s), such as a phone [103], tablet, or computer, either wirelessly, or via a wired connection. Other embodiments have the test strip [108] and electronic device [104] oriented vertically in the chamber designed to control and or condition the gas flow [106].

In one embodiment, a test strip [115] is connected to device reader [116] and placed inside the gas conditioning and flow control unit [119]. The patient [109] inhales through the mouthpiece [120] drawing air in through the bottom of the device [110]. The air may be conditioned in a chamber [112] to remove the analyte gas or gases from the ambient air. The patient exhales [113] through the mouthpiece. The chamber [114] may be designed to control the flow rate to the test strip [115] and/or to mechanically induce a set flow rate from the patients' breath stream. The air may pass over the test strip [115] and out of the device [117], or a portion, or all, of the gas stream may be captured for immediate, or future analysis. In another embodiment a portion of the gas stream is diverted to the test strip as shown in FIGS. 24, 25, 26, 26a, and 26b.

FIG. 1a provides examples of variations of the assembled device and the test strip. The device [141] may incorporate a removable and/or disposable mouthpiece [131]. The unit for controlling and conditioning the gas stream [142] may be a single piece with a slot for test strip insertion [140] or multiple pieces [134 and 135] that are separable allowing for insertion of the test strip [133a] into the gas stream [143]. The unit for controlling and conditioning gas may be a single chamber or multiple chambers [114] [112]. The electrical device for reading the test strip output [132] may be in wired or wireless communication with a phone [138] or other device. In other embodiments the electronics handle the signal processing and display the result [139] or [137]. The test strip may be placed into the gas stream in any orientation. Horizontal [133a] and vertical [133c] test strip orientations are shown.

In another embodiment, one of the techniques to condition the gas flow [106] includes removing water vapor from the breath stream.

In another embodiment, water vapor is removed from the breath stream by interacting with a sulfonic acid group, or other similar hygroscopic, water sorbent, and humectant groups, such as silicates, phosphates, acrylic acids, ethylene oxide, and others known to those skilled in the art or with a commercially available water sorbent.

Figure 2:
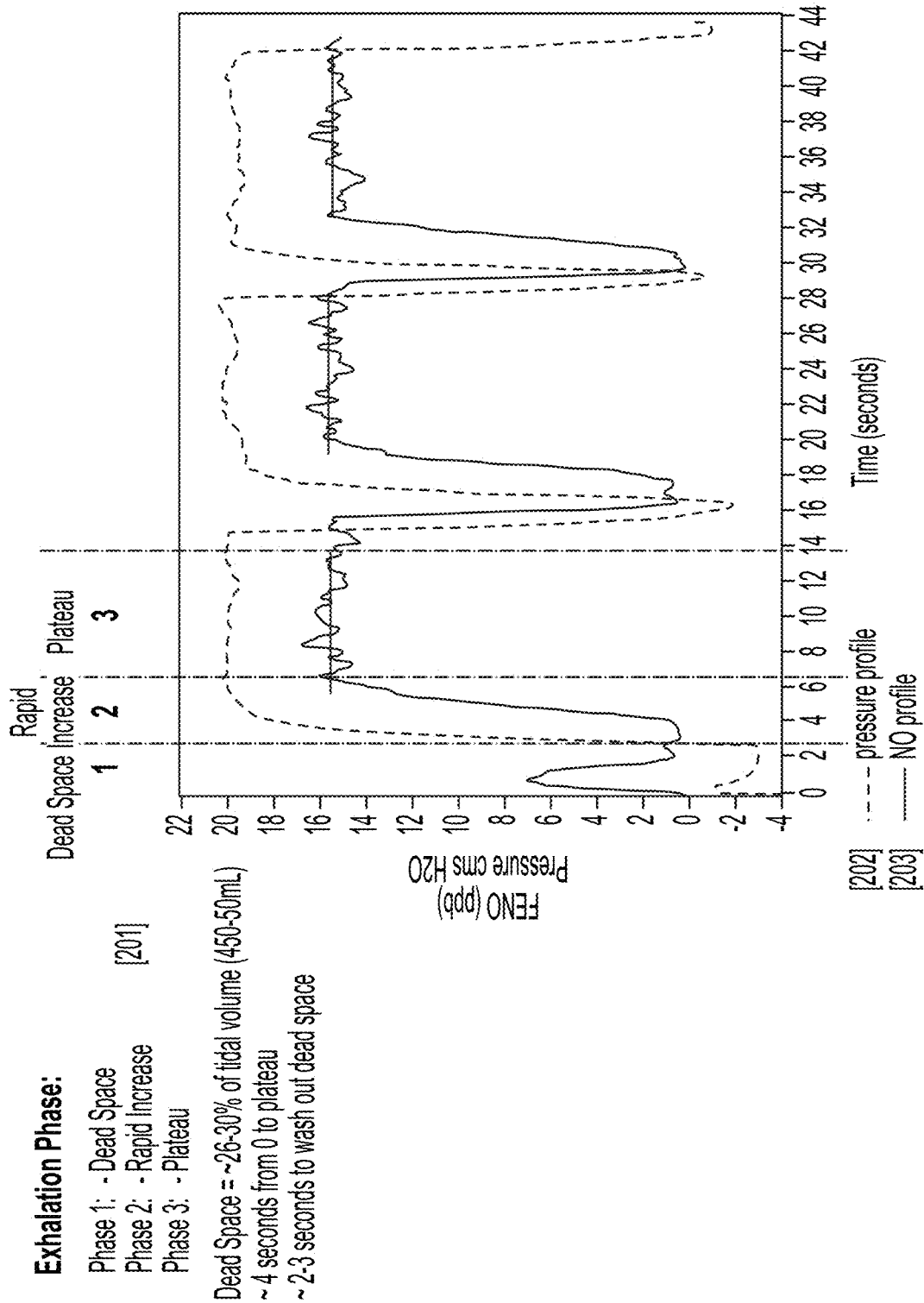
FIG. 2 is an example of the exhalation phases of human breath. Three exhalations are shown and the nitric oxide concentration is plotted versus pressure and time.

FIG. 2 shows a breath exhalation profile. Specifically, it demonstrates the three phases of exhalation [201] versus exhalation pressure [202] versus gas to be measured [203] versus time. It takes approximately 2-3 seconds to wash out the anatomical dead space (i.e. the gas in the airway that does not take part in respiration) and approximately 6 seconds to reach a plateau of gas concentration. Other exhaled gases besides nitric oxide (examples shown in FIG. 3) exhibit similar rapid increases and plateaus. In one embodiment, the test strip or system compensates for the phases of exhalation.

FIG. 3 is an example of the types and concentrations of gases expected in exhaled breath.

Various configurations or combinations of the substrate, electrode, and chemistry deposition are possible without deviating from the spirit of the invention. Configurations are dictated by the characteristics of the sensing chemistry, analyte of interest, and the environment in which the unit will be placed. Sensing chemistries may also be coated or covered to prevent analyte interaction, so as to provide a reference, as in a chemresistive bridge circuit. Multiple sensing chemistries may be used, or the same chemistry may be deposited more than once, to serve as a reference, for multiplexed analysis, or for signal averaging. Multiple chemistries that interact with the gas or gases of interest are possible without deviating from the spirit of the invention.

Figure 4:
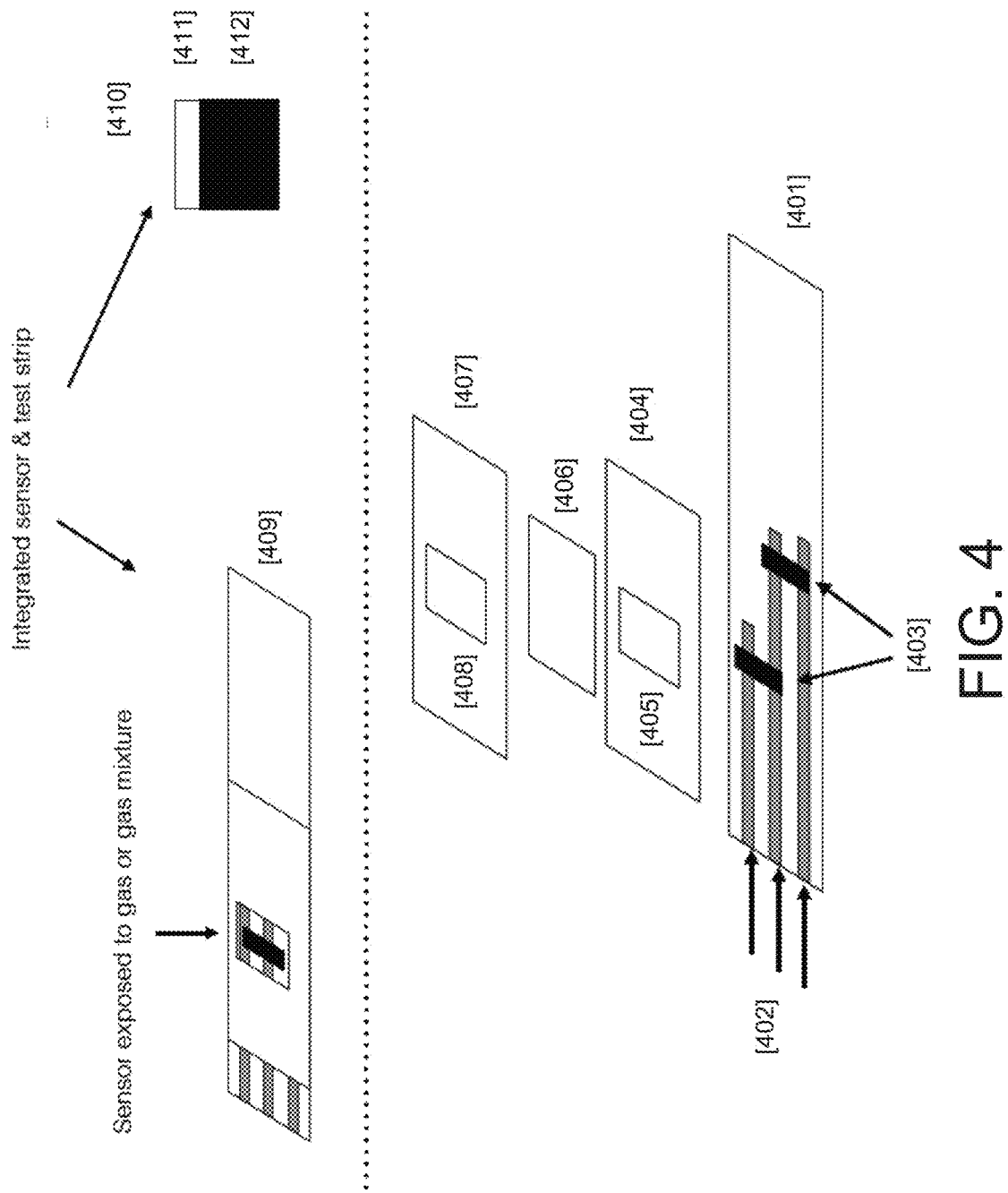
FIG. 4 is an example of a test strip with chromatographic layer and integrated sensor.

FIG. 4 demonstrates one embodiment of a test strip [409] configured to sense gas or gases utilizing a chromatographic separation layer. The test strip consists of a substrate [401], electrodes [402], dielectric layer (not shown), two sensing chemistries [403], a layer designed to cover one of the sensing chemistries and expose the second sensing chemistry [404], a chromatographic separation layer [406], a protective layer [407] with a window [408] to expose the sensor to the gas or gas mixture. The layers [404] and [407] may be processed in many ways to create openings [408] and [405] that expose one of the chemistries for sensing. Examples of processing include but are not limited to die cutting or laser cutting. The layers [404], [406], [407] may be processed in many ways prior to laminating the layers together in a test strip. Examples of processing include but are not limited to die cutting, laser cutting, kiss cutting, surface energy modification (UV radiation, plasma and corona discharge or by flame or acid treatments or other techniques known in the art.), spray treatment with adhesive etc.

A cross-sectional view is shown in another embodiment [410], in which the chromatographic layer [411] is integrated with a metal oxide semiconducting sensor [412]. Other type of sensors may be utilized without deviating from the spirit of the invention. Examples include but are not limited to: electrochemical, MEMS, FET, MOSFET, optical and ChemFET sensors. Examples of suppliers include but not limited to: Figaro, Honeywell, Texas Instruments, Analog Devices, Applied Sensors, and SGX Sensor Tech.

In one embodiment, the test strip does not have a dielectric layer.

In another embodiment, the test strip has a single (1) sensing chemistry.

Figure 4A:
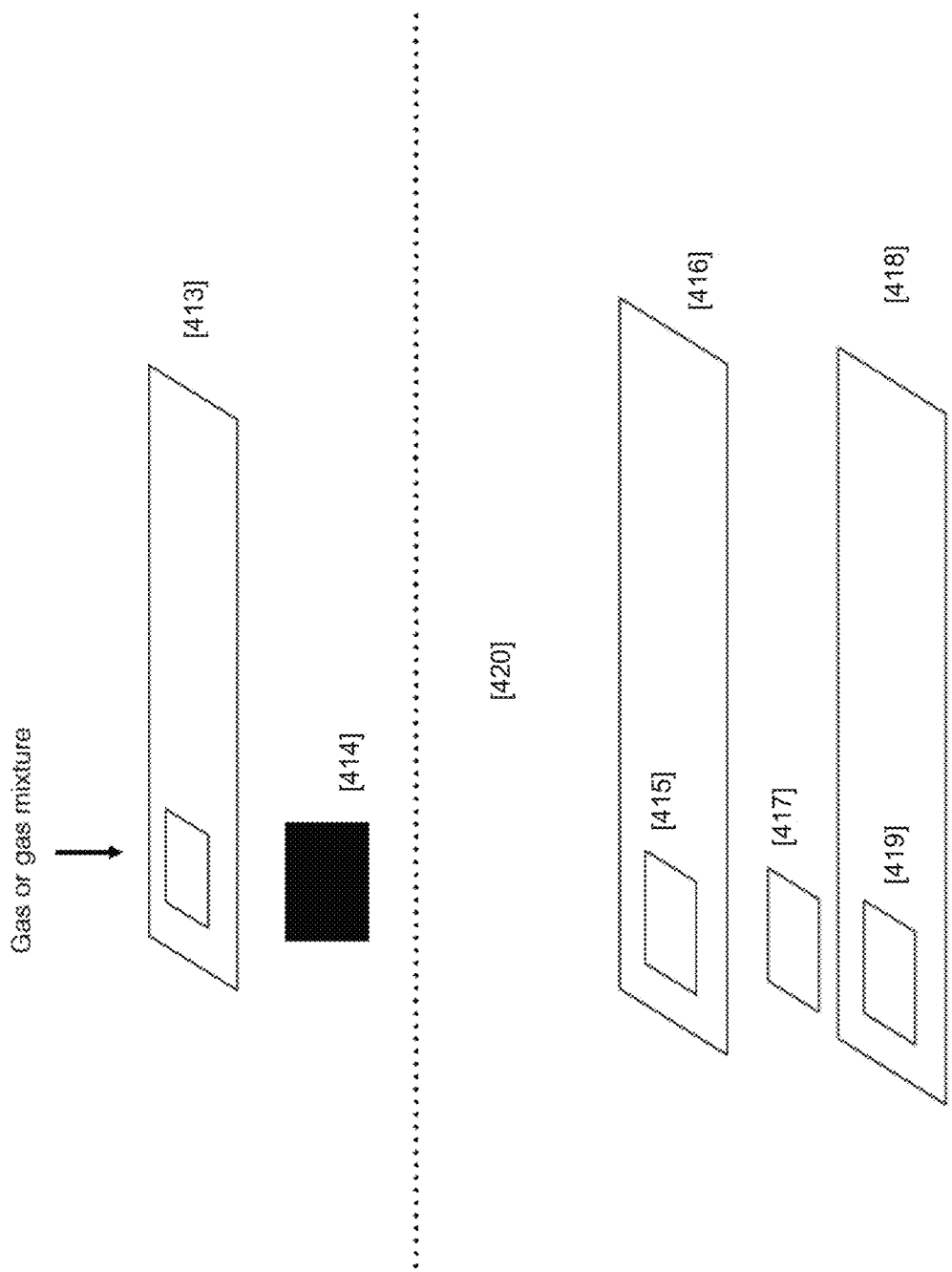
FIG. 4a is an example of a test strip with chromatographic layer and non-integrated sensor

In another embodiment, the test strip only serves as a chromatographic layer and does not contain a sensing element (FIG. 4a). In this embodiment, the test strip with chromatographic layer [413] is used in conjunction with one of the types of sensors [414] previously described. The test strip [413] may be single use, multi-use or limited use. It may be disposable or reusable. It may also be single patient use. One embodiment of a test strip that only serves as a chromatographic layer is shown [420]. In this embodiment, the chromatographic layer [417] is layered in-between two substrates [416] and [418]. The substrates may contain windows [415] and [419] to allow gas to pass through the chromatographic layer [417]. Other substrate configurations are possible without deviating from the spirit of the invention. Examples include but are not limited to substrates that provide structural support for the chromatographic layer or are used to integrated the chromatographic layer with a sensor or device.

Figure 4B:
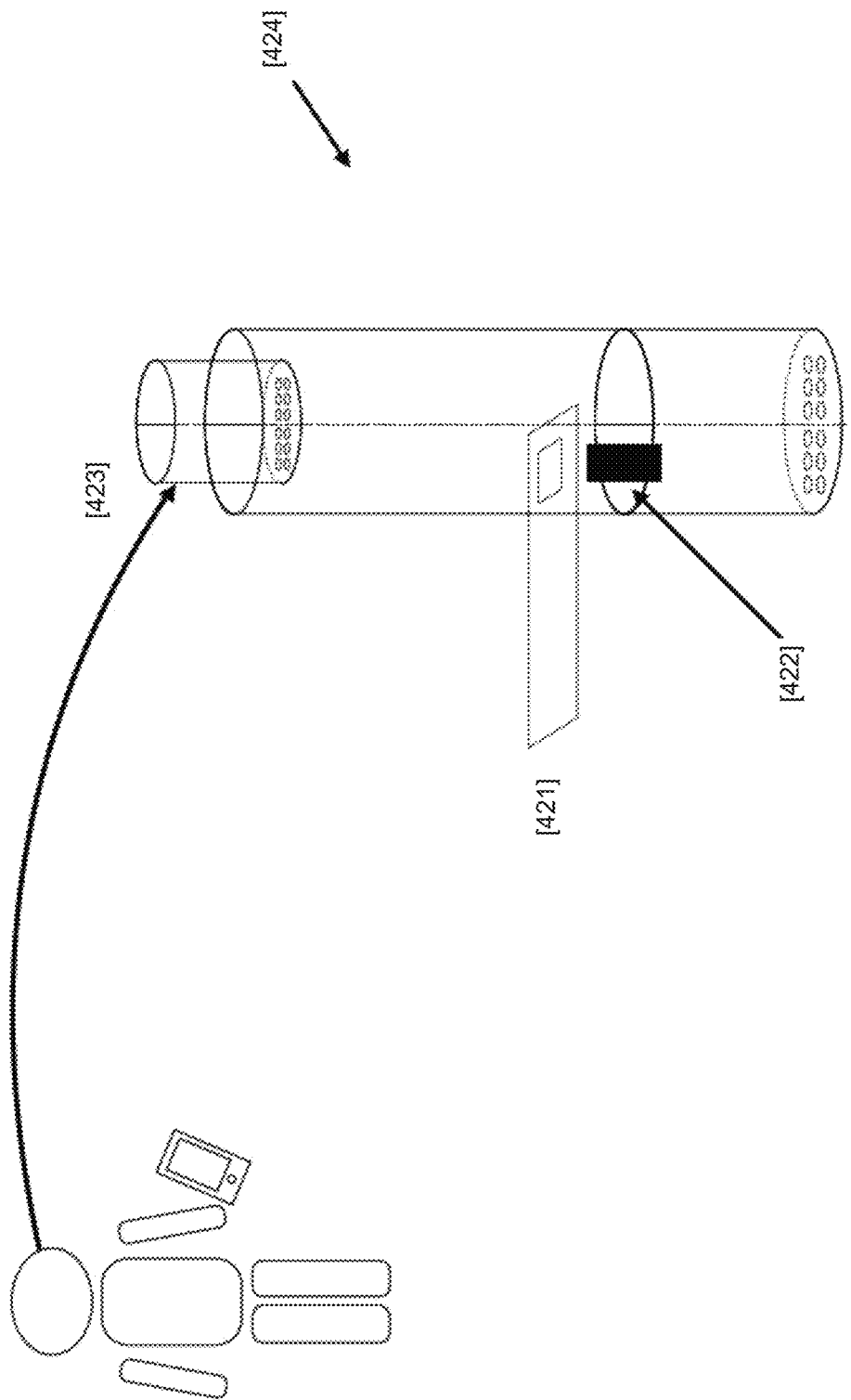
FIG. 4b is an example of an assembled device and test strip with chromatographic layer and non-integrated sensor.

FIG. 4b demonstrates one embodiment of a system similar to FIG. 1. In FIG. 4b, the test strip with chromatographic layer [421] is inserted into a device [424]. The Patient exhales through the device [423] and the gas passes through the chromatographic layer to the sensor [422]. In this embodiment, the sensor may be a metal oxide semiconducting sensor or one of the other sensing technologies previously discussed.

The chromatographic diffusion and/or permeation layer may consist of a impregnate, may be comprised of porous and non-porous polymers, composite materials, fibrous materials such as paper or fiber glass, woven and non-woven textiles, membranes, polymers, adhesives, films, gels, etc. The layer or layers may be modified, for example, by chemically treating or coating and/or mechanically altering its surface. Other examples of materials suitable for chromatographic layers are incorporated herein (Test Strip— Layers). The layer may contain additional materials or undergo additional processing to make it suitable for manufacturing.

In one embodiment, the chromatographic layer is made up of silicone or a membrane or film containing silicone. In one embodiment, its thickness is between 1 µm and 200 µm for fast analysis. In another embodiment the thickness is greater than 200 µm for delayed analysis (hours or days). In another embodiment the thickness is greater than 1 inch for analysis over a period of days, weeks or years.

In another embodiment, the chromatographic layer is treated with a material to selectively remove chemicals and/or water (including water vapor). Treatment includes but is not limited to coating, spraying, chemically bonding etc.

In another embodiment, the chromatographic layer is treated with Nafion.

In another embodiment, the chromatographic layer is treated with a sulfonic acid.

In another embodiment, the chromatographic layer contains silicone and Nafion.

In another embodiment, the chromatographic layer contains silicone and sulfonic acid.

In another embodiment, one of the test strip layers contains sulfonic acid or Nafion.

In another embodiment, the chromatographic layer may contain sorbent particulates to modify the chromatographic properties, such as activated carbon, functionalized silica, alumina, clays, diatomaceous earth, mineral carbonates, polymers, and other filler materials known to those skilled in the art.

In another embodiment, the chromatographic layer may contain emulsified components to modify the chromatographic properties, such as emulsified water, oils, gases, organic solvents, polymers, organic molecules, and other biphasic chemicals known to those skilled in the art.

Chromatographic Detection

The gas detection method referenced hereafter is based on the selective diffusion and/or permeation properties of a chromatographic layer. The method utilizes at least one of the following methods to separate and analyze the concentration of a single gas or multiple gases: the physical and chemical properties of the material, thickness of material, time, signal strength/magnitude, and/or signal slope, change from a single baseline and/or change versus multiple baselines, overshoot and/or under shoot versus a fixed point (e.g. the baseline). Utilizing multiple methods in combination is also possible without deviating from the spirit of the invention. The method improves sensitivity and selectivity of the sensor and allows for complex multiplexing from a single chemistry. Gas, including water vapor, passing through the chromatographic layer shall hereafter incorporate this method.

In one embodiment, the test strip is calibrated to the gas or gases of interest. The test strip may also be calibrated versus gases that have the potential to interfere with the gas of interest. Calibration may include the linearization of sensor signal to one or multiple gases to convert the signal to a quantity (e.g. part per billion or part per million) of analyte.

In one embodiment the sensor and/or sensing chemistry is designed to have a differential response to the gas of interest and to interfering gases.

In another embodiment, the chromatographic layer is designed to provide both separation and specificity to the sensor and/or sensing chemistry.

Figure 5:
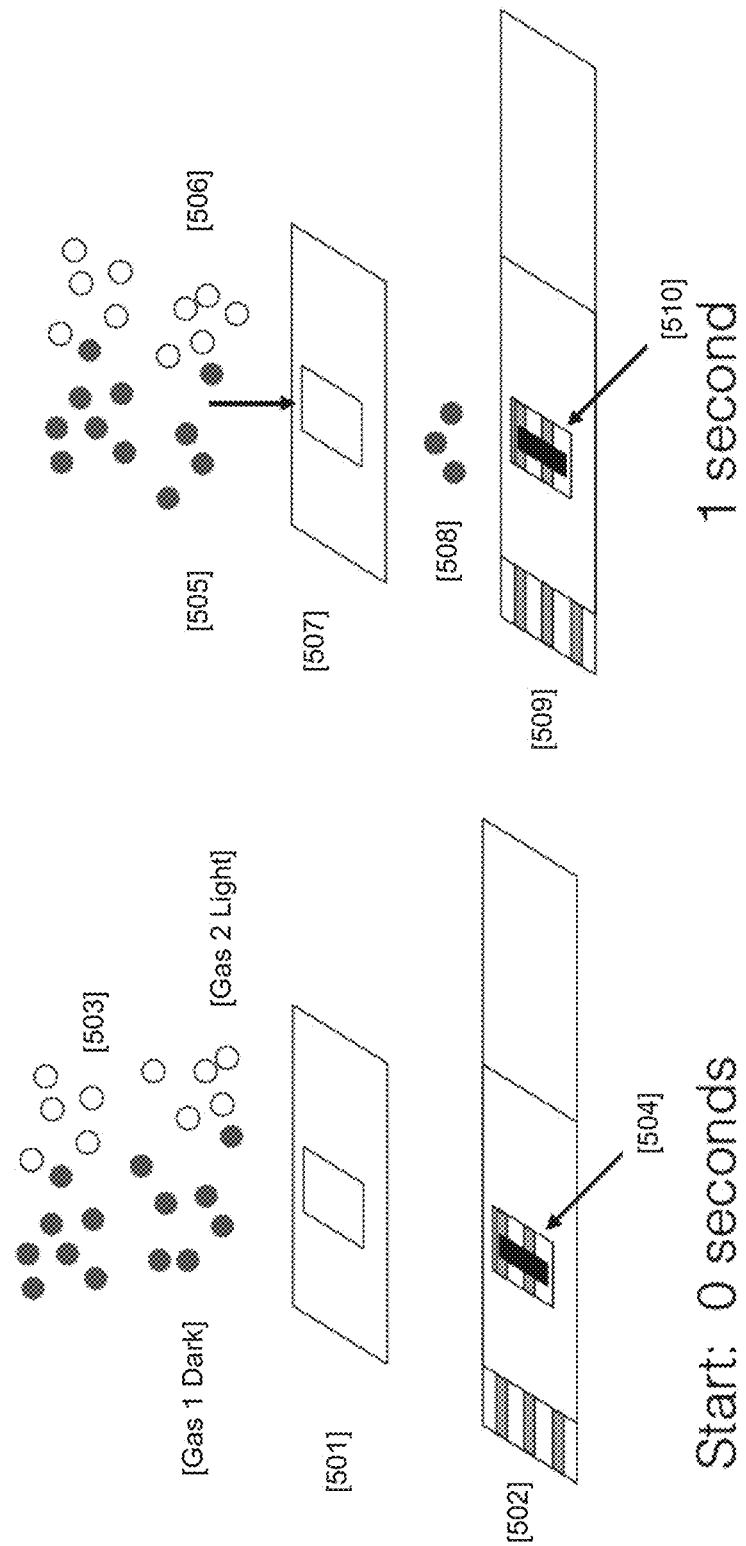
FIG. 5 is an example of a mixed gas sample arriving at the test strip, above the chromatographic layer, and beginning passing through the chromatographic layer to the sensor.
Figure 5A:
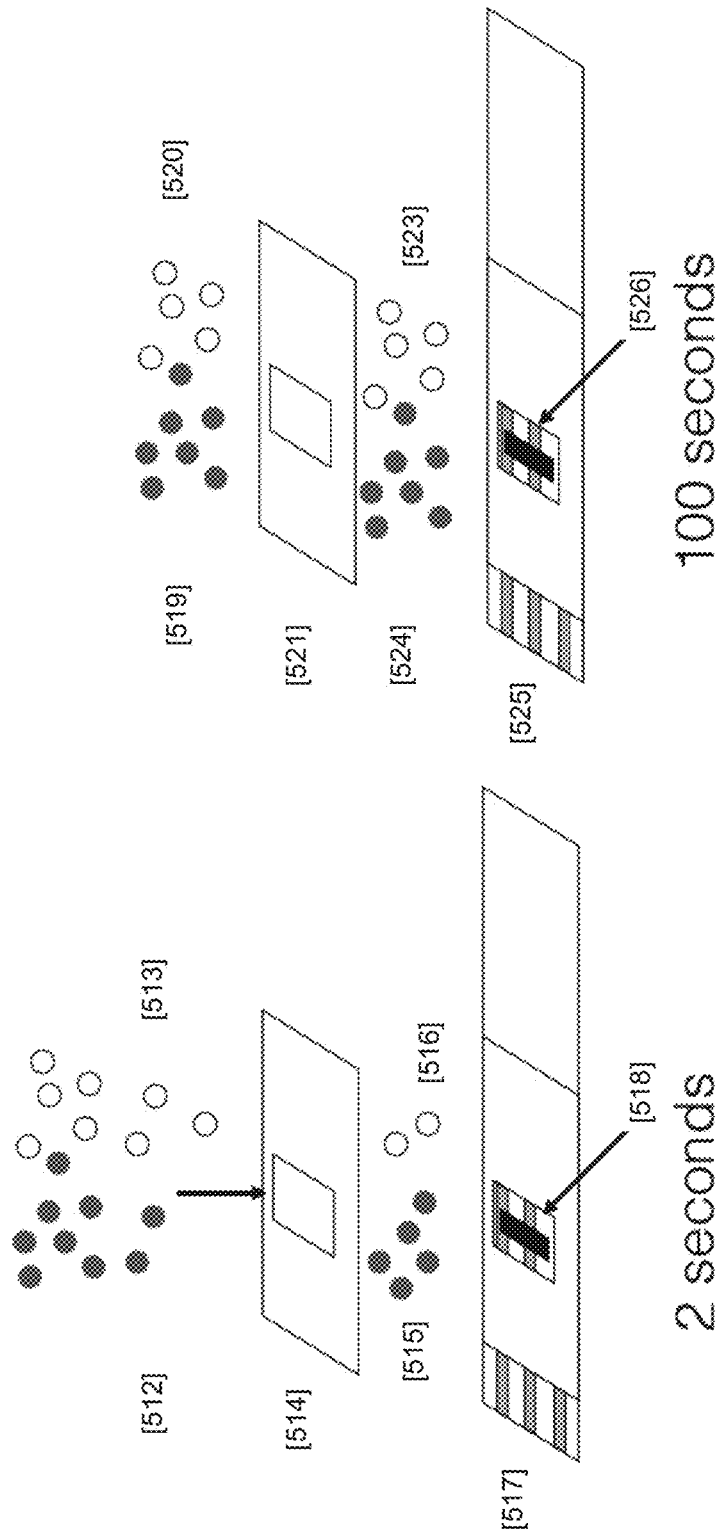
FIG. 5a is a continuation of the example from FIG. 5.

FIG. 5 depicts a test strip [502] with its chromatographic layer [501] separated for illustrative purposes with a mix of gas molecules [503] above the chromatographic layer. Two molecules are depicted but any number of molecules is possible without deviating from the spirit of the invention. As time passes, the gas above the chromatographic layer begins to pass through the layer. The properties of the chromatographic layer create a time-based separation so that gas selectively and predictively passes through the layer to the sensing chemistry for detection. In one embodiment, shown in FIG. 5, Gas 1, represented by dark circles, and Gas 2 represented by light circles (collectively [503]) arrive to the test strip [502] above the chromatographic layer [501]. At zero seconds, the initial condition, 0% of Gas 1 and 0% of Gas 2 are on one side of the chromatographic layer. After 1 second, ~43% of Gas 1 [505] and [508] required to reach equilibrium has passed through the chromatographic layer [507], while 0% of Gas 2 [506] required to reach equilibrium has passed through. At 2 seconds (FIG. 5a), Gas 1 [512] and [515] is at 71% equilibrium concentration on the sensor side of the chromatographic layer [514] and Gas 2 [513] and [516] is at ~40% equilibrium. At some point in time, 100 seconds in this example, both Gas 1 [519] and [524] and Gas 2 [520] and [523] are at 100% of their equilibrium value below the chromatographic layer [521] at the level of the test strip [525].

Figure 6:
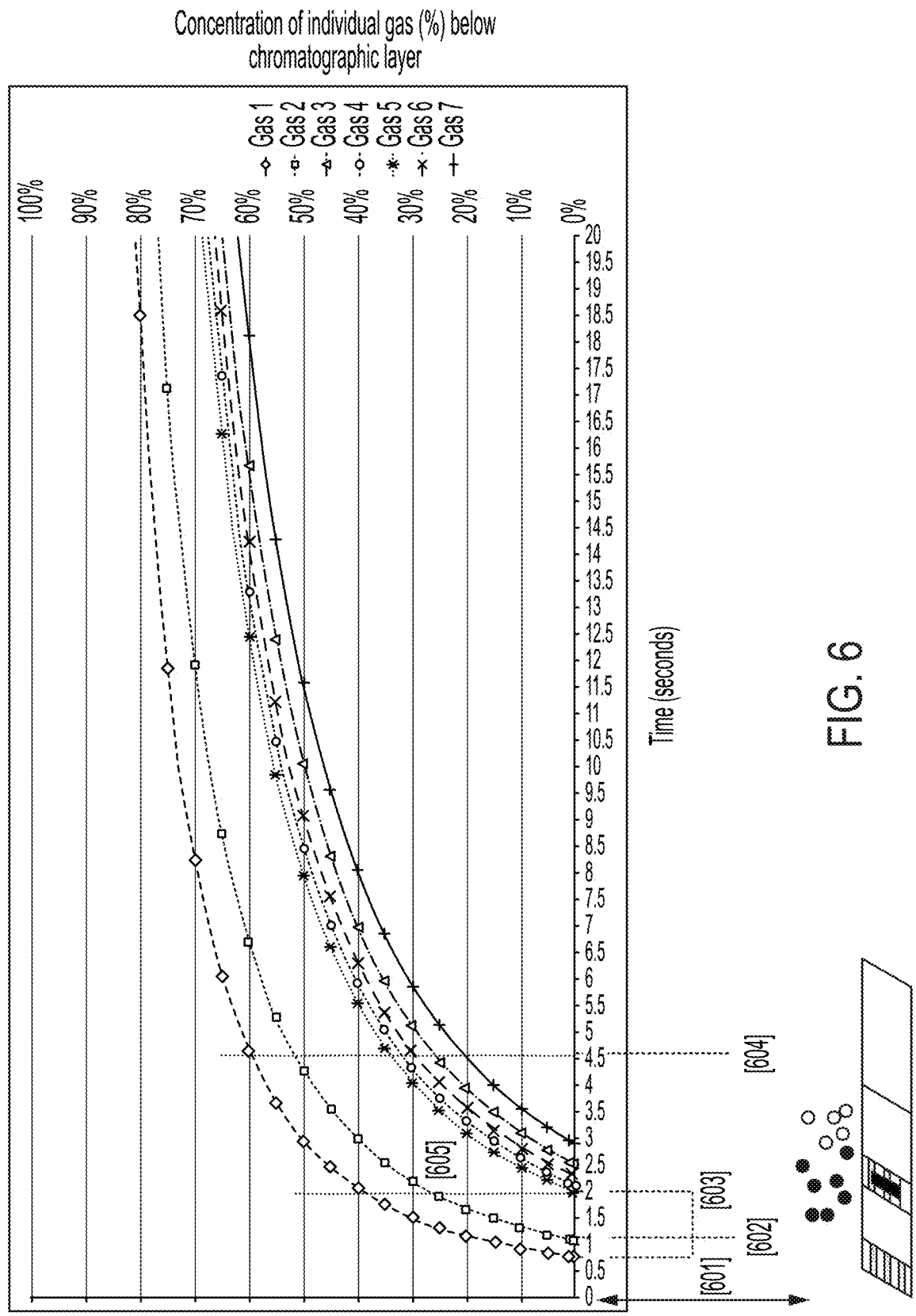
FIG. 6 shows a detailed explanation of a 7 gas mixture and percentage of gas diffused through chromatographic separation layer versus time.

FIG. 6 shows the gas-time separation provided by the chromatographic layer that contains silicone at 100 µm thick. In this example, each gas is plotted individually from the gas mixture and is expressed in relation to its own equilibrium concentration (i.e. at time 0, 100% of the individual gas is above the chromatographic layer and at time >0, a certain percentage of the individual gas has passed through the chromatographic layer to approach the equilibrium value). In FIG. 6, the gas arrives above the chromatographic layer of the test strip at time 0 [606]. At 0.75 seconds [601] the first molecules of Gas 1 pass through the chromatographic layer and arrives at the surface of the sensor. At 1 second [602], the first molecules of Gas 2 pass through the chromatographic layer and arrive at the sensor. At 2 seconds [603] Gas 5 begins to pass through the chromatographic layer. Over various time intervals between 2 and 3 seconds, the remaining gases begin to pass through the chromatographic layer. Eventually, after enough time passes, all of the gases will reach 100% of their equilibrium concentration below the chromatographic layer (not shown in FIGS. 6, 8, 9, 10, 11). Any number of gases is possible without deviating from the spirit of the invention.

The sensor or detector placed adjacent to the chromatographic layer may be any number of gas or liquid sensing apparatuses, whereby the signal may be, but is not limited to, optical, acoustic, mechanical, or electronic. Other embodiments are possible without deviating from the spirit of the invention, such as those set forth elsewhere herein.

The signal produced by the sensor at 1 second [602] is 20% of the equilibrium concentration of Gas 1 versus 0% of Gases 2 through 7. At 2 seconds [603] the signal produced by the sensor is 35% of the equilibrium concentration of Gas 1 versus 25% of the equilibrium concentration of Gas 2 versus 0% of Gases 3, 4, 5, 6 and 7. At 4.25 seconds [604] the signal produced by the sensor is approximately 58% of Gas 1 versus 50% of Gas 2 versus less than 40% of Gas 3 through 7 and so on. Any number of gases is possible without deviating from the spirit of the invention.

In one embodiment, the concentrations of Gas 1 and Gas 2 can be determined by comparing the signal to a calibration table at a given time before other gasses have passed through chromatographic layer. The signal may be determined from a baseline reading as the test strip acclimates to its environment.

In another embodiment, the concentration of Gas 2 may be determined by enhancing the sensing chemistry to respond more favorably to Gas 2 than to Gas 1. The system may be calibrated to detect a signal of Gas 2 against a mixture of Gas 1 or other gases that pass through the chromatographic layer before Gas 2. At a given time, for example 2 seconds in FIG. 6, the signal represents 25% of the total concentration of Gas 2 against a background of only Gas 1. The total concentration of Gas 2 may be determined by comparing the signal at 25% to a linear output of 100% of the signal in a calibration table.

In one embodiment, the test strip and sensing system is calibrated to the gases found in exhaled human breath.

In one embodiment, the test strip and sensing chemistry is calibrated against a background of at least one of the gases found in exhaled human breath, including water vapor.

In another embodiment, the test strip and sensing chemistry is designed to have a differential response to water vapor and the gas of interest.

Figure 7:
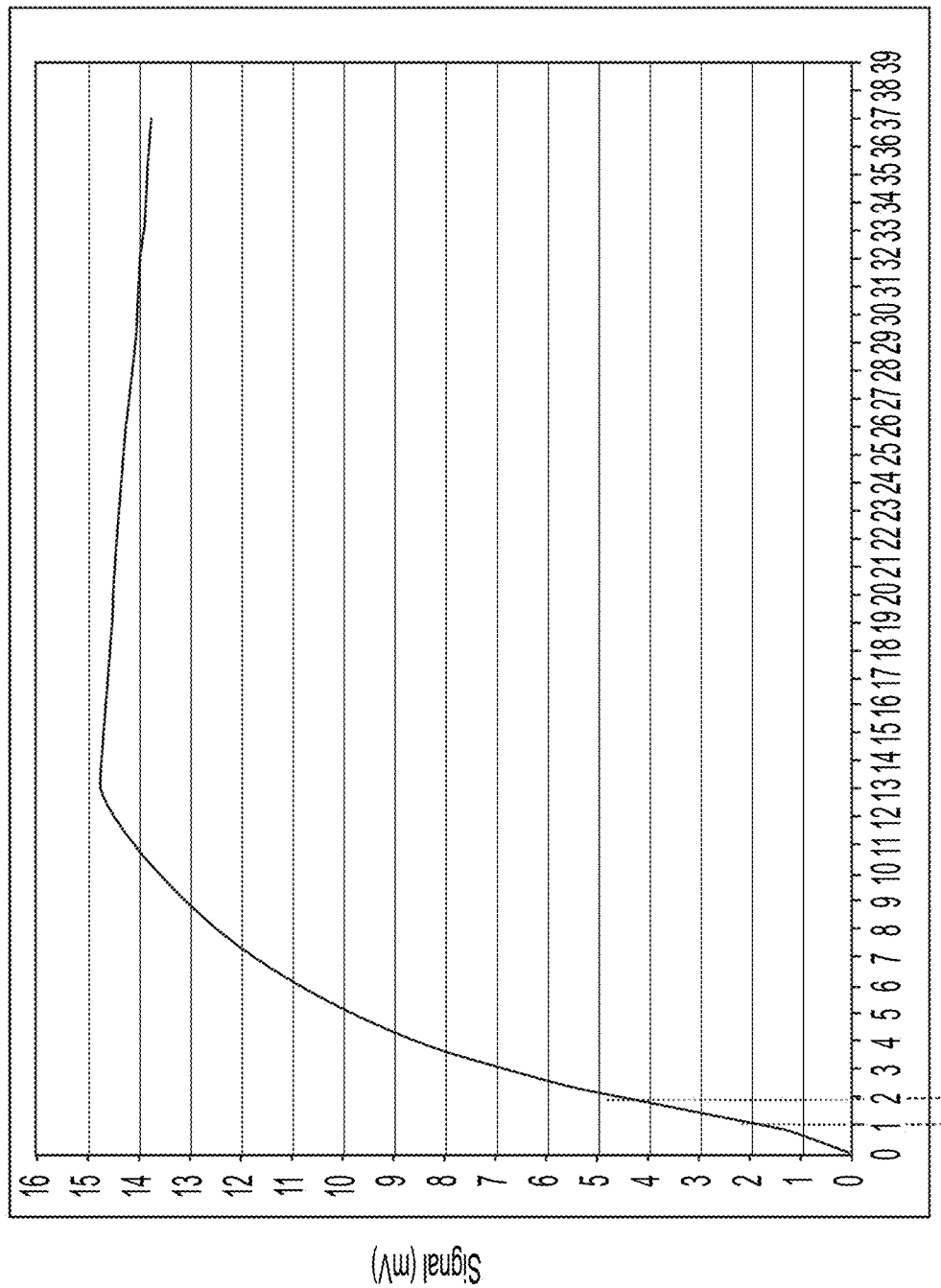
FIG. 7 demonstrates a single breath profile versus time on a test strip utilizing a chromatographic layer.
Figure 7A:
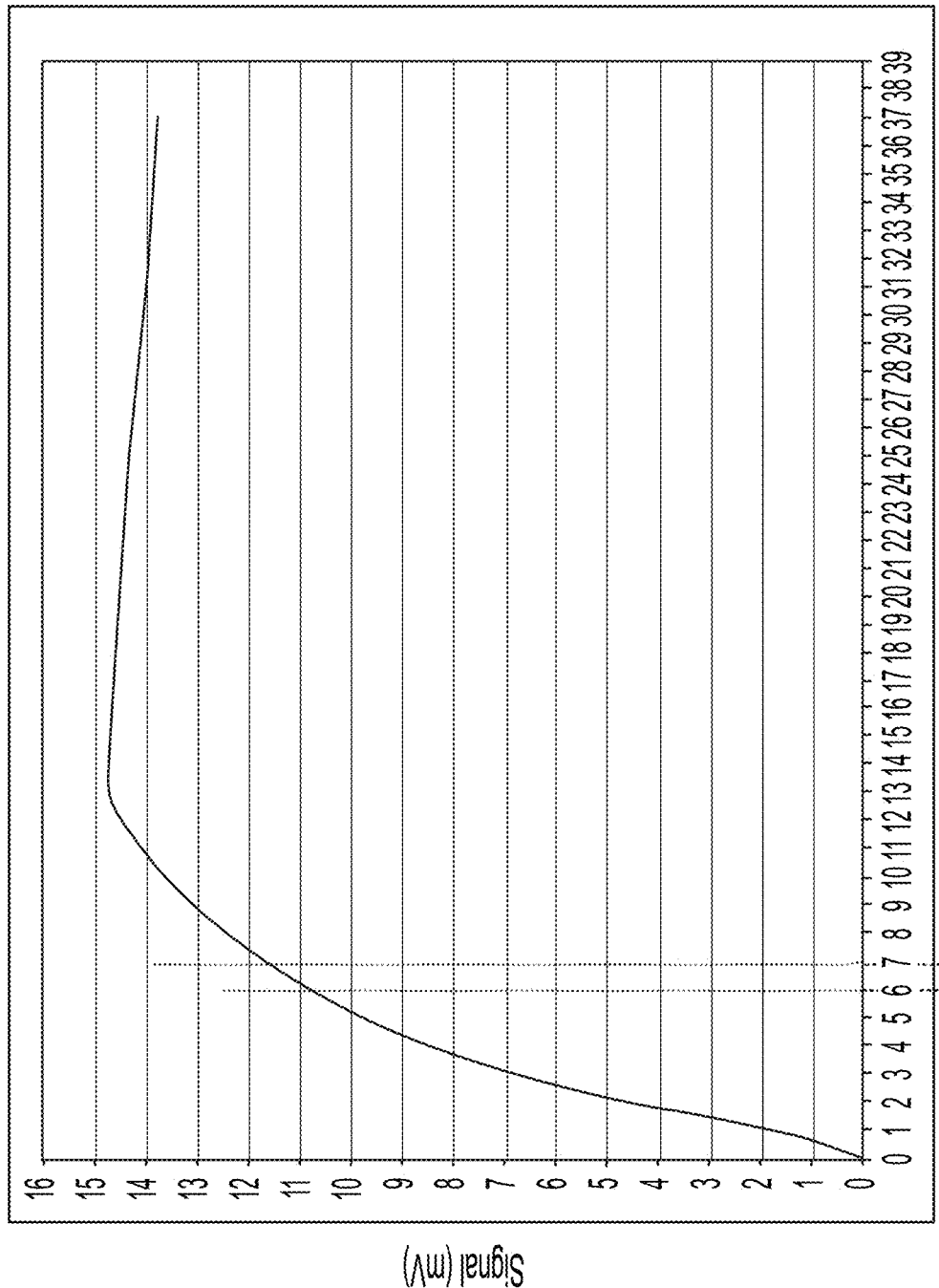
FIG. 7a shows points in time where a signal may be sampled from a single breath profile.
Figure 8:
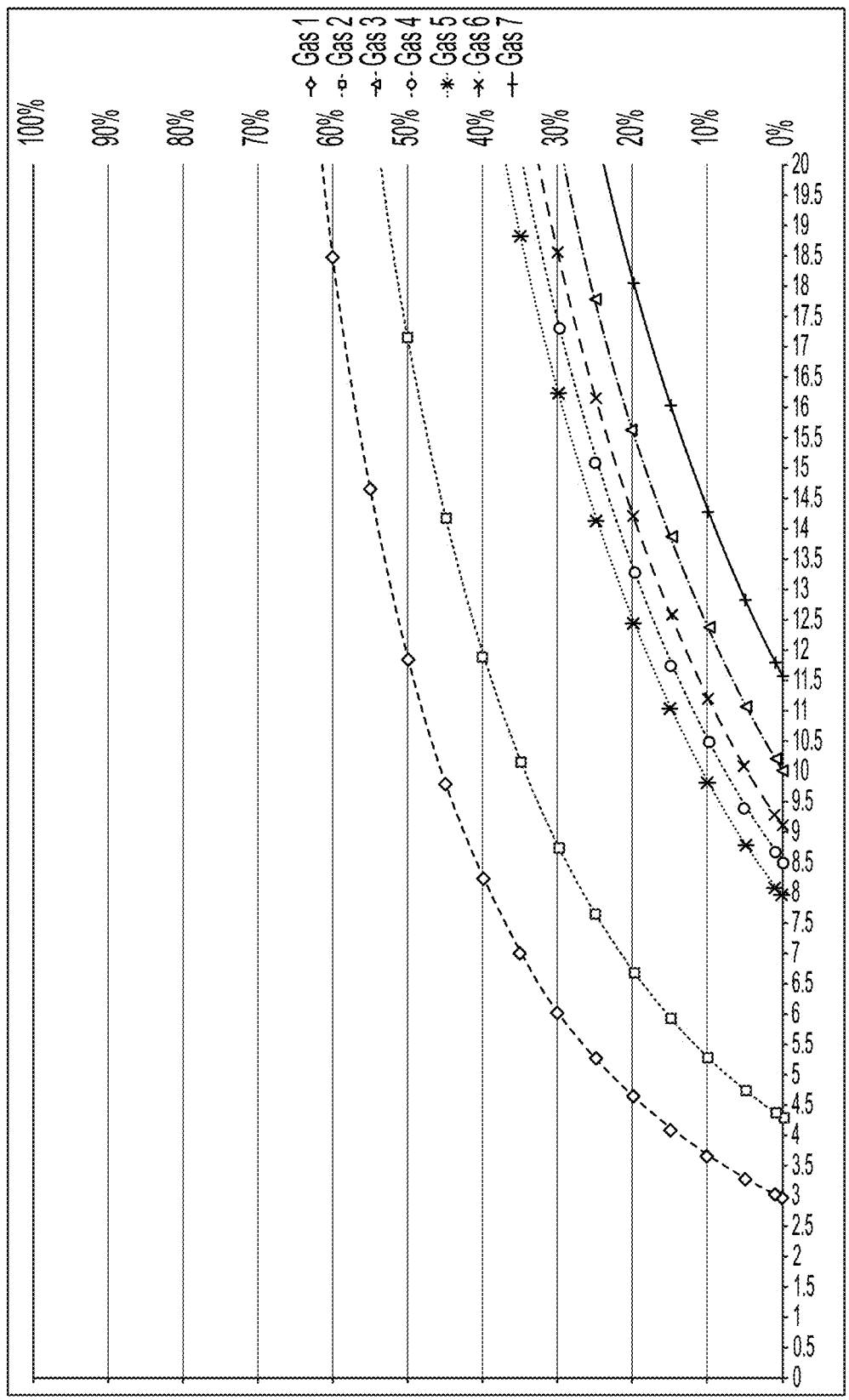
FIG. 8 demonstrates the gas separation of a 200 um thick chromatographic layer expressed as concentration of gas below the layer versus time.
Figure 9:
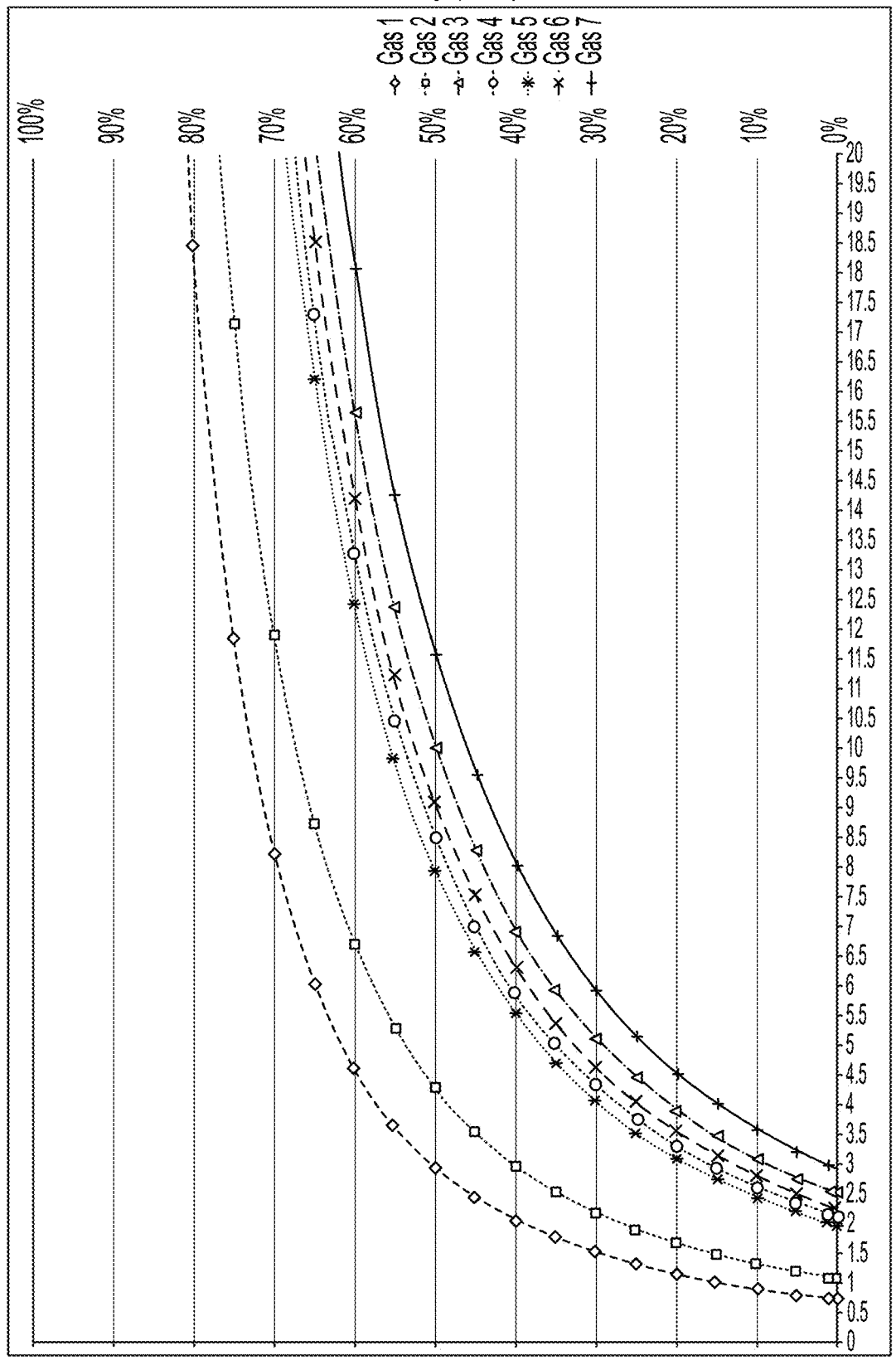
FIG. 9 demonstrates the gas separation of a 100 um thick chromatographic layer expressed as concentration of gas below the layer versus time.
Figure 10:
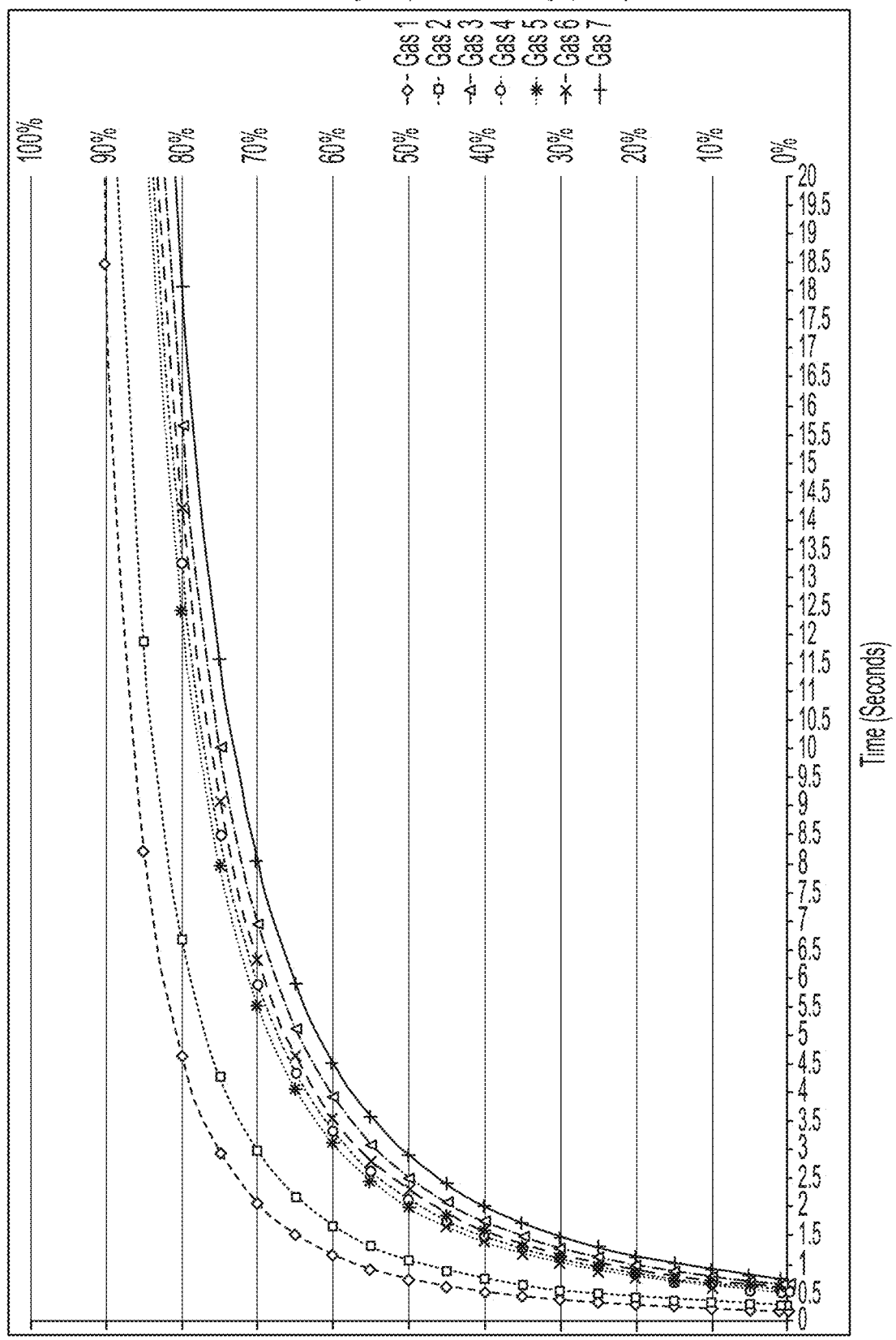
FIG. 10 demonstrates the gas separation of a 50 um thick chromatographic layer expressed as concentration of gas below the layer versus time.
Figure 11:
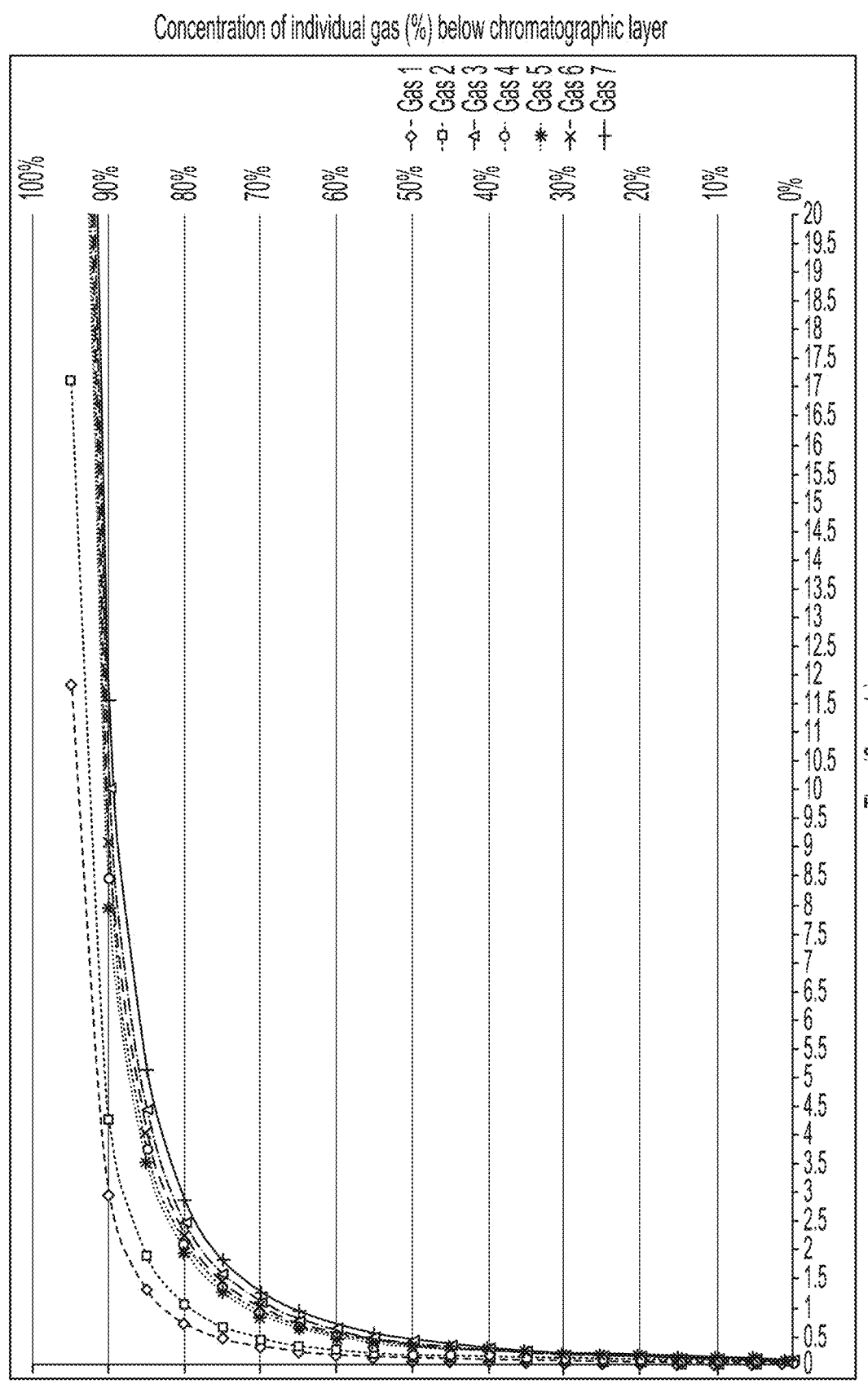
FIG. 11 demonstrates the gas separation of a 20 um thick chromatographic layer expressed as concentration of gas below the layer versus time.

FIG. 7 and FIG. 7a demonstrate a single breath profile versus time as recorded and plotted by the sensor with a 100 μm chromatographic layer. The signal represents a relative measurement (e.g. a change expressed in millivolts vs. time) from a baseline measurement. The millivolt signal is compared to a calibration table for quantitative and/or qualitative analysis (e.g. signal equals 10 parts per billion of nitric oxide or the signal is <20 parts per billion of nitric oxide). In this example the gas mixture contains the gases found in FIG. 3 arrive at the test strip at Time 0. The gas of interest to be detected is nitric oxide. At 1 second [701], nitric oxide begins to pass through the chromatographic layer. At two seconds [702], the signal is 4.75 mv which can be translated in a part per billion quantity. In one embodiment, measurements of the signal are sampled at various time [701], [702], [703], [704] to determine the quantity of a second gas or gases and/or confirm the initial signal sampled.

In one embodiment a baseline is taken to confirm the accuracy (e.g. quality control check) of the test strip prior to introduction of the gas sample.

In one embodiment, the gas sample interacts with the test strip and sensing chemistry, further described herein, changing the resistance or other electrical property of the sensor which is measured and displayed, for example, in millivolts.

In one embodiment, a known current is passed through the test strip electrodes to perform the resistive or voltage measurements.

In one embodiment, resistance is measure directly.

In one embodiment, the current passed through the test strip electrodes is pulsed.

In one embodiment, the signal is converted into the frequency domain.

In another embodiment, the test strip and sensing system measures liquids.

In another embodiment, the test strip and sensing system measures biological fluids.

In another embodiment, the test strip and sensing system measures breath condensation.

In another embodiment, the system is calibrated to each of the gases in the expected gas stream individually and in relation to one another. The signals of each gas are linearized and the concentration or concentrations can be determined at a given point in time.

In another embodiment, a gas that passes slowly through the chromatographic layer is the gas of interest. For example, in FIG. 6, Gas 3 is the gas of interest and the signal of Gas 1 and Gas 2 is subtracted or re-baselined at each point in time until a given percentage of Gas 3 has passed through the chromatographic layer. In some embodiments, the information used to re-baseline at each point in time is determined empirically on gas mixtures having known concentrations of known gases.

In another embodiment, increasing or decreasing the temperature of the environment on or near the test strip is utilized to change the properties of gas separation.

In another embodiment, the test strip itself is heated or cooled.

In another embodiment, the concentration of a gas is determined before other gases arrive at the sensor (i.e. pass through the chromatographic layer).

Measuring any gas in the gas mixture, regardless of when it passes through the chromatographic layer, is possible without deviating from the spirit of the invention.

FIGS. 8, 9, 10, 11 demonstrate time separation of the chromatographic layer at various thicknesses. The figures show the concentration of individual gases, expressed as a percentage diffused through the chromatographic layer [406], plotted versus time. In these figures, the gas arrive above the chromatographic layer at time 0.

Figure 12:
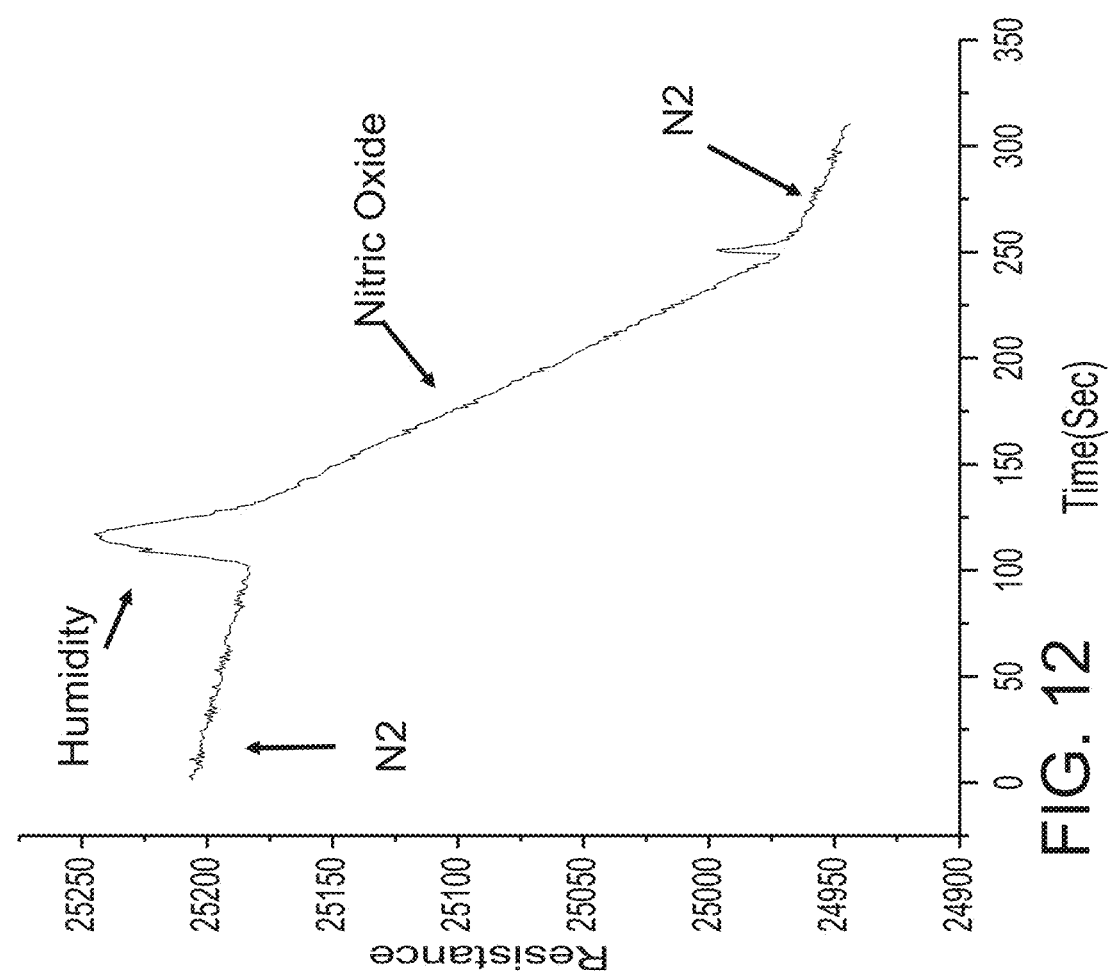
FIGS. 12, 12a, 12b, and 12c demonstrate a multi gas signal from the senor.

FIG. 12 represents the signal output of one embodiment of a test strip with chromatographic layer. The sensor is placed in a stream of nitrogen then exposed to a mixed gas stream consisting of humidity and nitric oxide. Humidity is the first gas to pass through the chromatographic layer and causes an increase in resistance of the sensor. Nitric oxide then follows and causes a sharp decrease in resistance until nitrogen is re-introduced.

Figure 12A:
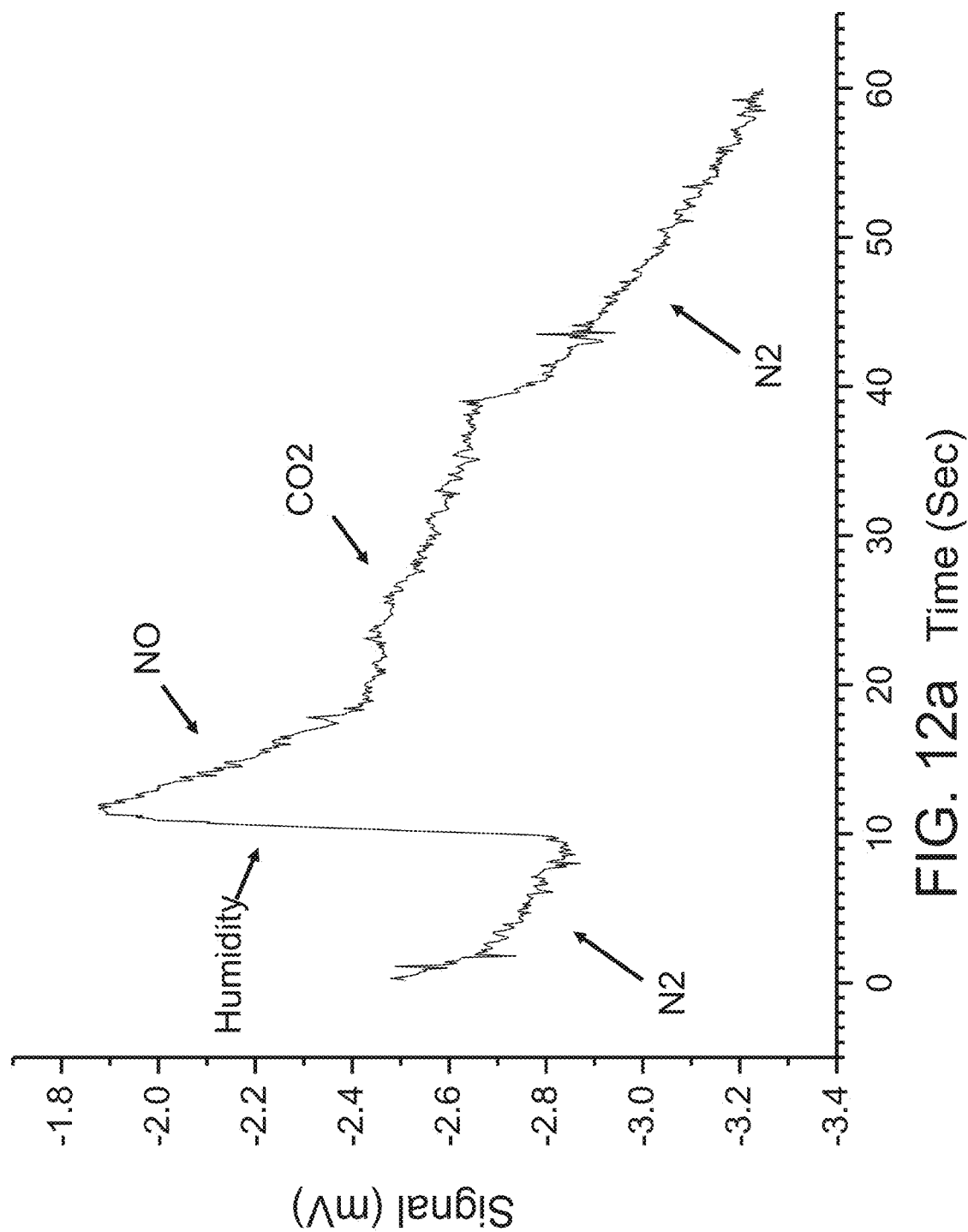

FIG. 12a demonstrates another embodiment of the signal output of the test strip with chromatographic layer. The sensor is placed in a stream of nitrogen then exposed to a mixed gas stream consisting of humidity, nitric oxide and carbon dioxide. Humidity is the first gas to pass through the chromatographic layer and causes an increase in resistance of the sensor. Nitric oxide then follows and causes a sharp decrease in resistance. Carbon dioxide is the third gas to pass through the layer causing a change in slope until nitrogen is re-introduced.

Figure 12B:
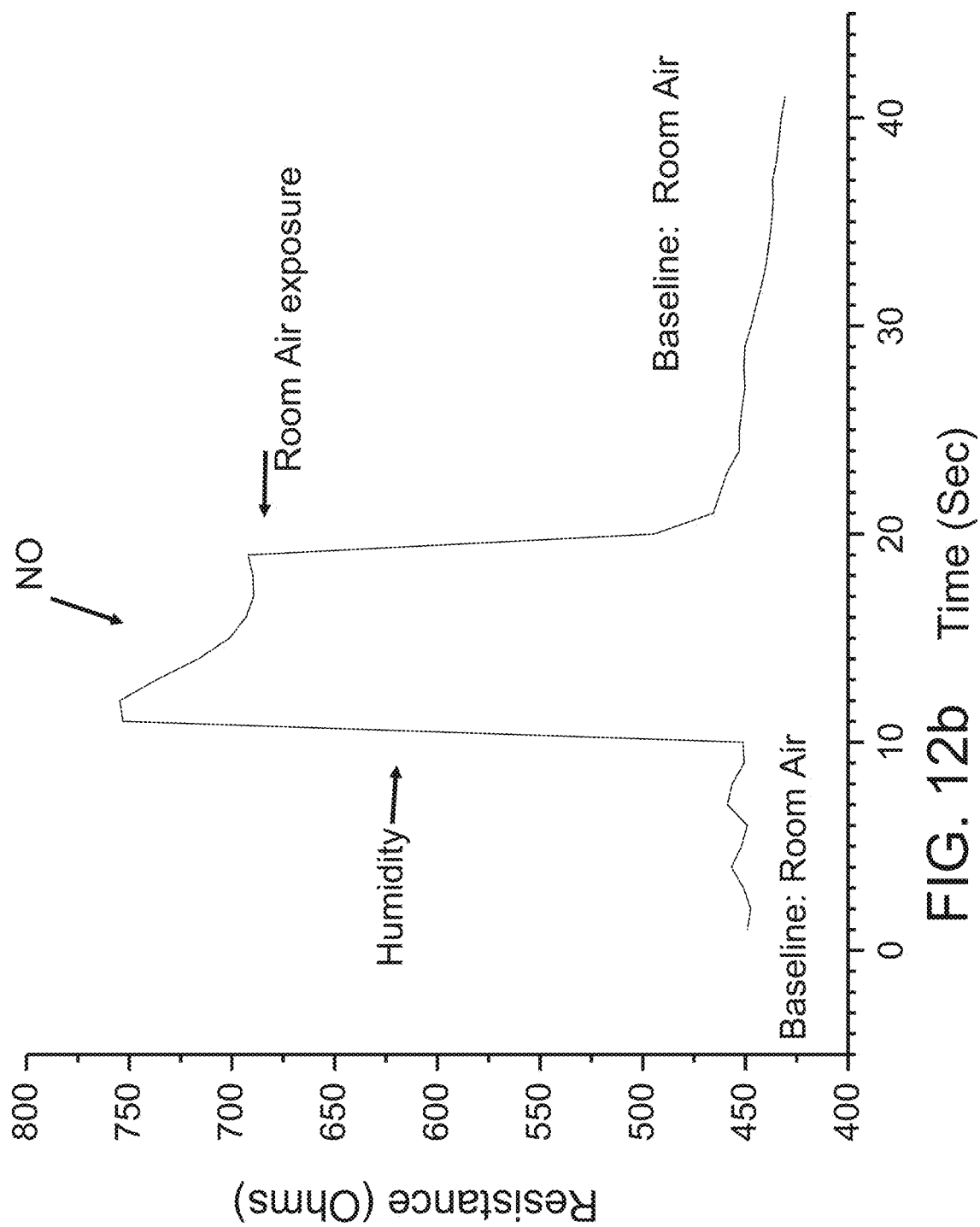

FIG. 12b is an example of the response of one embodiment of the test strip with chromatographic layer to a human breath. The sensor and chromatographic layer are configured to be sensitive and specific to nitric oxide. Humidity is the primary known interferent in human breath based on the specific sensing chemistry and test strip configuration. The sensor is baselined in room air. The breath stream is introduced and humidity is the first gas to pass through the chromatographic layer causing a sharp initial increase in resistance. The chromatographic layer is designed to exclude the other known gases in exhaled breath. Nitric oxide is the second gas to hit the sensor causing a decrease in resistance. The sensor is then re-exposed to room air. Examples of signal characteristics that are of interest include but are not limited to the initial slope of gas exposure, slope during gas exposure, initial slope of the return signal, slope at the end of gas exposure, changes in slope at various times, absolute changes in sensor properties (physical, electronic optical etc.), overshoot or undershoot from baseline before and after gas exposure, overshoot or undershoot from a calibration curve and regression lines at points in time when gases pass through the chromatographic layer.

Figure 12C:
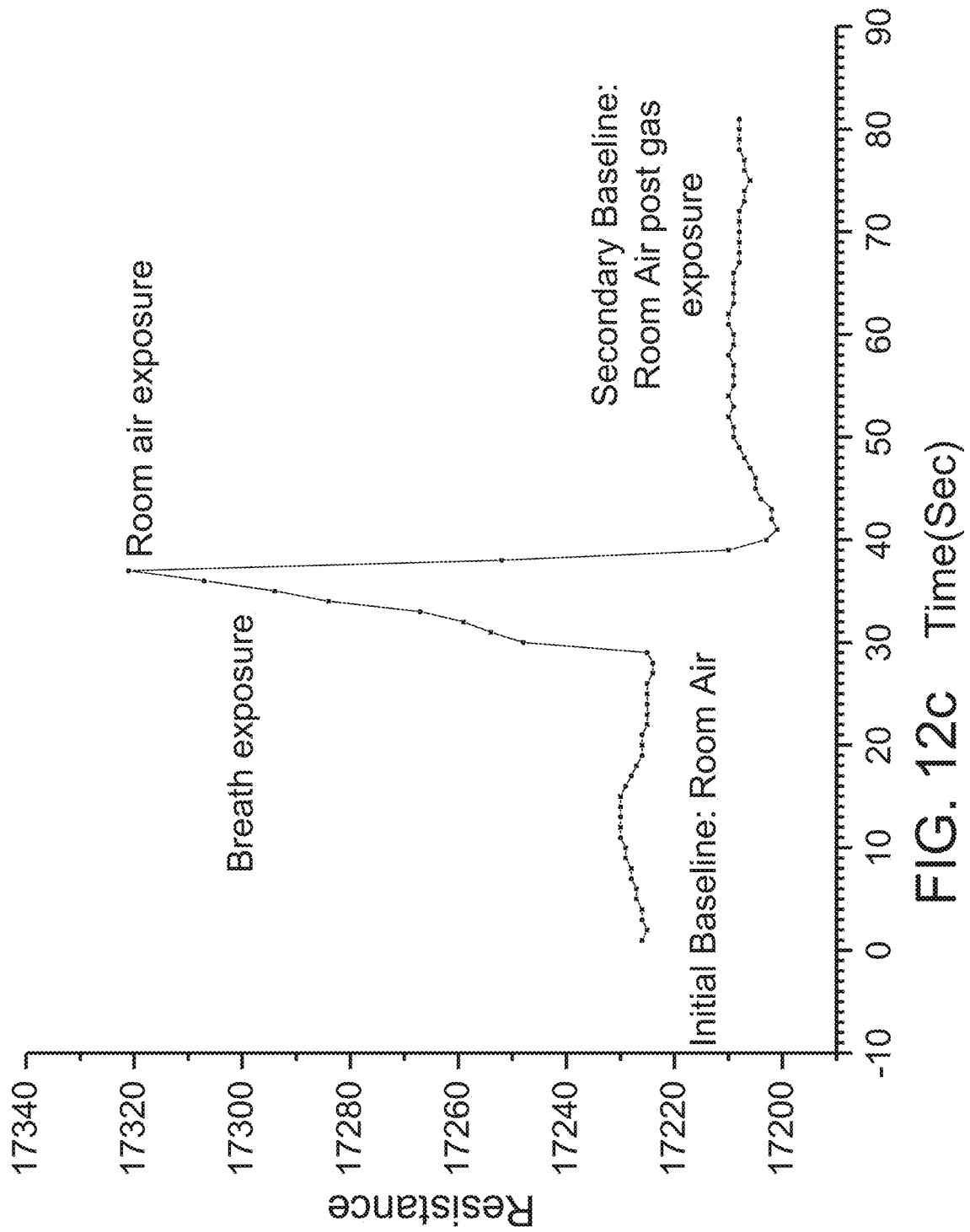

FIG. 12c is an example of the response of one embodiment of the test strip with chromatographic layer to a human breath. The sensor is configured to be sensitive to nitric oxide. The chromatographic layer is designed to exclude all interfering substances except humidity which adsorbs and desorbs predictably from the sensor. The sensor is baselined in room air. The breath stream is introduced and both humidity and nitric oxide pass through the chromatographic layer causing a sharp initial increase in resistance due to the humidity component. The sensor is then re-exposed to room air and the secondary baseline is compared to the initial baseline to determine the quantity of gas that has interacted with the sensor. Other examples of signal characteristics that are of interest include but are not limited to the initial slope of gas exposure, slope during gas exposure, initial slope of the return signal, slope at the end of gas exposure, changes in slope at various times, absolute changes in sensor properties (physical, electronic optical etc.), overshoot or undershoot from baseline before and after gas exposure, overshoot or undershoot from a calibration curve and regression lines at points in time when gases pass through the chromatographic layer.

Figure 14:
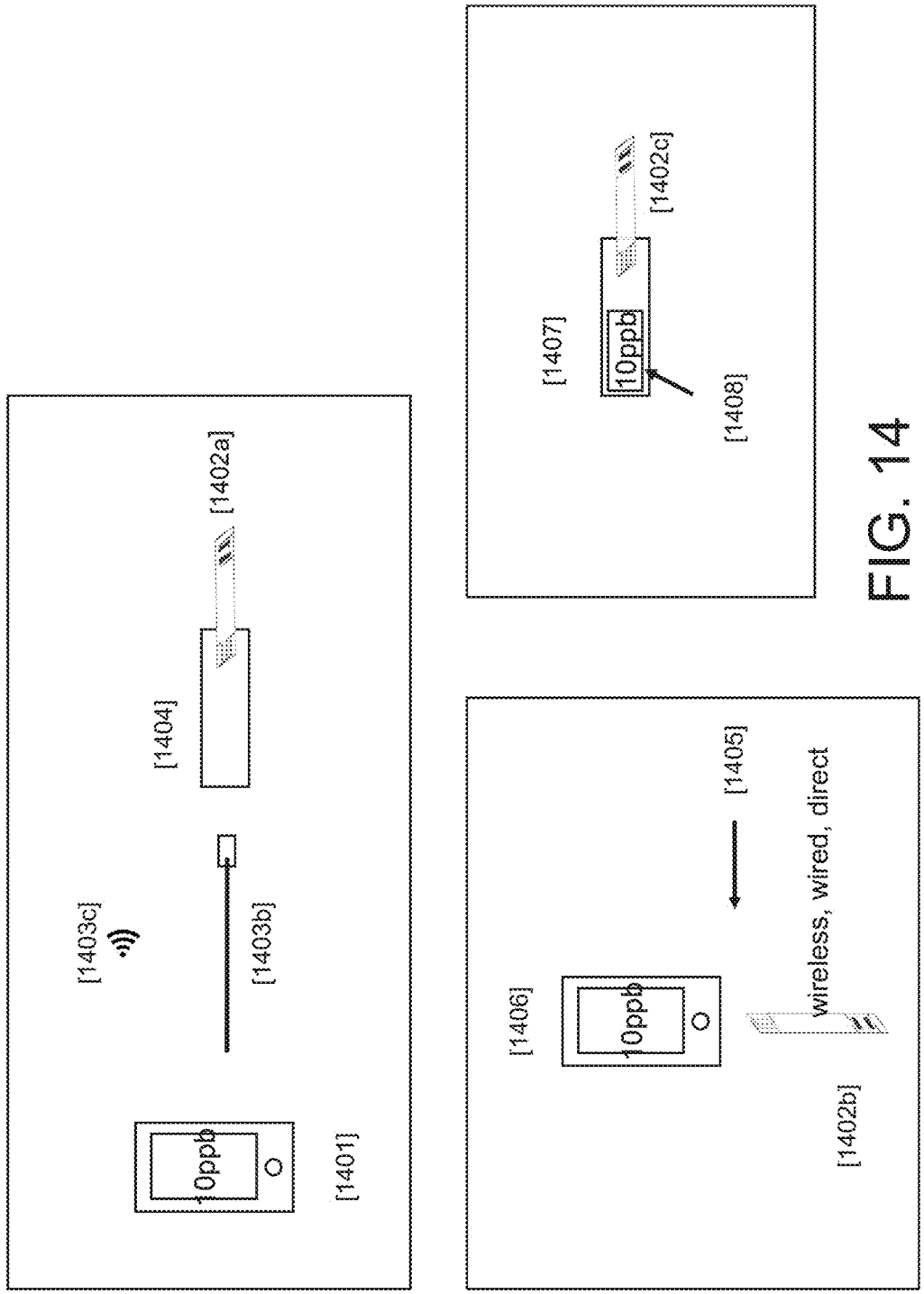
FIG. 14 and FIG. 14a demonstrate examples of variations of the electronic systems to provide a read out from the test strip.

Further embodiments of the system are described below.
Electronic Test Strip Reader FIG. 14 and FIG. 14a demonstrate examples of variations of the Electronic Test Strip Reader, hereafter referred to as "Reader". Generally speaking, the Reader is designed to provide a signal output from the test strip. The Reader may include means for providing power, collecting data, signal processing and interpretation, controlling the number of uses, running diagnostics, running a measurement, communicating with another device (e.g. phone or computer or tablet), etc. In one embodiment, the test strip and Reader are configured to measure the resistance change across two or more electrodes as the gas of interest interacts with the sensing chemistry. In another embodiment, the test strip and Reader are configured to measure the current or voltage across two or more electrodes of the test strip as the analyte gas or gases interact with the sensing chemistry. The electrodes may be configured as a simple chemically sensitive resistor (chemresistor), as a field effect transistor, or as Wheatstone bridge or other bridge circuits known in the art, or as a working and counter electrode, or as a working and counter and reference electrode. Examples of detection methods (e.g. the electronic and test strip configurations) are chemresistive, field effect transistors, amperometric, potentiometric or voltammetric signals. The test strip and corresponding electronics may be configured in a bridge circuit.

In one embodiment, a test strip [1402a] is plugged into to a Reader [1404]. The Reader [1404] is in communication with a mobile phone or other computing device [1401] via a wired connection [1403b] or by wireless means [1403b]. Examples of wireless communication include, but are not limited to Bluetooth, WiFi, RFID, Near Field Communication, etc. The Reader [1404] may be configured as an adaptor to connect the test strip to a mobile device via the audio output jack, micro-usb or mobile phone manufacturer's proprietary technology (e.g. Apple).

In another embodiment of the invention [1405], the test strip [1402b] communicates directly with a computing device [1406]. Communication may be established by directly docking the test strip into the mobile device or by integrating wireless technologies described above directly into the test strip.

Another embodiment of the electronic systems includes an integrated Reader [1407] that accepts a test strip [1402c]. The integrated Reader [1407] processes the measurement from the test strip [1402c] and interprets and displays the result of the test [1408].

Figure 14A:
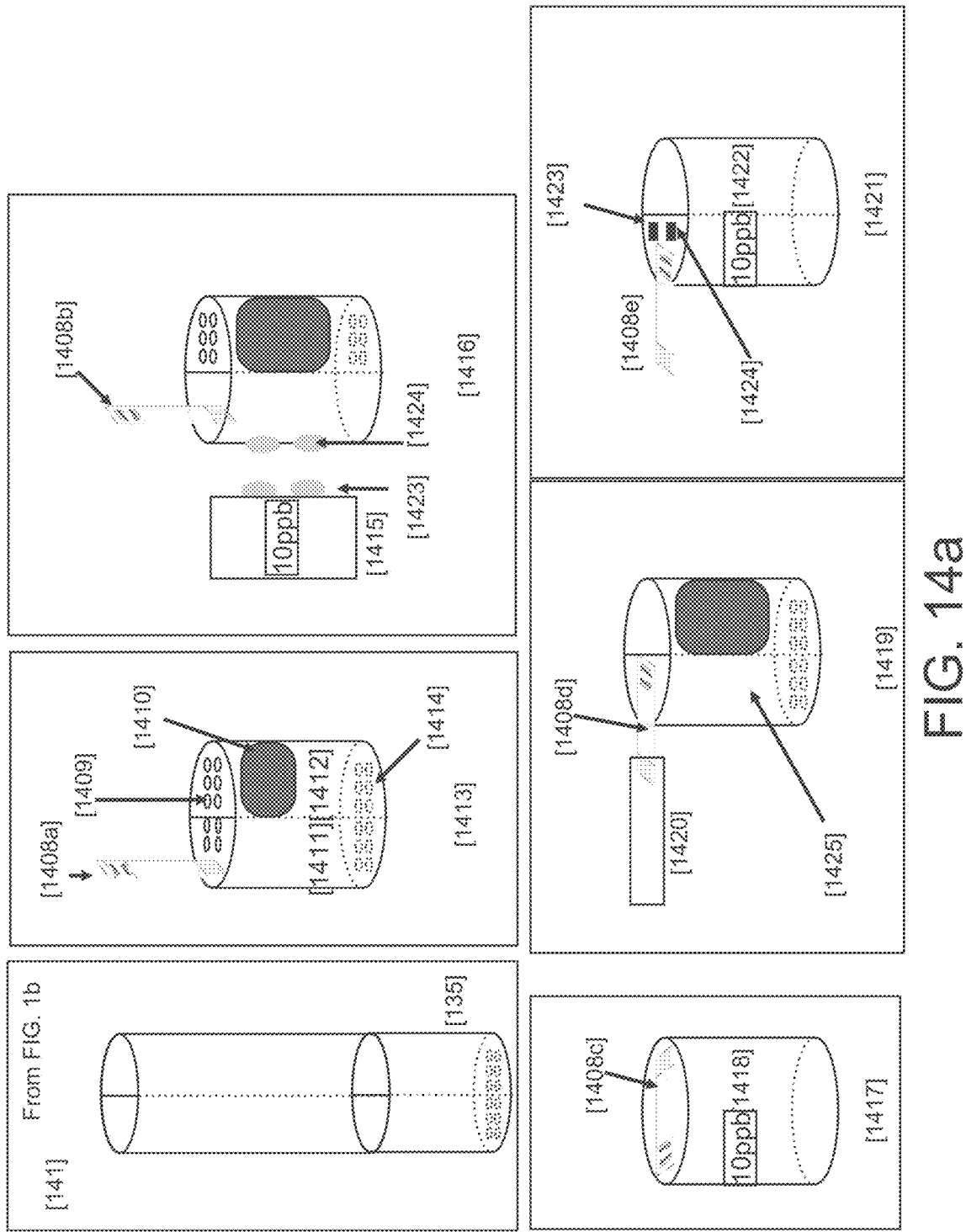

FIG. 14a demonstrates various configurations of the bottom portion [135] of a device [141] described earlier in FIG. 1a. In one embodiment [1413], the test strip [1408a] is vertically aligned in the gas stream and connected into the bottom portion [135] of the device [141]. The bottom portion of the device [135] may consist of at least one chamber or may have multiple chambers [1411] and [1412] to allow the flow of gas through vents [1414] and The gas may be filtered or conditioned during the inhalation phase [1410].

In another embodiment, the Reader [1415] does not accept the test strip directly. The Reader [1415] is configured to supply power and measurement capabilities via electrical contacts [1423]. The test strip [1408b] may be in electrical contact with electrodes [1424] and connected to the measurement device by joining the two electrodes [1423] and [1424]. Image [1424] may also represent holes in the device [1416] allowing the electrodes [1423] to connect to the test strip [1408b].

Image [1419] illustrates one configuration of the test strip [1408d], reader [1420] and bottom portion of the gas control device [1425].

The reader may also be integrated into the bottom portion of the device as shown in [1417] and [1421]. In the configuration shown in [1417] the unit may have no chambers. The reader [1421] may also house additional components such as a temperature sensor, a UV source or a heating element (not shown). The reader may also connect to the device wirelessly, for example via induction whereby data and power may be transferred.

Gas Preparation, Conditioning and Flow Control

Various embodiments and configurations are possible without deviating from the spirit of the invention. Configurations are dictated by the characteristics of the test strip, sensing chemistry, analyte of interest and environment in which the unit will be placed. Generally speaking, the gas preparation, conditioning, and flow control device may come in a variety of shapes, sizes, and contain any combination of chambers, structures, valves, filters or vents designed to deliver the analyte to the test strip. The device hereafter is referred to as the Gas Control Device.

Figure 15:
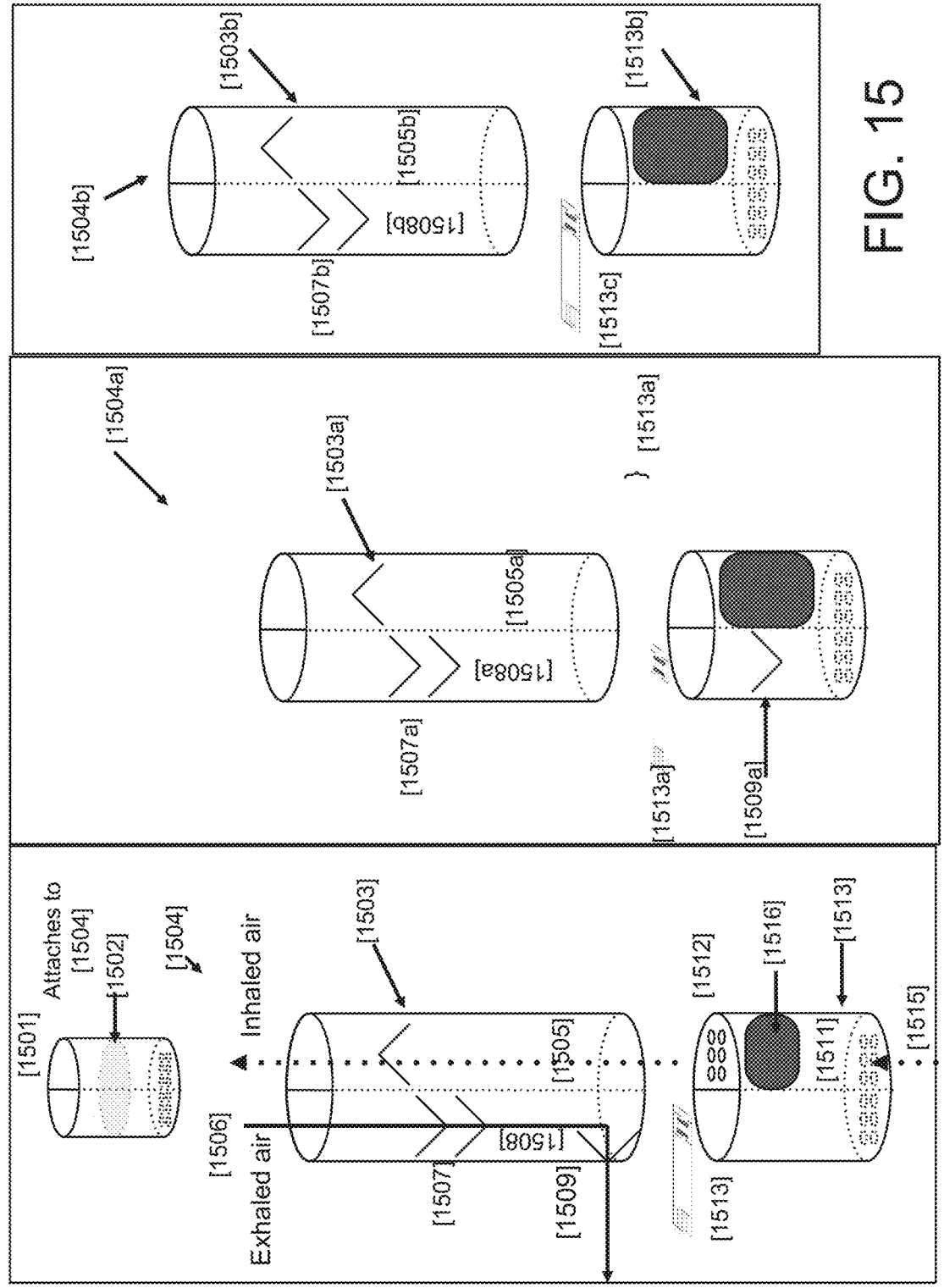
Figure 15A:
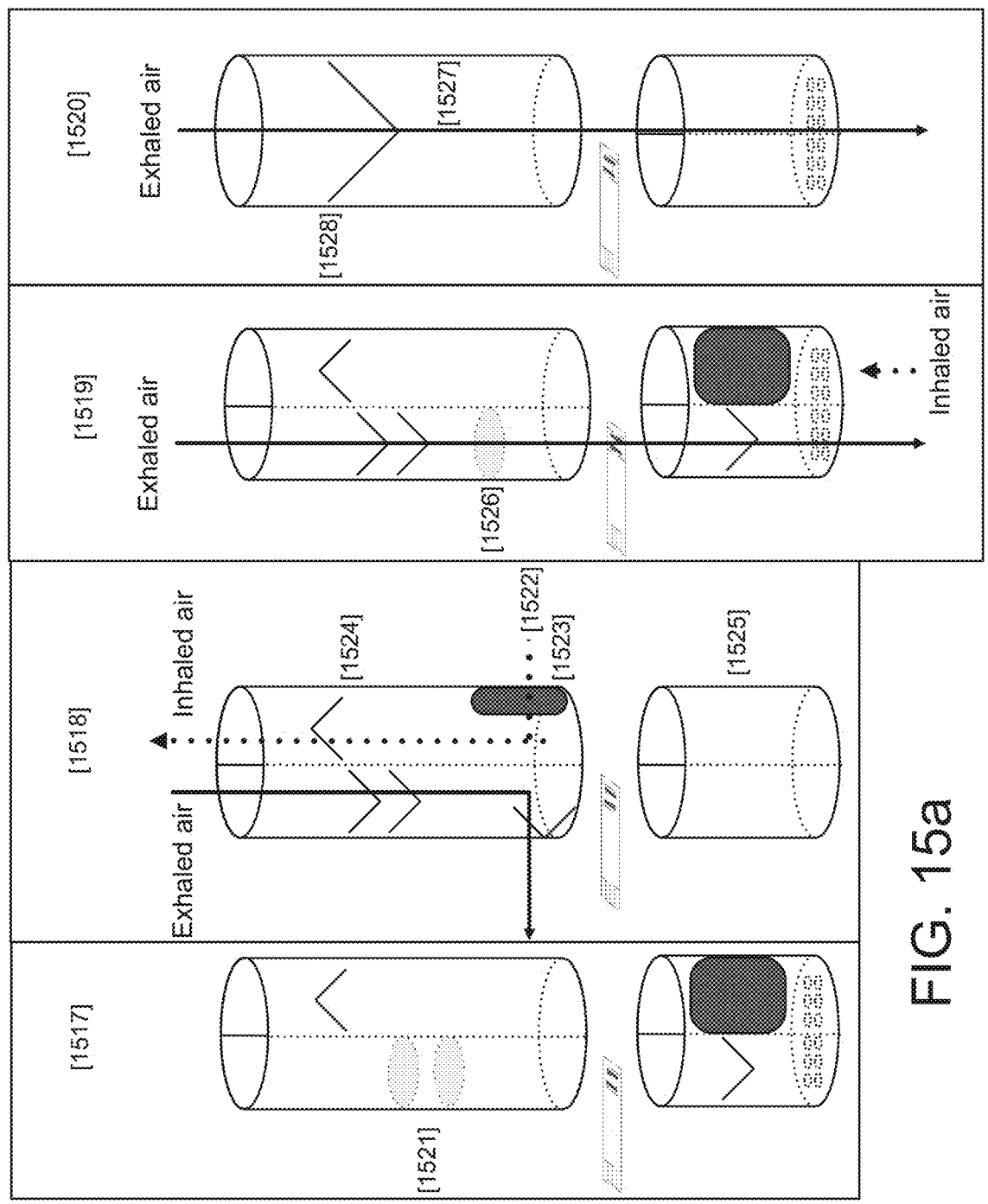

FIG. 15 and FIG. 15a demonstrate embodiments of various mechanisms to control the flow of gas to the test strip and methods of filtering the gas stream. An optional mouthpiece [1501] may contain a bacterial filter [1502] to enable device sharing among several patients, or to provide a sterilized environment to the device downstream. The optional mouthpiece [1501] is positioned proximally to the Gas Control Device [1504]. In one embodiment, the Gas Control Device [1504] is configured to measure exhaled nitric oxide in human breath. The Gas Control device [1504] may consist of a series of mechanisms, such as chambers, valves and/or filters. Filters may include items such as gas diffusion barriers, activated micro and nanostructures and selectively permeable membranes. Alternatively, a filter may be a high surface area material, such as a copper microbead-polytetrafluorethylene composite or reactive metal mesh. Other embodiments may include filters or membranes that have been further impregnated, coated or treated to serve dual purposes including chemical and physical separation of analytes (e.g. nafion coated PTFE). The patent positions their mouth proximal to the mouthpiece and inhales through the mouthpiece [1501]. Air is drawn in through a vent [1515] into a chamber [1511] and containing one or more filters [1516] designed to remove ambient gases from the air. The chamber [1511] is in fluid connection with [1505] so that the air can be drawn through a one-way valve [1503] and into the patients' lungs. The patient immediately exhales. The exhaled breath stream [1506] passes into the area [1508] and the flow rate is mechanically controlled by a mechanism, such as a valve, or series of valves [1507], which only allows gas to pass at a pre-specified flow rate above a pre-specified pressure. In a preferred embodiment, the flow rate is between 10 ml/sec and 100 ml/sec, the pressure is between 5-20 cm $H_2O$. The gas interacts with the sensor [1513] and out a one-way valve [1509]. The one-way valve [1509] may be designed to close as the patients exhalation pressure drops near the end of the exhalation. This would cause the last several seconds of the breath stream to be trapped in the chamber [1508] and be measured by the test strip [1513] and Reader (not shown). Trapping the air allows for diffusion of the gas through at least one layer on the sensor, including, but not limited to a chromatographic layer, and/or to allow for time for a chemical reaction to occur.

Another embodiment [1504a] is a similar design to the gas control unit [1504]. The main difference is that the one way valve [1509a] is positioned in the bottom portion of the gas conditioning unit [1513a]. This allows for direct flow of the gas over the test strip and passes out through the bottom of the device. When this valve closes, exhaled breath is trapped in the chamber [1508a].

Yet another embodiment does not involve trapping the gas and is shown in example [1504b]. The embodiment is essentially the same as [1504] and [1504a] but it does not contain a valve [1509] or [1509a] for trapping air in the chamber [1508] and [1508a].

In one embodiment the flow rate is measured by measuring pressure across an orifice. In another embodiment, flow rate is calculated by measuring pressure before an orifice.

Figure 24:
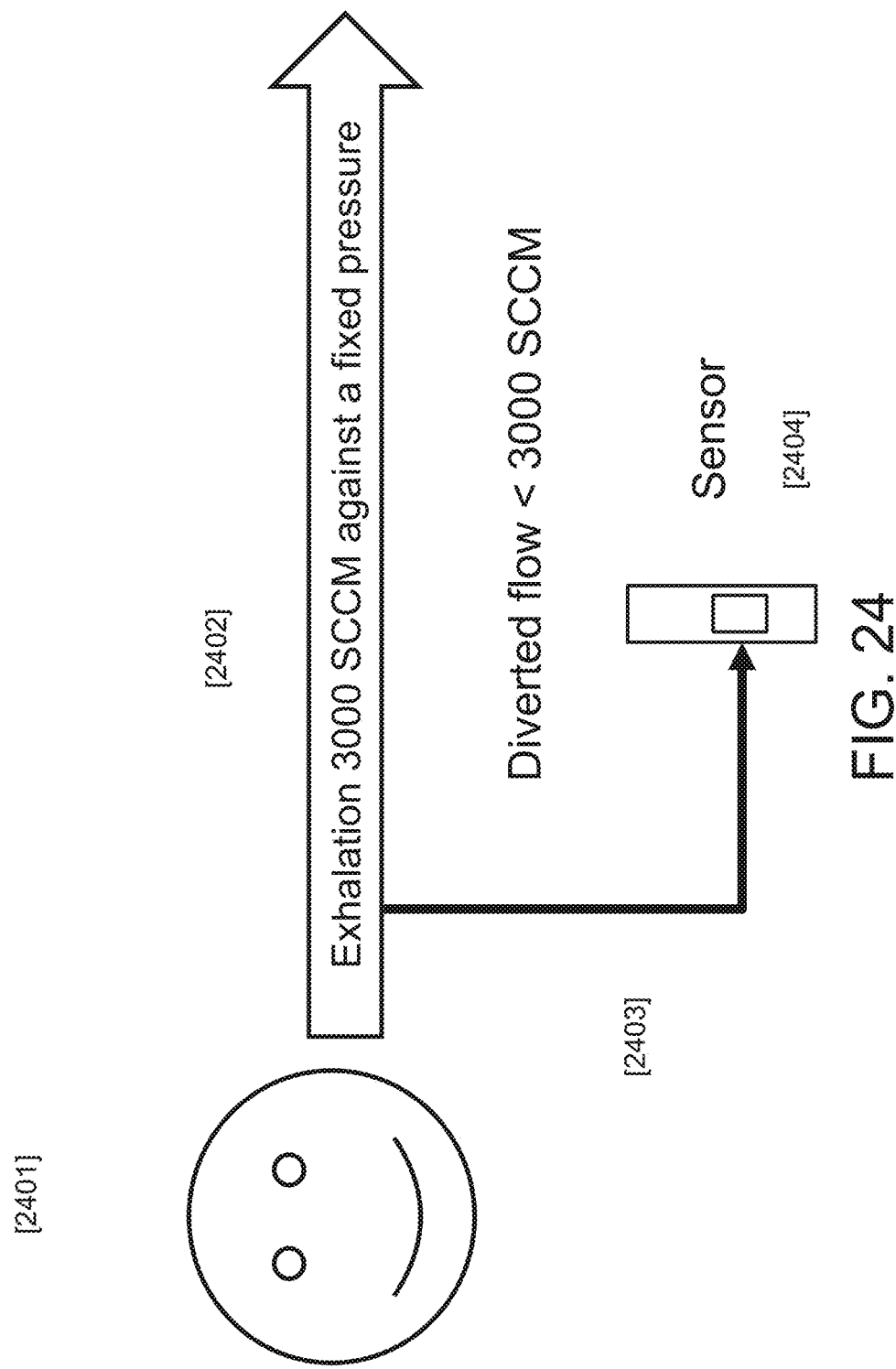
FIG. 24 demonstrates an example of diverting a portion of the exhaled breath to the sensor.
Figure 25:
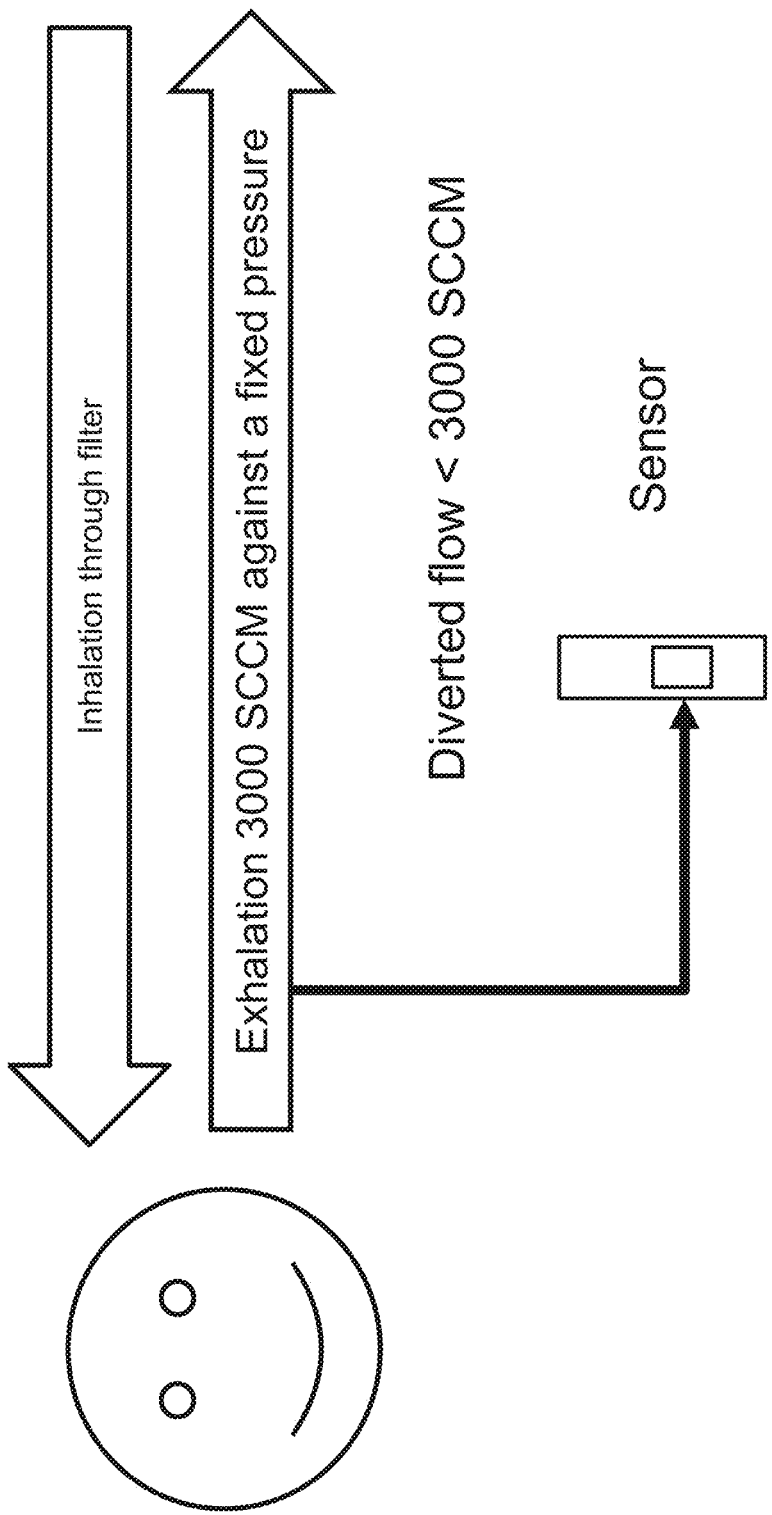
FIG. 25 demonstrates an example of diverting a portion of the exhaled breath to the sensor after inhaling through a filter.

In another embodiment, the exhaled breath stream is diverted as shown in FIG. 24 and FIG. 25.

Other embodiments of the gas conditioning device are show in FIG. 15a, [1518], [1519] and [1520]. Examples [1517], [1518] and [1519] function similarly to [1504]. The primary difference in example [1517] is that the valve configuration [1507] is replaced with at least one filter [1521]. The filter(s) may control the gas flow in addition to conditioning the gas sample. Examples of conditioning relate to removing water vapor, and functioning as a diffusion barrier or semipermeable membrane to remove interfering gases.

In another embodiment, the gas control unit is chemically treated (e.g. with Nafion to remove humidity from the gas stream) to provide conditioning effects.

Example [1518] differs from [1504] in that the positioning of the filter and vent [1523] is integrated into the top portion [1524] of the gas conditioning device.

Example [1519] differs from [1504] in that at least one filter [1526] is placed proximally to the test strip in the exhaled gas stream.

Example [1520] shows an embodiment of the gas control unit with a single chamber [1527], and a mechanism to control the flow rate.

FIG. 15b demonstrates two additional embodiments [1529] and [1531].

Example [1529] shows an embodiment of the gas control unit with a single chamber [1530] without a mechanism to control the flow rate.

Example [1531] shows an embodiment of the gas control unit with two chambers [1532] and [1533]. One chamber [1533] allows for inhalation through the device. The other chamber [1532] allows for exhalation through the device. In one embodiment, the test strip is placed in the fluid path of the exhaled air.

Figure 16:
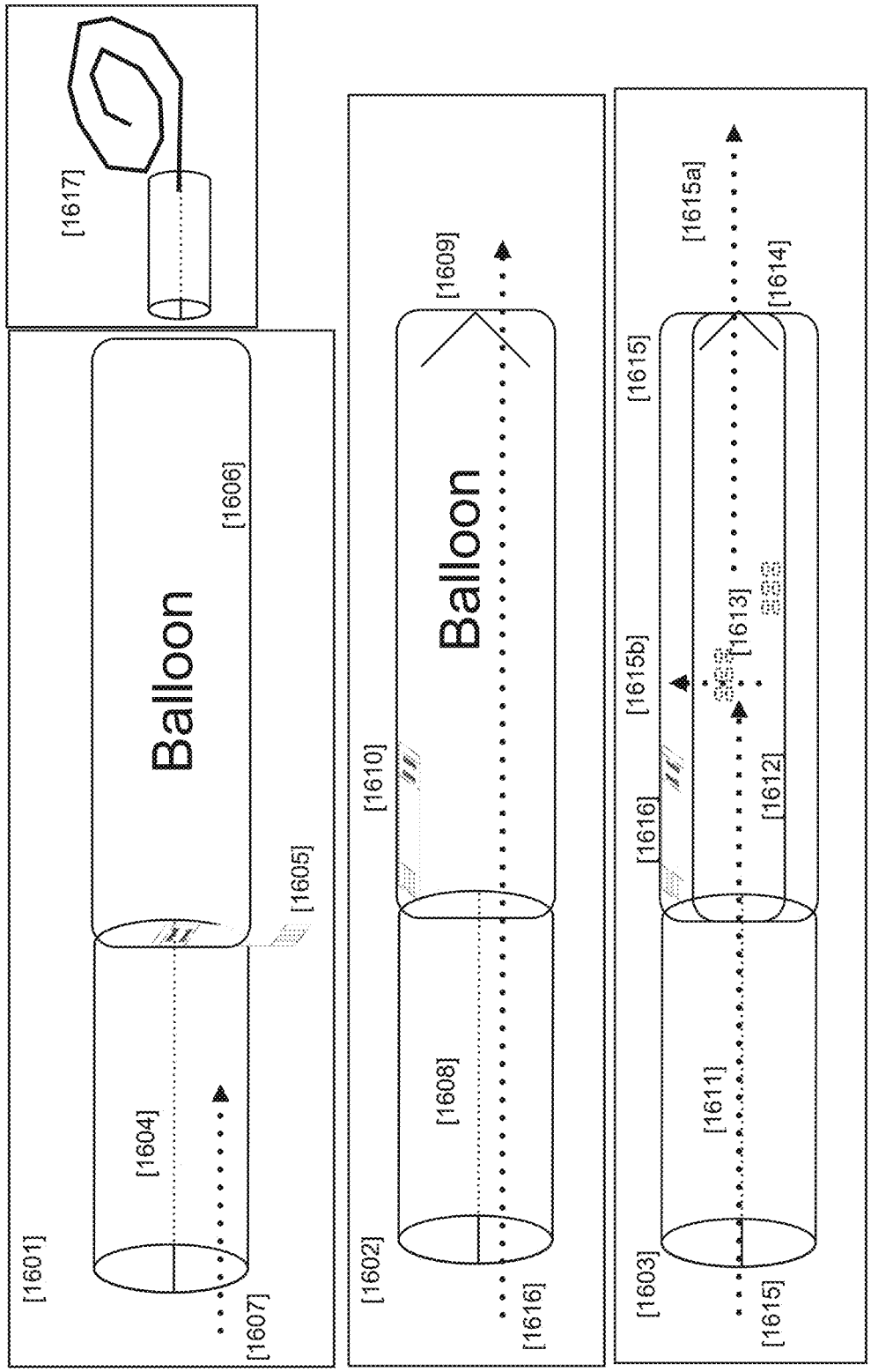
FIG. 16 demonstrates an example of the test strip incorporated into a vessel.

FIG. 16 demonstrates an example of the test incorporated into a balloon or vessel. In one embodiment [1601] a gas conditioning device [1604] as described earlier is attached to a balloon [1606]. The balloon is made of materials that will not interact with the gas of interest and will minimize gas diffusion through the sidewall. These materials may include, but are not limited to, plastics, such as polyester, polypropylene, polyethylene terephthalate, polyimide, etc., or metal foils, such as copper, aluminum etc., or graphitic materials, such as graphene, or graphene oxide thin films. In a preferred embodiment, the balloon is made of Teldar or Mylar. The balloon may be configured as a rolled tube [1617], or as an empty bag [1606] and may have either an open or closed end as shown in, [1601, 1606], [1602, 1609], [1603, 1614].

Embodiments may include a test strip [1605] inserted into the gas conditioning device [1604] and connected to a measuring device (not shown). Another embodiment of the device [1602] includes a gas conditioning unit [1608] connected to a balloon. The test strip [1616] or sensing chemistry can be deposited directly on the balloon or pre-assembled and attached to the balloon. The distal end of the balloon has a mechanism [1609] that allows for the flow of exhaled breath [1616] to pass through the device. When the pressure changes from the last portion of the breath maneuver, the mechanism closes trapping the gas in the balloon with the test strip for reading. Another embodiment [1603] contains a vessel, tube, or balloon [1612] inside another vessel, tube, or balloon [1615]. The internal vessel [1612] is treated to selectively allow the gas of interest to pass through [1615b] and [1613] into the outer vessel [1615].

Figure 16A:
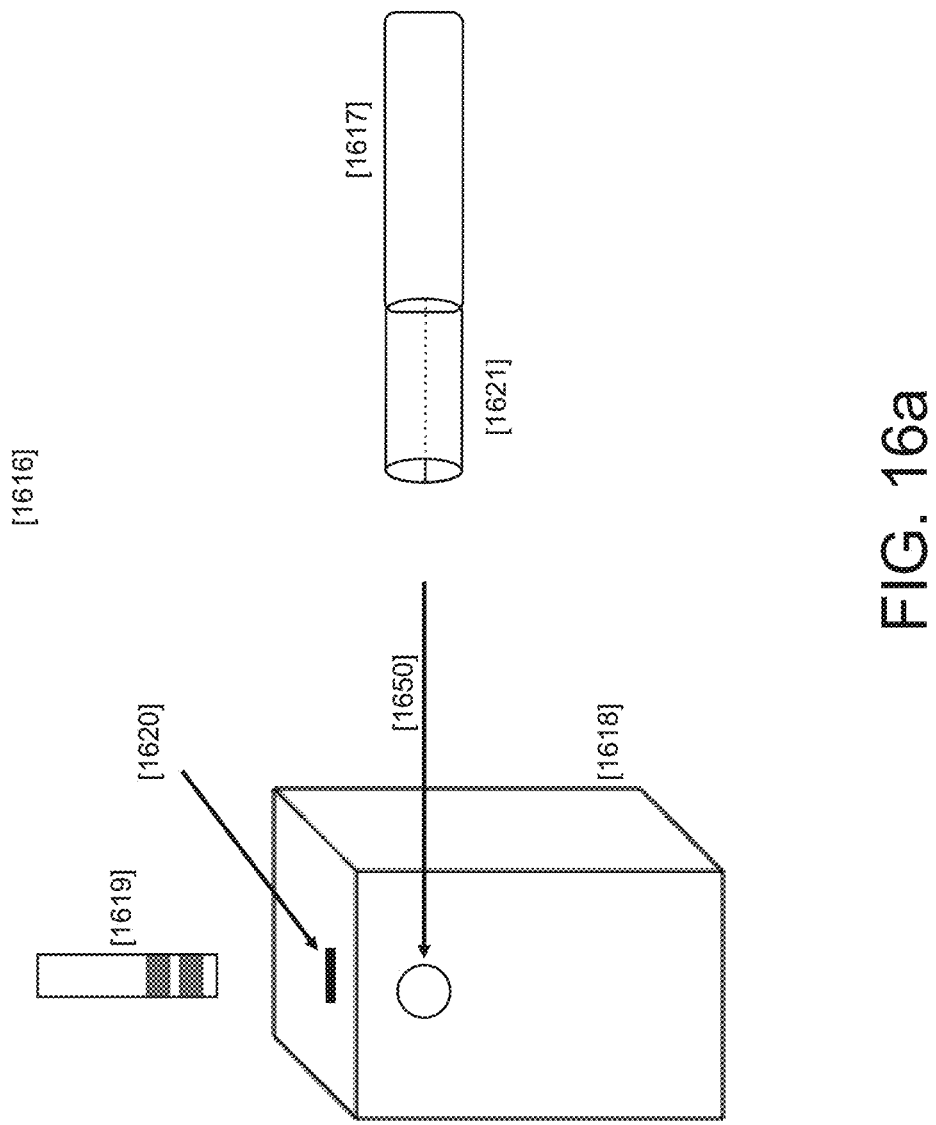
FIG. 16a demonstrates an example of a vessel connecting to a reader.

FIG. 16a is an example of one embodiment where the balloon [1617] is attached to a gas control device [1621]. The patient fills the balloon [1617] with expired breath. A test strip [1619] is inserted into the Reader [1618] via a slot [1620]. The balloon containing expired breath is connected to a Reader via an opening [1650] for measurement. The sample may be drawn into the Reader [1618] via a pump or by a spring/wire in the balloon [1617] designed to recoil the balloon to a rolled position as shown in FIG. 16.

Figure 17:
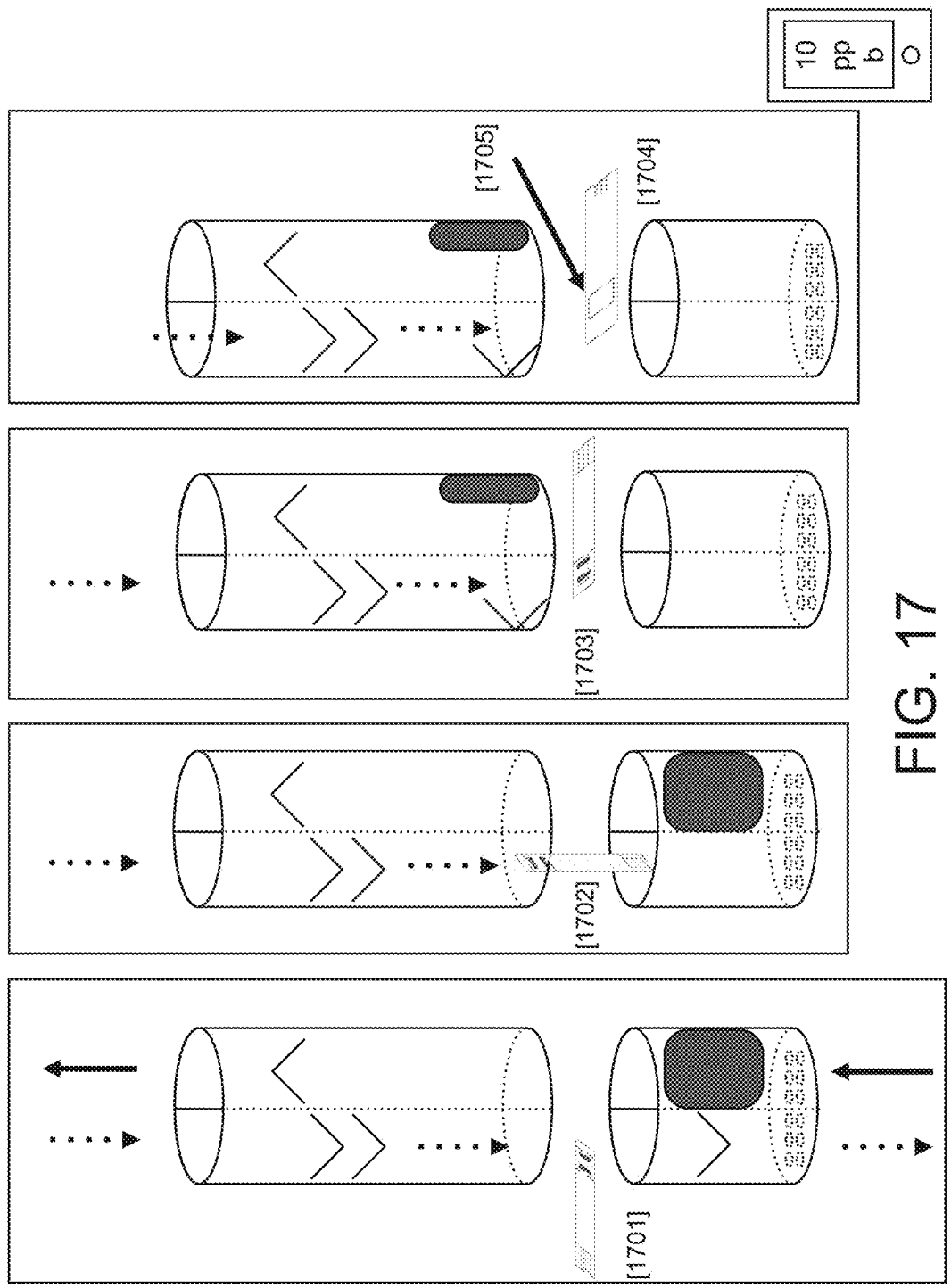
FIG. 17 demonstrates various orientations of the test strip within the device.

FIG. 17 demonstrates examples of various orientations of the test strip within the device. In the figure, the gas stream to be measured is represented by the dotted arrows. The test strip may be oriented horizontally [1701], [1703], [1704] or vertically [1702], or at some other angle. The sensing chemistry may be oriented towards the gas stream [1701] and [1703] or away from the gas stream [1704] (shown by 1705).

Figure 18:
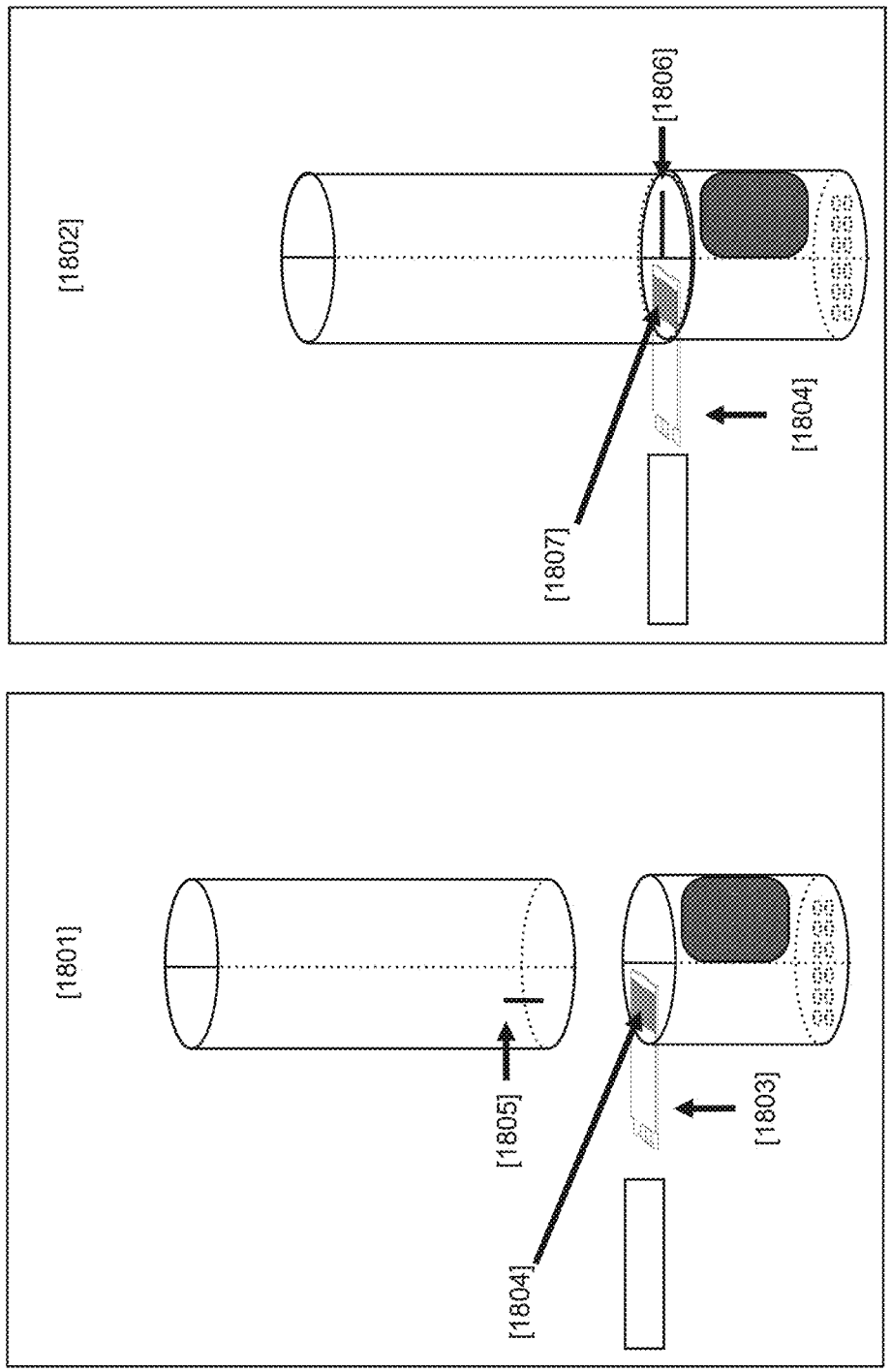
FIG. 18 is an example of the devices configured to peel or pierce a protective layer from the test strip.

FIG. 18 is an example of the devices configured to peel or pierce a protective layer from the test strip. In one embodiment [1801] the test strip [1803] has a protective cover [1804] that is pierced by a structure [1805] when the device is assembled for use. In another embodiment [1802], the protective cover [1807] on the test strip [1804] is peeled by a structure [1806] when inserted into the device. In another embodiment, the protective covered [1804] is removed by the user prior to insertion into the device.

Test Strip Sensing Chemistry

Many sensing chemistries are possible without deviating from the spirit of the invention. In one embodiment, the sensing chemistry is comprised of nanostructures functionalized to interact with an analyte causing a physical or electrical change across the nanostructures. In other embodiments the analyte causes a redox reaction at the nanostructural level which is measured. In another embodiment, the analyte causes a change in the surface electrons of the sensing chemistry, resulting in changes in the optical, electrical or physical characteristics, which are measured. Nanostructures may include, but are not limited to, carbon nanotubes (single walled, multi-walled, or few-walled), nanowires, graphene, graphene oxides etc. Examples of functionalization materials include:

Heterocyclic macrocycles
    a. Examples include but are not limited to: crown ethers, phthalocyanines, porphyrins, etc.

Metal oxides
    a. Examples include but are not limited to: AgO, PdO, $RuO_2$, $CeO_2$, $CrO_2$, $CO_2O_3$, $TiO_2$, etc.

Transition metals
    a. Examples include but are not limited to: Ag, Cu, Fe, Co, Cr, Ni Ru, Rh, Pt, Ti, etc.

Chemical Functional Groups
    a. Examples include but are not limited to: Ketone, ester, amine, carboxilic acids, alcohol, sulfonic acid, phosphate, benzyl, nitrile, aldehyde, nitrate, pyridyl, thiol, phosphoric acid, etc.

Functional Organic Dyes
    a. Examples include but are not limited to: Azo dyes, Cyanines, Fluorones, indogo dyes, photochromic dyes, Phthalocyanines, Xanthens, etc.

The functionalized nanostructure, hereafter referred to as sensing chemistry, is disposed over a substrate to form the basic components of a test strip. Electrodes are in communication with the sensing chemistry as described below.

In another embodiment, the sensing chemistry is a non-functionalized (i.e. un-sensitized) nanostructure. This embodiment may be used in conjunction with a functionalized nanostructure or it may stand-alone.

Secondary additives may be used to affect the drying characteristics and process ability of the sensing chemistry for deposition onto a substrate. Potential deposition methods include dip coating, air knife coating, knife over roll (tape casting), meyers rod coating, pad printing, ink rolling, drop casting, spin coating, electrospray, electrophoretic deposition, electropainting, screen, inkjet, flexography, gravure, offset, curtain coating, hot melt, rotary screen, doctor blade, slot-die, roll coating, press fitting, lamination, and spray coating. Additives may be used to change the viscosity, surface tension, wettability, adhesion, drying time, gelation, film uniformity, etc. These additives include, but are not limited to, secondary solvents, thickeners, and/or surfactants. These additives may serve one or multiple purposes. Examples may include, but are not limited to, those in FIG. 20 and:

Thickeners—polymeric and non-polymeric
    a. Glycerol
    b. Polypropylene glycol Surfactants—ionic and non-ionic
    a. Sodium dodecyl sulfate
    b. Triton X-100

Test Strip—Substrate, Electrode and Sensing Chemistry Configuration

Figure 19:
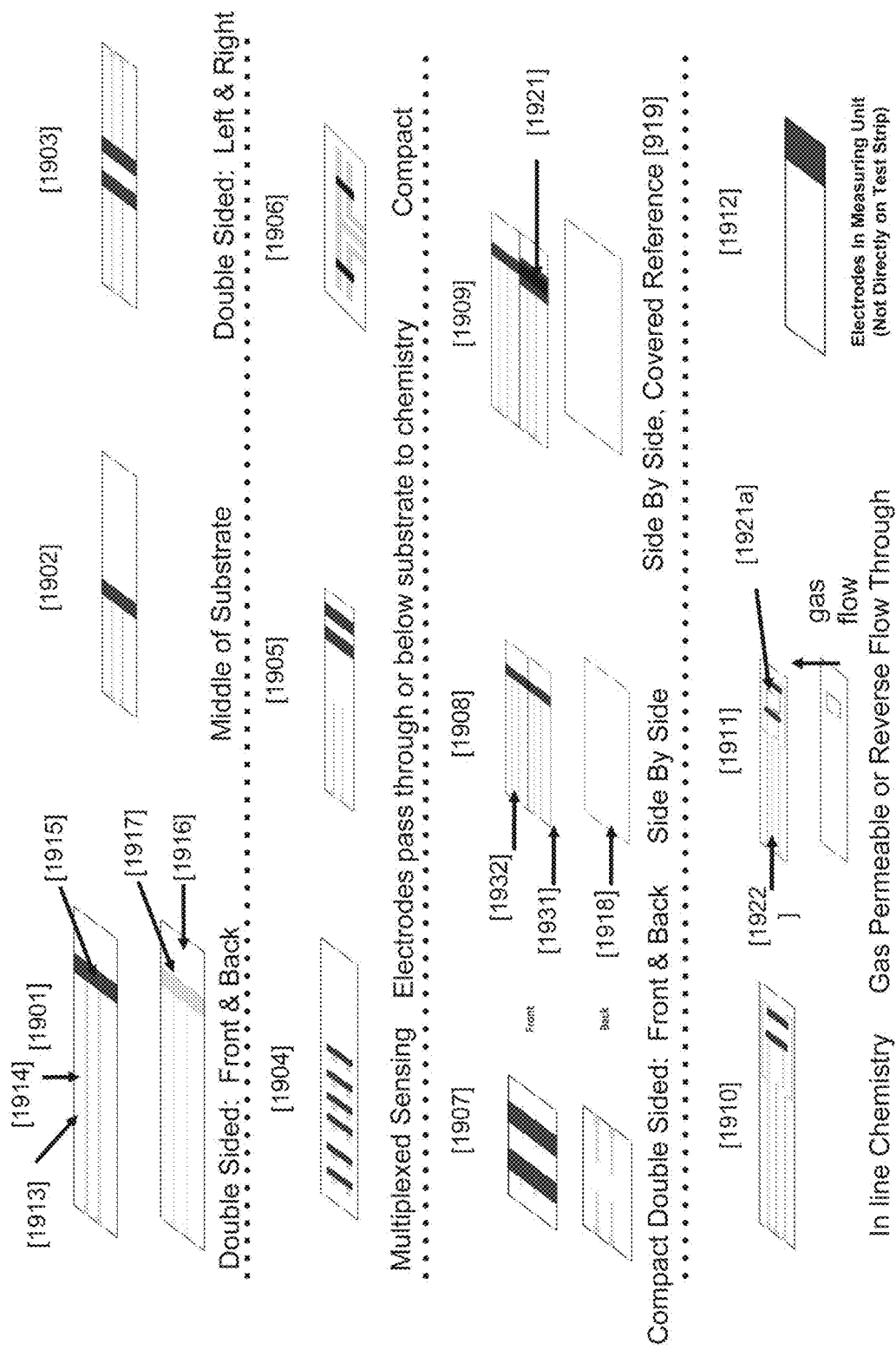
FIG. 19 shows various configurations of electrodes and chemistries on a test strip.

Various configurations or combinations of the substrate, electrode, and chemistry deposition are possible without deviating from the spirit of the invention. Configurations are dictated by the characteristics of the sensing chemistry, analyte of interest, and the environment in which the unit will be placed. Sensing chemistries may also be coated to prevent analyte interaction, so as to provide a reference, as in a chemresistive bridge circuit. Multiple sensing chemistries may be used, or the same chemistry may be deposited more than once, to serve as a reference, for multiplexed analysis, or for signal averaging. FIG. 19 shows examples [1901 through 1912] of various configurations of substrate, electrode, and sensing chemistries on one layer of the test strip.

In one embodiment [1901] a substrate [1913] contains electrodes [1914] and a sensing chemistry [1915] deposited across the electrodes [1914] on one side. The reverse side of the substrate [1916] also contains electrodes and a sensing chemistry. The reverse side of the substrate [1916] may be symmetric or asymmetric. Asymmetry may include different sensing chemistries, chemistry or electrode configurations, etc. The second sensing chemistry [1917] may the same or different from the first sensing chemistry [1915]. This may be used to adjust sensitivity and selectivity to the analyte of interest. In another embodiment [1908], two test strips are manufactured separately [1931] [1932] and then assembled onto a separate substrate [1918] to form a finished test strip. This may be done to increase the ease of manufacturability if the sensing chemistries [1931] and [1932] are different. In another embodiment in which the sensing chemistries are side by side [1909], one of the two sensing chemistries is covered [1921]. In another embodiment [1911] the substrate [1922] allows for the passing of gas [1921a] through it to the sensing chemistry. This allows for the test strip to be placed facing away from the gas stream as described earlier in FIG. 17 ([1705]).

Figure 19A:
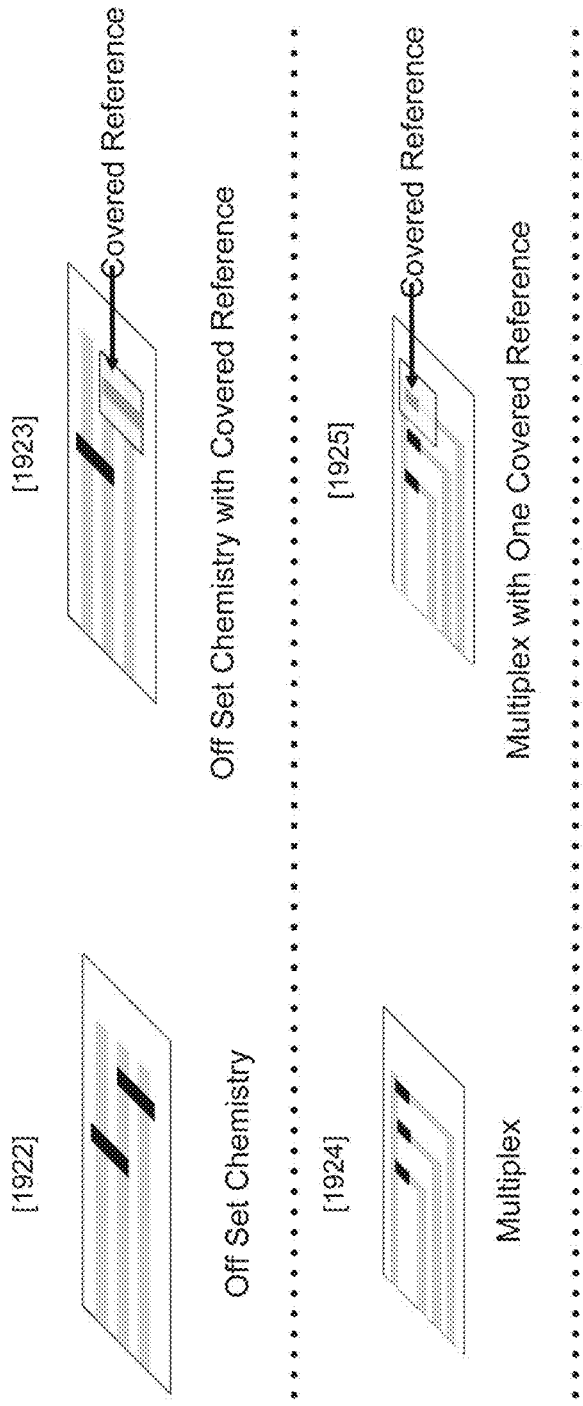
FIG. 19a shows examples of test strips with integrated heaters, sensors and electrical components.

FIG. 19 and FIG. 19a show examples [1901 through 1912 and 1922 through 1926] of various configurations of substrate, electrode, and sensing chemistries on one layer of the test strip. Examples of additional configurations [1922] and [1923] are shown with two chemistries offset on the test strip sharing one electrode. In one example [1923] one of the two chemistries is covered. In another embodiment [1924], multiple sensing chemistries are shown. In this example, the chemistries may share at least one electrode. In another embodiment [1925], at least one of the chemistries is covered. In another embodiment [1926], shows a chemistry bridging three electrodes. In this embodiment, the three electrodes may represent a working, reference and counter electrode.

Figure 19B:
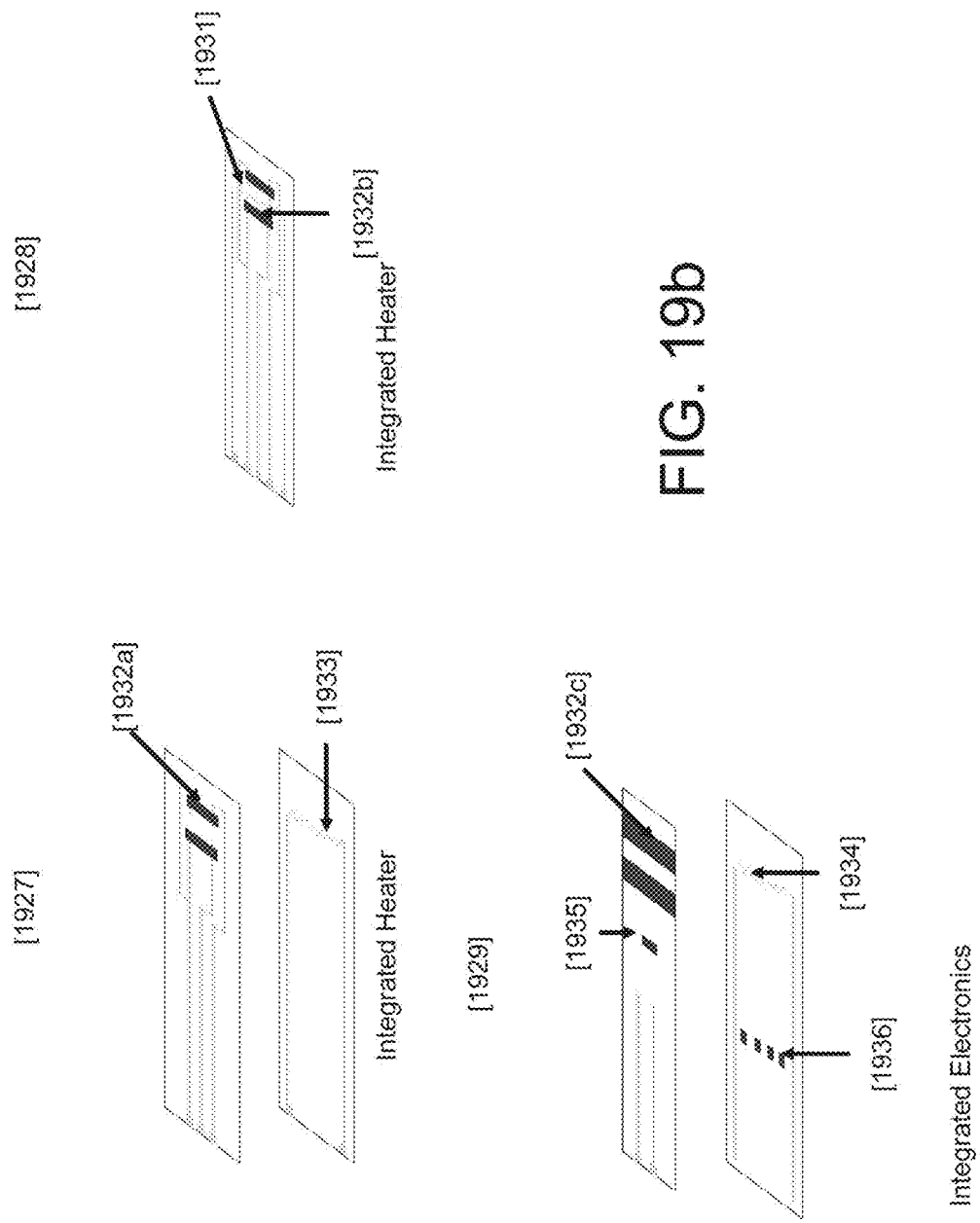
FIG. 19b shows embodiments of more complex configurations of electrodes and chemistries on a test strip.

FIG. 19b shows embodiments of more complex configurations. In certain embodiments, [1927], [1928], and [1929], an integrated heater [1931], [1933], [1934] is incorporated into the test strip either on the same layer as the sensing chemistry [1932a], [1932b], [1932c] (between the sensing chemistries, as shown in [1928]) or on a different layer (as shown in [1927] and [1929]). In other embodiments [1929] the test strip has additional sensor elements [1935] and integrated electronics [1936] on at least one layer. Examples of additional sensor elements [1935] may include, but are not limited to, temperature, and/or humidity sensors. Examples of integrated electronics [1936] may include, but are not limited to, resistors, fuses, capacitors, switches, etc. The test strip may also include a means for managing or controlling the number of uses (not shown). Examples include RFID, barcodes, circuit or fuse burn out, memory on the test strip, serial number, switch, etc.

In other embodiments, the heater, additional sensor elements, and integrated electronics described herein are incorporated into the reader.

In other embodiments, the heater, additional sensor elements, and integrated electronics described herein are incorporated into the reader and/or the chamber in which the test strip is placed.

Other examples (not shown) may include an electrode configuration suitable to measure an electrochemical reaction (i.e. working electrode, counter electrode, reference electrode).

In one embodiment, the test strip may be comprised of a substrate, at least one electrode, at least one sensing chemistry, and, optionally, at least one layer to protect the sensing chemistry from interfering substances. A circuit may be coupled to the sensing chemistry via an electrode pair. The circuit may be directly electrically coupled to the sensing chemistry, indirectly coupled by way of other components, or by other methods known in the art. The coupling can allow the circuit to provide power, send and/or receive a signal, and send and/or receive information about the sensing chemistry. The sensing area may consist of at least two nanonetworks in electrical communication with one or more electrical contacts. One network will act as the active sensing chemistry and will be sensitive to a particular set of analytes (e.g. nitric oxide). Additional networks will act either as a reference, as sensors for different analytes, or for the same analyte for signal averaging. The reference may be sensitive to a different set of analytes such that the differential signal between the active sensing chemistry, and the reference results in signal sensitivity towards a single analyte, a small set of analytes, or a subset of analytes with which the test strip is sensitive. In the case of multiplexed analysis, there may be more than one reference.

In another embodiment, the test strip may be comprised of a substrate, at least one electrode, at least one sensing chemistry, and optionally at least one layer to protect the sensing chemistry from interfering substances. The sensing area may consist of at least two nanonetworks deposited between two or more electrodes. One network will act as the active sensing chemistry and will be sensitive to a particular set of analytes (e.g. nitric oxide or carbon dioxide). The second network will act as a reference. The reference may consist of the same sensing chemistry as the active nanonetwork and may be covered or uncovered. The test strip and chemistries may be configured as a resistive circuit or bridge circuit.

Test Strip—Layers

Figure 21:
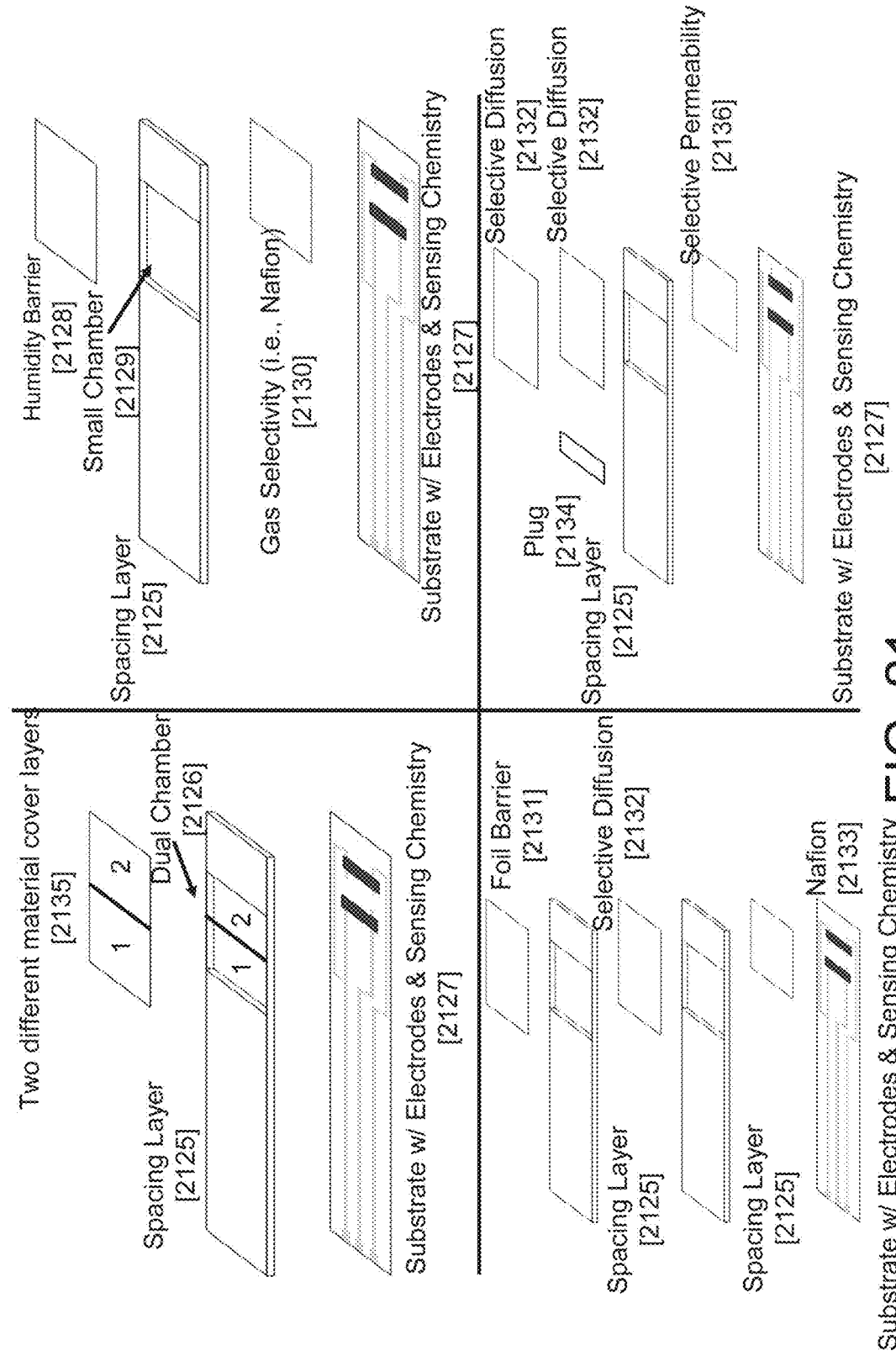
FIG. 21 shows examples of a test strip with multiple layers.

FIG. 21 shows examples of a test strip with multiple layers. Layers may be incorporated into the test strip for a variety of reasons depending on the sensing chemistry, electrode configuration, interfering substances and manufacturing process. Examples include but are not limited to: masking for chemistry deposition, support for chemistry deposition, protection from interfering substances, enhancing the selectivity and/or sensitivity of the test strip, acting as the sensing chemistry, spacing, formation of gas chamber(s), test strip rigidity or other structural configuration. Layers may be comprised of porous and non-porous polymers, composite materials, fibrous materials such as paper or fiber glass, woven and non-woven textiles, membranes, polymers, adhesives, films, gels, etc. The layers may be modified, for example, by chemically treating or coating and/or mechanically altering. The layers may serve one, or more than one, purpose. For example, a layer may serve as a structural component (e.g. improve rigidity or as a spacer), and a selective gas permeable membrane. Layers may be used in conjunction with each other to provide selective permeation of the gas of interest while protecting the test strip from interfering substances. In some embodiments there is a dielectric layer disposed above and in direct contact with the electrodes.

As shown in the dual chamber example [2121], spacing layers [2125] may also be used to create a single chamber or multiple chambers [2126]. The spacing layer [2125] is disposed above the substrate with the electrode and sensing chemistry [2127]. The chambers may be uniformly covered or differentially covered [2135]. In one embodiment, the differentially coated chambers allow for different gases to diffuse into the different chambers in order to be sensed by the sensing chemistry. In another embodiment [2122] a gas selective layer [2130] is disposed above the substrate with the electrode and sensing chemistry [2127]. The spacing layer [2125] containing a small single chamber [2129] is disposed above the gas selective layer [2130]. A humidity barrier is disposed above the spacing layer and covering the small chamber [2128]. In another embodiment [2123] two spacing layers [2125] are used. The two spacing layers may be used to create a larger chamber for the gas to accumulate at the sensor surface or to separate multiple diffusion layers. The spacing layers may also serve as structural support for the test strip and its layers. A Nafion layer [2133] is disposed above the substrate with the electrode and sensing chemistry [2127]. A spacing layer [2125] is disposed above the Nafion layer [2133]. A selective diffusion layer [2132] is disposed above the first spacing layer [2125]. A second spacing layer [2125] is disposed above the selective diffusions layer [2132]. A foil barrier [2131] is disposed above the second spacing layer [2125]. In another embodiment [2124] a different combination of layers is used. A selectively permeable layer [2136] is disposed above the substrate with the electrode and sensing chemistry [2127]. Two selective diffusion layers [2132] and a plug [2134] are disposed above the spacing layer [2125]. In one embodiment, the plug [2134] functions as a sealing mechanism when a test strip is inserted into a chamber.

Layers may be designed to be reactive to certain gases.

The layers may be applied by various coating methods including but not limited to dip coating, air knife coating, knife over roll (tape casting), meyers rod coating, pad printing, ink rolling, drop casting, spin coating, electrospray, electrophoretic deposition, electropainting, screen, inkjet, flexography, gravure, offset, curtain coating, hot melt, rotary screen, doctor blade, slot-die, roll coating, press fitting, lamination, and spray coating.

Examples of interferences may include but are not limited to: gases, condensed liquids, dissolved solids, particulate matter, humidity, temperature variations, etc. In the example of measuring nitric oxide in exhaled breath, examples of interferences may include:

Interfering Substances for Measuring Nitric Oxide in Exhaled Breath

| | |
|---|---|
| $CO_2$ | $H_2S$ |
| $C_2H_6O$ | $C_3H_6O$ |
| $NH_3$ | $C_2H_3N$ |
| $CO$ | $C_2H_4O$ |
| $C_5H_8$ | $NO_2$ |
| $H_2O_2$ | pH |
| $O_2$ | $H_2O$ |
| $H_2$ | |

FIG. 22 demonstrates examples of assembled test strips. [2201] depicts a fully assembled test strip. Embodiment [2202] depicts test strip with a foil barrier for puncture with a companion device. Embodiment [2203] depicts a test strip with a foil barrier that has a manual removal tab. Embodiment [2204] depicts a test strip with electrodes in the measuring unit rather than on the test strip itself. In this later embodiment, electrodes disposed in a companion device contacts the sensing chemistries on the test strip when the device and test strip are mated.

Figure 23A:
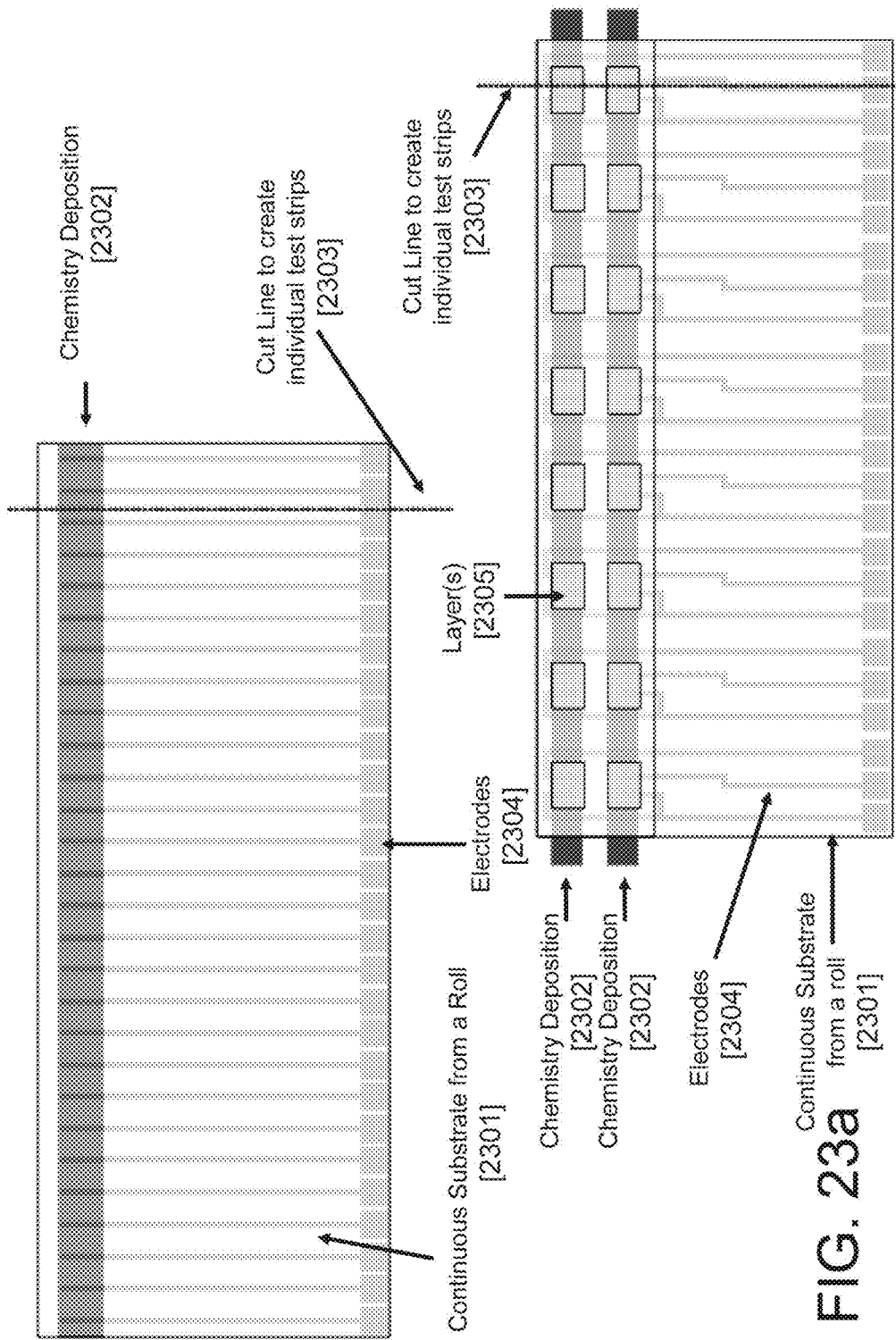
Figure 23C:
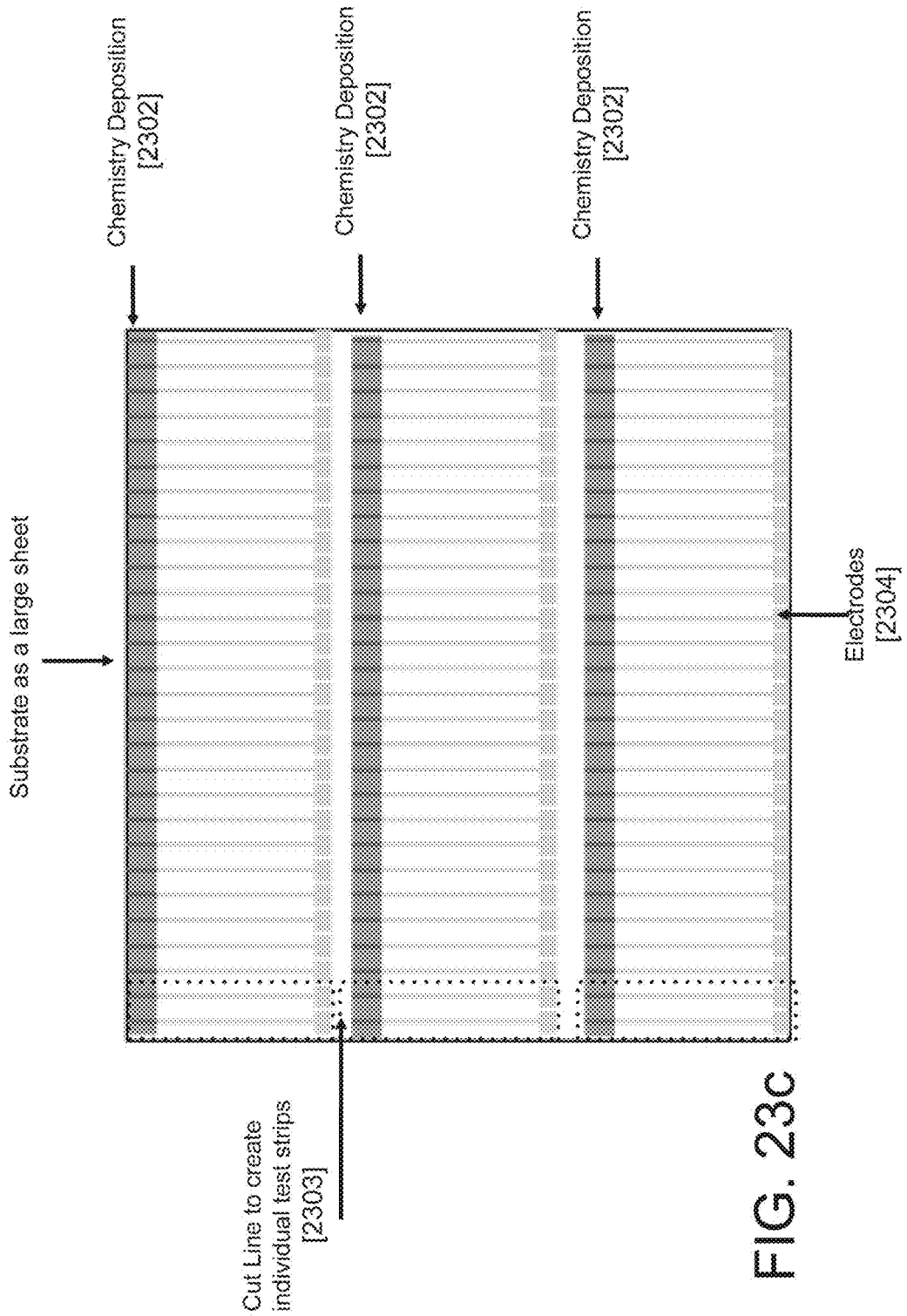

FIGS. 23a, 23b and 23c show various layouts of the test strips for mass production. A continuous substrate from a roll [2301] is supplied for chemistry deposition. The substrate may already include electrodes [2304]. The chemistry [2302] is deposited on the continuous substrate using any number of methods and coating techniques. This is not intended to be an exhaustive list. Individual test strips [2303] are cut using methods known in the art (e.g. die cut). Two chemistries can also be deposited [2302] on a continuous substrate from a roll [2301]. Layers [2305] can also be deposited on the continuous substrate from a roll [2301]. FIG. 23b depicts an expanded example of a section of the continuous roll. In this example, the section contains electrodes [2304], a chemistry [2302] disposed above the electrodes [2304] and two layers [2305] and [2306] disposed above the chemistry. FIG. 23c depicts deposition of electrodes [2304] and chemistry [2302] in three rows on a sheet. Any number of rows are possible without deviating from the spirit of the invention. A sheet containing electrodes is fed into a machine designed to deposit the chemistry. The sheets with the chemistry are then dried by any number of methods. Examples include but are not limited to air drying, convection, heat, infra-red, ultraviolet etc. One of skill in the art would appreciate that the additional layers contain pressure or heat sensitive materials those layers may also be applied. The sheets may be cut into smaller strips [2303] by any number of methods known in the art (e.g. die cut).

The examples incorporated herein primarily relate to gas detection however, the concepts, chemistries, and sensor designs described may also apply to detecting other biological or non-biological fluids, liquids or analytes etc. without deviating from the spirit of the invention.

Further examples of chemistry and sensor technologies of embodiments of the invention can be found herein. The non-limiting examples of additional chemistries include nitric oxide sensing chemistries, hydrogen and/or methane sensing chemistry, redox reactions, metal complex reactions, and acid base reactions. Non-limiting examples of additional sensing technologies include chemFET, optical and plasmonic sensors, and resistive sensors.

The following example relates primarily to NO Gas detection however, the concepts, chemistries, and sensor designs described may also apply to detecting other gases, fluids, analytes etc. without deviating from the spirit of the invention. This list is not intended to be exhaustive.

Industries (non-exhaustive list):
1. Industrial
2. Automotive
3. Environmental
4. Military
5. Agricultural
6. Veterinary
7. Medical
8. Air Quality Medical Specific Examples (non-exhaustive list)
Health diagnostics related to the following areas (non-exhaustive list):
1. Clinical chemistry & immunoassays
2. Breath analysis
3. Hematology & hemostasis
4. Urinanalysis
5. Molecular diagnostics
6. Tissue diagnostics
7. Point-of-care diagnostics
8. Exhaled Breath and/or Condensate
9. Virology
10. Analysis of Proteins and/or Antibodies
11. DNA/RNA
12. Oncology
13. Cardiology & metabolism
14. Infectious diseases
15. Inflammatory & autoimmune
16. Women's health
17. Critical care
18. Toxicology
19. Air Quality monitoring Examples of Techniques (non-exhaustive list)
1. Polymerase chain reaction (PCR & qPCR)
2. Nucleic Acid Amplification
3. ELISA
4. Fluorescence/Spectroscopic
5. Electrochemical
6. Redox
7. Chemically sensitive resistive elements
8. Chemically sensitive field effect transistors (ChemFET)

Examples of Specific Diseases (non-exhaustive list):
1. STDs
2. Breath tests (e.g. COPD, Asthma, Lung cancer, digestive disease)
3. Digestive Disorders
4. Urinary L TE4
5. MRSA
6. Influenza
7. Viral detection
8. Bacterial detection Nanostructures may include, but are not limited to, carbon nanotubes (single walled, multi-walled, few walled or the like), nanowires, nanoparticles, graphene, graphite oxides etc.

FIG. 24 is an example of diverting the gas stream from an exhaled breath to the sensor. In one embodiment, the patient [2401] exhales through a device referenced herein at a flow rate. A portion of the exhalation [2402] is diverted [2403] to a sensor [2404]. In one embodiment the flow rate is 3000 standard cubic centimeters per minute (SCCM)±10%. In another embodiment the flow rate is 3000 SCCM±5%. In one embodiment, the flow rate of the diverted gas stream is less than or equal to the exhalation flow rate. In another embodiment, the flow rate of the diverted gas stream is less than or equal to 3000 SCCM. In another embodiment, the flow rate of the diverted gas stream is less than or equal to 500 SCCM. In another embodiment the flow rate of the diverted gas stream is less than or equal to 350 SCCM. In another embodiment the flow rate of the diverted gas stream is between 1 SCCM and 3000 SCCM. In another embodiment, the diverted gas stream is passed through a Nafion tube.

FIG. 25 is similar to FIG. 24 and also includes an inhalation maneuver [2505] by the patient [2501] to remove certain ambient gases from the air. A portion of the exhalation [2502] is diverted [2503] to a sensor [2504]. In one embodiment, the ambient gas is NO. In another embodiment, the ambient gas is $NO_2$. In another embodiment, both NO and $NO_2$ are removed.

Figure 26A:
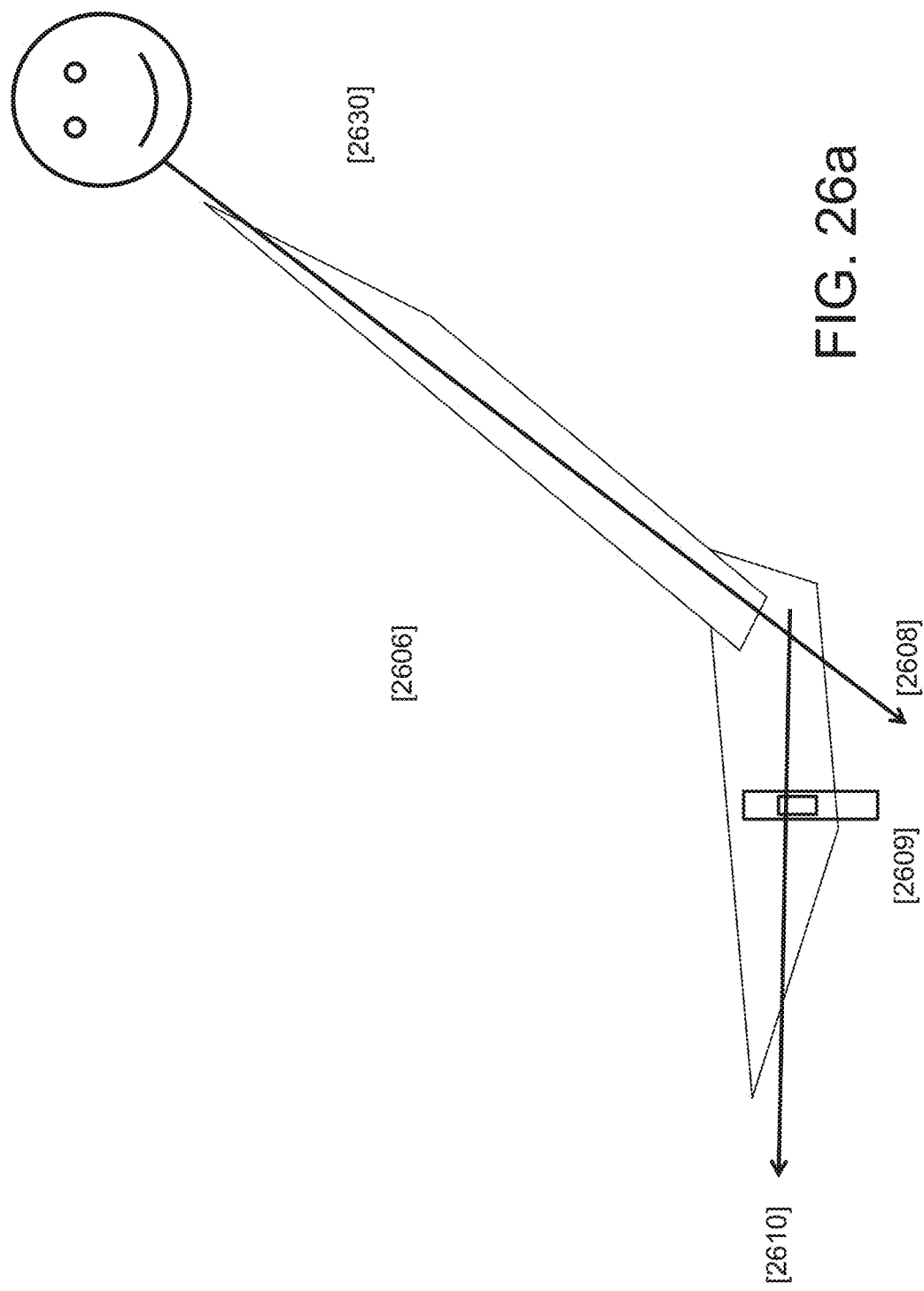

FIG. 26 demonstrates one embodiment of the device incorporating the concepts of FIG. 24 and FIG. 25 described below. In one embodiment, the device [2601] folds. In one embodiment, the unfolded device [2602] contains a reader [2603] and a gas conditioning portion [2604] that are connected. In one embodiment, the gas conditioning portion [2604] may accept a filter [2605]. The reader may accept the test strip in various locations. Two examples [2606] and [2607] are shown, but this is not intended to be exhaustive of all the configurations. FIG. 26a demonstrates one embodiment of the concepts described in FIG. 24, FIG. 25 and/or FIG. 26. A patient [2630] exhales through the device [2608] and the breath stream is diverted [2610] over the sensor [2609].

In one embodiment, the reader show in FIG. 26a, contains a display. In one embodiment, the display provides feedback related to the exhalation flow rate. In one embodiment, the display shows the result of the test.

The reader [2603] may also be integrated into the device [2602] as a whole shown in FIG. 26. In another embodiment, the signal may be from an optical measurement of the sensing chemistry.

Figure 26B:
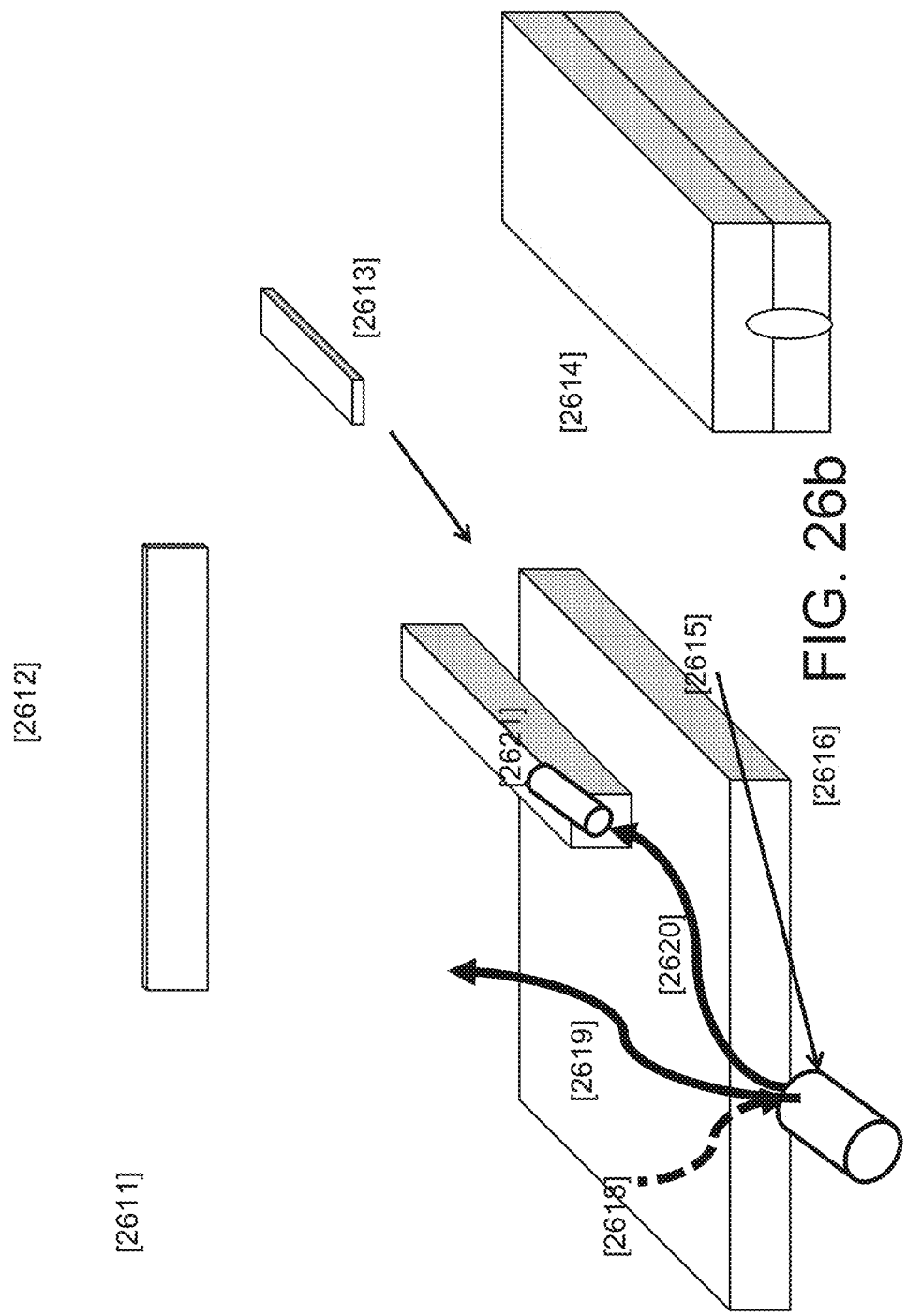
FIG. 26b demonstrates one embodiment of the invention wherein the reader and gas conditioning system are incorporated into a device.

FIG. 26b demonstrates one embodiment of the invention wherein the reader and gas conditioning system are incorporated into a device [2611]. The device is comprised of a display [2612] connected to a base [2615]. In this example the base [2615] is show without a cover. The test strip [2613] is inserted into a chamber [2621], which is located in the device The chamber may be designed to create laminar or turbulent flow. The chamber may have an entrance path for a fluid sample. The chamber may also contain an exit path for a fluid sample. In one embodiment, the device [2611] either contains or accepts a mouthpiece [2616] for a patient to inhale and/or exhale through the device. In one embodiment the mouthpiece [2616] contains a bacterial filter.

In one embodiment, the patient inhales through the mouthpiece [2616]. The inhaled air stream passes through a channel [2618] before the mouthpiece [2616]. The patient then exhales through the mouthpiece and down a second channel [2619]. In one embodiment the second channel [2619] allows for the exhaled breath to exit the device. In another embodiment, the exhaled flow rate is measured. In one embodiment, a portion of the exhaled stream may be diverted through a third channel [2620]. In one embodiment, the channel [2620] is in fluid connection with the chamber [2621]. In one embodiment, the channel [2620] is comprised of a nafion tube. In another embodiment, the channel [2620] contains a filter for removing unwanted analytes. In another embodiment, the channel [2620] is designed to perform multiple functions. In another embodiment, the channel [2620] is designed to dry the breath stream. In one embodiment, the channel [2618] contains a filter to remove unwanted analytes from the ambient air. In another embodiment, the chamber [2621] and/or fluid channels [2618], [2619], [2620] and/or mouthpiece [2616] may contain a valves, flow restrictors, or sensors. In another embodiment the device [2611] contains a vent.

In one embodiment, the display folds on top of the base [2614].

In another embodiment, the device [2611] contains additional sensors. Examples include but are not limited to temperature, humidity, flow, gases (e.g. carbon monoxide).

FIG. 26c demonstrates an embodiment of the invention wherein the output [2627] of the device [2622] is selected from a plurality of endpoints. In one embodiment, the measurement of the electrical properties of the sensor corresponds to at least one of a plurality of analyte concentration ranges. In one embodiment, the outputs are quantitative or semi quantitative. In another embodiment, the outputs are qualitative. In yet another embodiment, the endpoints may be determined from the age of the patient. The endpoint for an age less than 12 correlates to three ranges of analyte concentrations (i) less than 20 parts per billion, (ii) between 20 and 35 parts per billion, (iii) greater than 35 parts per billion of the analyte. The endpoint for an age greater than 12 correlates to three ranges of analyte concentrations (i) less than 25 parts per billion, (ii) between 25 and 50 parts per billion, (iii) greater than 50 parts per billion of the analyte. In another embodiment, the device [2622] may determine the type of output based on the input received from one or a plurality of sources. In some embodiments, the output is above or below a pre-determined analyte concentration. In some embodiments, the pre-set analyte concentration is selected from a range of concentrations between 1 and 300 parts per billion. When the analyte is nitric oxide the pre-set analyte concentration may preferably be 19 parts per billion, 20 parts per billion, 25 parts per billion, 30 parts per billion, 35 parts per billion, 40 parts per billion, 50 parts per billion. When the analyte is methane the preferable pre-set analyte concentration is 15 parts per million or 20 part per million. When the analyte is hydrogen the preferable pre-set analyte concentration is 15 parts per million or 20 part per million.

In one embodiment, the test strip [2625] may contain electrodes in a specific configuration or of a specific resistance indicating to the device the type of output to display In another embodiment, a bar code [2624] is used to determine the type of output to display. The bar code may be located in any number of places without deviating from the spirit of the invention. Examples include but are not limited to the test strip [2625] or packaging [2623]. In another embodiment, a chip [2626] is inserted into the device [2622] to provide information regarding the at least one of a plurality of outputs. In another embodiment, the type of output is manually entered into the device.

In another embodiment, the bar code or chip may also enable the device to utilize a specific calibration table. In another embodiment, the bar code or chip may contain information pertaining to a calibration table.

In another embodiment, information regarding the plurality of outputs or information regarding calibration is received from a paired mobile computing device.

Chemistry and Sensor Technologies

NO Sensing Chemistries

Several chemistries present themselves for NO sensing. In some of these systems the sensing mechanism will respond to changes in the oxidative state of a molecule, or redox chemistry. In others, physisorbed species can change the contact resistance or other electrical or physical properties between nanostructures. We have identified three potential ways to use changes in the system to measure concentrations of NO: a gas phase electrochemical cell (similar to a fuel cell), a gas phase redox reaction, and metal complex reactions. Each of these strategies is outlined in detail below.

Redox Reactions

Electrochemical cells, similar to a standard battery, are used to monitor redox reactions in the current NO sensors. While the electrodes can vary widely, the following discussion is exemplary of their mechanism of action. In general, electrochemical cells generate a voltage due to the spontaneous generation of electrons and ions when two different materials are in electrical contact with one another. Which material is oxidized depends on the relative redox potentials (typically written as a reduction reaction) of the materials. The species that is reduced has a more positive (or less negative) redox potential than the species that is oxidized. In a standard zinc-copper battery system, zinc metal (reduction potential of $-0.7618$ V) is oxidized releasing electrons and zinc ions (Equation 1). The electrons are donated to reduce copper ions (potential of $0.3419$ V) to copper metal (Equation 2), during which the voltage across the zinc and copper electrodes can be monitored.

$$Zn(s) \Leftrightarrow Zn^{2+} + 2e^- \quad (1)$$

$$Cu^{2+} + 2e^- \Leftrightarrow Cu(s) \quad (2)$$

Figure 27:
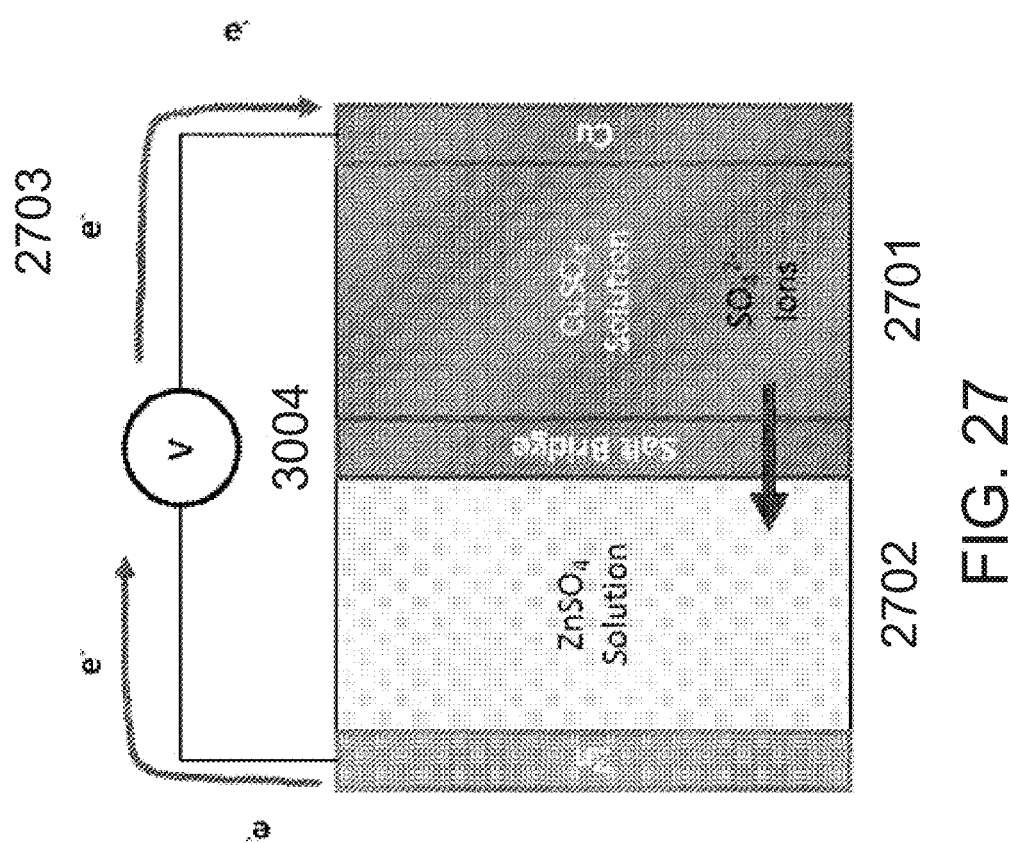
FIG. 27 demonstrates an embodiment of a standard copper-zinc battery.

As shown in FIG. 27 from an engineering standpoint, typically, the copper electrode (2701) is immersed in an electrolyte solution of copper (II) sulfate, and the zinc electrode (2702) is immersed in a solution of zinc sulfate. The electrolyte solutions are connected with a salt bridge or porous membrane to provide ion transport between the two electrochemical processes (2703), and the voltage is monitored across the copper and zinc electrodes (2704). Because the cell will have zero potential when at equilibrium, any disturbance, such as the oxidation of copper, will result in increased voltage and current as the cell works to reach equilibrium. Therefore, in this case, by monitoring the voltage or current across the copper and zinc electrodes, the oxidation of copper can be observed. A similar principle can be applied to gas phase reactions, such as in a hydrogen fuel cell. In the case of a hydrogen fuel cell, the zinc and copper electrodes are replaced with hydrogen gas ($H_2$) and oxygen gas ($O_2$), respectively. These are separated by a proton ($H^+$) permeable membrane, such as Nafion®, and an electric reducing potential is applied across the system. In this system, the hydrogen is oxidized, and releases an electron. The oxygen is reduced and takes up two protons ($H_2$) to form water. Given that nitric oxide can be either oxidized or reduced to form several gaseous products, such as $NO_2$ or $N_2O$, a similar system to a fuel cell can be constructed. The system may contain one or all of the following: a functionalized or coated carbon nanotube based electrode, a Nafion membrane for proton transport, and a proton source, such as a solid or liquid acid. The coating on the nanostructure can be chosen based on the redox potential of various metal oxides, summarized on Table 1.

TABLE 1

Redox potentials of Various Oxides

| Metal Oxide | Reduction Potential (V) |
|---|---|
| AgO | 0.7996 |
| PdO | 0.951 |
| RuO2 | 1.12 |

TABLE 1-continued

Redox potentials of Various Oxides

| Metal Oxide | Reduction Potential (V) |
|---|---|
| CeO2 | 1.34 |
| CrO2 | 1.48 |
| Co2O3 | 1.92 |

Beyond the traditional electrochemical cell, a simple redox reaction at the nanotube surface for NO detection is possible. In one example, a metal oxide can be chosen that will either reduce the NO to $N_2O$, or oxidize it to $NO_2$. If the process is a one or two oxygen event, such as in the case of AgO or $CeO_2$, a change in resistance or impedance may be measured to detect the event, or a A field effect transistor (FET) may be used to monitor the event. This type of redox cell differs from the above electrochemical cell, in that a proton exchange is not required. This type of sensor may have any number of electrodes (two, three etc.). Given that both of these processes are driven by electrochemical interactions at the surface of the material, both access to reactive species at the surface, and high surface area are critical to highly sensitive detection. To this end, the use of nanostructures over coated with a nanoscale metal deposit can provide >200 $m^2/g$ of surface area, as well as a conductive substrate for efficient and effective electrical monitoring.

Metal Complex Reactions

An alternative to the redox chemistry is the use of organic-metal complexes, which are well known to strongly bind gasses. Complexation of the gas in the organic complex gives rise to a change in the electrical conductivity of the system. Therefore, by monitoring the resistance of the system, the concentration of an analyte gas can be determined. By choosing an appropriate complex, the specificity of the sensor can be tailored to certain gas molecules. Binding the complex to a conductive surface, such as a nanostructure, allows the advantage of high surface area, with only a small amount of the complex. Furthermore, in order to improve selectivity, a gas permeable membrane may be used. One example is Nafion® to prevent anionic contaminants, such as $NO_2^-$. Another example is silicone or PTFE.

Acid/Base Reactions

Beyond the redox style sensors, acid-base reactions are possible for sensing. The operation of these sensors is fundamentally different, in that the NO is converted to $NO_2$, an acidic gas, and reacted with a basic polymer, such as polyethylene imine (PEI). In a ChemFET style sensor, the acid-base reaction at the surface of the CNT changes the electric field, resulting in a change in signal.

Examples of catalysis may include $CrO_3$, $CeO_3$, $CO_2O_3$ etc. Catalysts may be coated on nanostructures for greater surface area, and therefore improved conversion efficiency.

The thickness of the PEI layer can have a large impact on the sensitivity and measurement rate of the sensor. To maximize the sensitivity nanostructures may be coated with PEI prior to deposition onto the chemFET surface. This will provide the thinnest possible layer of PEI, and allow for rapid diffusion of the $NO_2$ to the surface without deactivation by PEI not adjacent to a CNT surface.

Examples of scrubbers for removing potential interfering gas may include Ascarite II, calcium oxide, lime etc.

Sensing Methods
ChemFET

Figure 28:
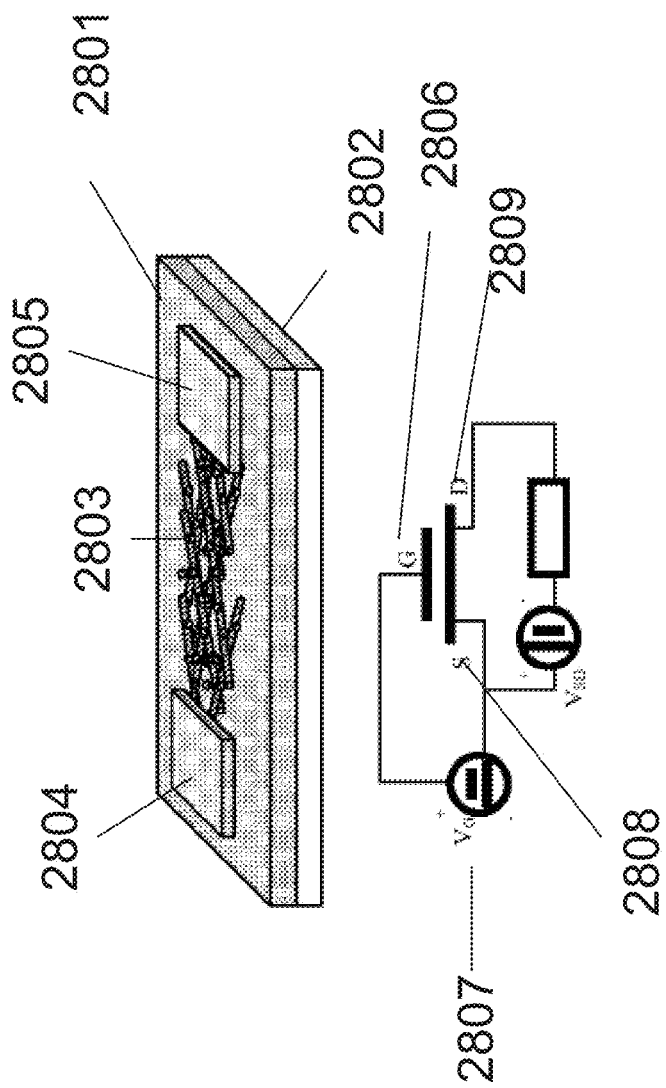
FIG. 28 demonstrates one embodiment of a ChemFET layout.

One potential sensing method is shown in FIG. 28 a chemically sensitive Field Effect Transistor (ChemFET) film (2801) on a flexible substrate (2802). In this style of sensor, the sensing element may be composed of a mesh of nanostructures (2803), which is placed between a source terminal (2804) and a drain terminal (2805). An underlying gate electrode (2806) is supplied with a bias (2807) that affects the field around the nanostructures. The adsorption of an analyte molecule will change the conductance between the source (2808) and the drain (2809), which is measured as a change in the resistance.

More specifically, nanostructures offer great adsorptive capacity due to their large surface area to volume ratios. One example is a carbon nanotube, consisting of only a single layer of carbon (abbreviated as SWNT), are ideal candidates for adsorption, offering superior sensitivity. Semiconducting SWNTs have P-type behavior, where the main charge carriers are holes. When the analyte is adsorbed it either draws or donates electrons from the SWNT, altering the conductance. By monitoring the change in conductance, one may discern which analytes are present in the atmosphere. The specificity of the signal can be tailored by careful choice of surface coatings on the SWNT. Other nanostructures using this configuration are possible without deviating from the spirit of the invention.

In the case of NO, $H_2$ or $CH_4$ detection, a polymer like PEI, or an organic-metal complex can provide the selectivity. Another attractive benefit for using nanostructures for chemical detection is that the adsorption of the analyte is directly converted to an electrical signal. This direct conversion of detection to an electrical signal allows nanostructure based devices to have ultra-low power consumption.

Optical and Plasmonic Sensors

The optical properties of molecules and nanomaterials are highly sensitive to the surrounding environment. This is true of organic dyes, but has particular application in monitoring the optical properties of plasmonic metal nanostructures, such as silver nanowires, or gold nanoparticles, and in semiconducting quantum dots. In these structures, small changes to the surface, for example the adsorption of a NO gas molecule, can result in large changes in the spectroscopic signal that can be detected in a number of methods (not exhaustive):

Blue or red shifts in absorption or emission spectra
Changes to the full width at half maximum for absorption or emission peaks
Fluorescence quenching or enhancement
Changes to the ratio of two or more peak intensities
Changes to the signal intensity at a particular wavelength These signal changes are particularly sensitive in nanostructures, and can be engineered for increased specificity using surface sensitizing agents or other surface modifications.

Resistive Sensor

Another sensing method is a simple resistive sensor. This sensor style may include functionalized nanostructures or un-functionalized nanostructures bridging at least two electrodes. The nanostructures may be deposited as a thin film or coating between the two electrodes. As the gas interacts with the nanostructures (functionalized or un-functionalized), the resistance or current across the system will change proportionally. Using nanostructures as a support provides several advantages. A coated nanostructure provides very high specific surface area (>200 $m^2/g$). Sensitivity and specificity may be enhanced by selecting appropriate functionalization materials.

In one embodiment, the resistive sensor contains two sensing chemistries configured as a Wheatstone bridge or other bridge circuit known in the art. In another embodiment, one of the two sensing chemistries in the Wheatstone or other bridge circuit is covered and serves as a reference chemistry. In another embodiment, a material that is impermeable or has poor permeability covers the reference chemistry. In another embodiment, at least one of the two chemistries is covered by a membrane that has selective permeably characteristics.

Figure 29:
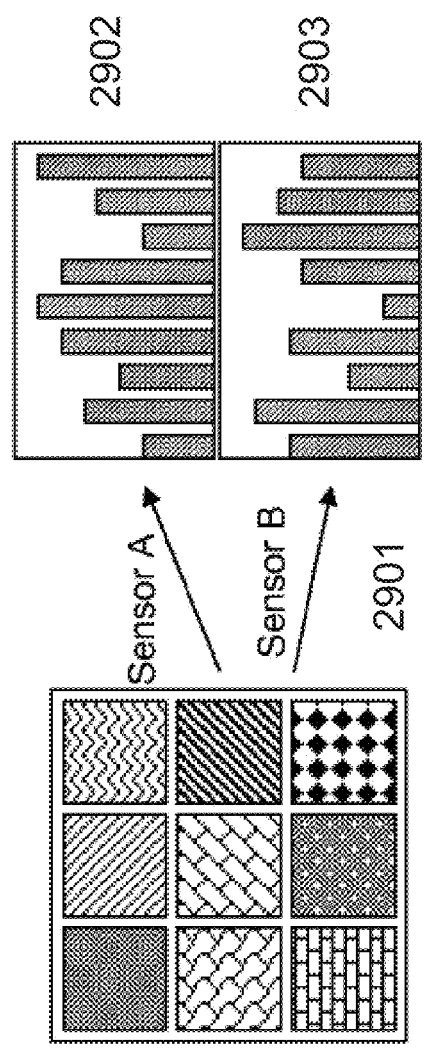
FIG. 29 demonstrates one embodiment of a sensor array.

In one embodiment, shown in FIG. 29 a multiplexed resistive sensor incorporates multiple sensing chemistries (2901) for detection. Each sensing chemistry may have different or the same sensitivity and specificities (2902, 2903). Incorporating several different sensing styles or sensor, eliminates or reduces problems associated with interfering species. Other examples are referenced herein.

One advantage of a multiplexed sensor is the ability to create signatures of gases or analytes. In one embodiment, an array of various sensors is used to establish a distinct pattern of responses over the array in the presence of specific analytes. In one embodiment, a multivariate partial least squares regression analysis is performed on the acquired sensor data to discern an analytes unique signature.

In one embodiment, a sensory array uses a large plurality of sensors.

In one embodiment, the sensors in the array may be sensitive to the same analyte or to a different set of analytes.

In other embodiments, the sensors may be configured in any arrangement as described herein by the authors.

The term sensor may be defined by any of the arrangements described herein by the authors.

In another embodiment, a sensor array consists of individual sensors. The individual sensor in the array consists of at least an active sensing chemistry and a reference chemistry configured in a Wheatstone bridge or other bridge circuit known in the art. In one embodiment, the reference chemistry is covered. In another embodiment, the reference chemistry is covered by an impermeable or poorly permeable membrane and the active chemistry is covered by a semi or selectively permeable membrane.

One benefit of multiple sensors is to reduce signal ambiguity in an environment of unknown background gases or analytes or fluids. Sensitivity is also enhanced with the use of multiple sensors. This boost in sensitivity is accomplished by summing a large number of individual low level responses. Furthermore, the presence of multiple sensors can provide additional information about interfering species, which increases the flexibility and breadth of the device.

Certain aspects of the techniques and systems disclosed herein may be implemented as a computer program product for use with a computer system or computerized electronic device. Such implementations may include a series of computer instructions, or logic, fixed either on a tangible medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Furthermore, such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The invention claimed is:

1. A test strip for determining the concentration of at least one analyte in a fluid sample having a plurality of analytes, the system comprising: a flexible base substrate; an electrode pair disposed over the base substrate; at least one sensing chemistry responsive to at least one analyte in the sample, wherein the at least one sensing chemistry is in electrical communication with the electrode pair; a first chromatographic layer disposed over the at least one sensing chemistry, wherein the at least one analyte of the plurality of analytes moves through the first chromatographic layer at a different rate relative to the movement of other analytes of the plurality of analytes; wherein the first chromatographic layer is affixed to the flexible base substrate; and wherein the first chromatographic layer comprises at least one of silicone, sulfonic acid, proton permeable membrane or acrylic acid; and at least one spacing layer, the at least one spacing layer disposed upon at least a portion of the base substrate, and the at least one spacing layer disposed upon at least a portion of the electrode pair, and wherein the at least one spacing layer at least in part defines a chamber, the at least one sensing chemistry disposed within the chamber.

2. The test strip of claim 1, further comprising a protective layer defining a window disposed above the at least one sensing chemistry.

3. The test strip of claim 2, wherein the first chromatographic layer is disposed above the protective layer.

4. The test strip of claim 2, wherein the protective layer defining the window is disposed above the first chromatographic layer.

5. The test strip of claim 1, wherein the at least one sensing chemistry is responsive to more than one analyte.

6. The test strip of claim 1, further comprising an inlet capable of receiving the fluid sample; and a flow controller in fluid communication with the inlet and the at least one sensing chemistry, wherein the flow controller is capable of providing at least a portion of the fluid sample to the at least one sensing chemistry.

7. The test strip of claim 1, further comprising a reader coupled to the at least one sensing chemistry via the electrode pair for determining a change in at least one of a physical, optical, and electrical property of the sensing chemistry when the at least one sensing chemistry is exposed to at least one analyte.

8. The test strip of claim 1, wherein the first chromatographic layer comprises at least one of porous polymers, non-porous polymers, composite materials, fibrous materials, woven textiles, non-woven textiles, polymer films, adhesives, metal films, ceramic films, and gels.

9. The test strip of claim 1, wherein the first chromatographic layer is affixed to a second layer using an adhesive or through lamination.

10. The test strip of claim 1, wherein the test strip is coupled to a reader.

11. The test strip of claim 1, wherein the first chromatographic layer is affixed to the flexible base through one or more intervening layers.

12. The test strip of claim 1, wherein the first chromatographic layer is affixed directly to the flexible base.

13. A method for determining the concentration of at least one analyte in a fluid sample, the method comprising: providing a system comprising: a flexible base substrate; an electrode pair disposed over the base substrate; at least one sensing chemistry responsive to at least one analyte in the sample, wherein the sensing chemistry is in electrical communication with the electrode pair; a first chromatographic layer disposed over the at least one sensing chemistry, wherein the at least one analyte of a plurality of analytes moves through the first chromatographic layer at a different rate relative to the movement of other analytes of the plurality of analytes; and wherein the first chromatographic layer is affixed to the flexible base substrate; and wherein the first chromatographic layer comprises at least one of silicone, sulfonic acid, proton permeable membrane or acrylic acid; and at least one spacing layer, the at least one spacing layer disposed upon at least a portion of the base substrate, and the at least one spacing layer disposed upon at least a portion of the electrode pair, and wherein the at least one spacing layer sensing chemistry, at least in part defines a chamber, the at least one sensing chemistry disposed within the chamber; measuring at least one of a voltage across the electrode pair, a resistance across the electrode pair, and a current flow across the electrode pair.

14. The method of claim 13, the measuring comprising analyzing a change in at least one of the voltage across the electrode pair, the resistance across the electrode pair, and the current flow across the electrode pair at a plurality of times.

* * * * *